(12) United States Patent
Bayburt et al.

(10) Patent No.: US 9,156,788 B2
(45) Date of Patent: *Oct. 13, 2015

(54) TRPV3 MODULATORS

(71) Applicant: AbbVie Inc., North Chicago, IL (US)

(72) Inventors: Erol K. Bayburt, Gurnee, IL (US);
Bruce Clapham, Lindenhurst, IL (US);
Phil B. Cox, Grayslake, IL (US);
Jerome F. Daanen, Racine, WI (US);
Arthur Gomtsyan, Vernon Hills, IL (US); Michael E. Kort, Lake Bluff, IL (US); Philip R. Kym, Libertyville, IL (US); Eric A. Voight, Pleasant Prairie, WI (US)

(73) Assignee: AbbVie Inc., North Chicago, IL (US)

( * ) Notice: Subject to any disclaimer, the term of this patent is extended or adjusted under 35 U.S.C. 154(b) by 115 days.

This patent is subject to a terminal disclaimer.

(21) Appl. No.: 13/761,862

(22) Filed: Feb. 7, 2013

(65) Prior Publication Data

US 2013/0150409 A1    Jun. 13, 2013

Related U.S. Application Data

(63) Continuation of application No. PCT/CN2010/001213, filed on Aug. 10, 2010.

(51) Int. Cl.
| | |
|---|---|
| *A61K 31/444* | (2006.01) |
| *C07D 213/30* | (2006.01) |
| *C07D 239/26* | (2006.01) |
| *C07D 401/04* | (2006.01) |
| *C07D 405/12* | (2006.01) |
| *C07D 213/50* | (2006.01) |
| *C07D 401/12* | (2006.01) |

(52) U.S. Cl.
CPC ............ *C07D 213/50* (2013.01); *C07D 401/12* (2013.01)

(58) Field of Classification Search
CPC .... A61K 31/44; C07D 213/30; C07D 239/26; C07D 401/04; C07D 405/12
USPC .................. 514/332, 334, 337, 277, 252.03; 546/339, 266, 344, 278.1, 268.1
See application file for complete search history.

(56) References Cited

U.S. PATENT DOCUMENTS

| | | | |
|---|---|---|---|
| 5,112,828 A | 5/1992 | Zipperer et al. | |
| 6,114,532 A | 9/2000 | Ries et al. | |
| 7,396,910 B2 | 7/2008 | Bevan et al. | |
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 8,772,499 B2 | 7/2014 | Bayburt et al. | |
| 8,772,500 B2 | 7/2014 | Bayburt et al. | |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0093516 A1 | 4/2009 | Li et al. | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |
| 2012/0010190 A1 | 1/2012 | Bissantz et al. | |

FOREIGN PATENT DOCUMENTS

| | | |
|---|---|---|
| CN | 101883772 A | 11/2010 |
| EP | 0400344 A1 | 12/1990 |
| IN | 200900517 A2 | 11/2010 |
| WO | 9429281 A1 | 12/1994 |
| WO | 9504042 A1 | 2/1995 |
| WO | 9507271 A1 | 3/1995 |
| WO | 9710223 A1 | 3/1997 |
| WO | 9940072 A1 | 8/1999 |
| WO | 0222572 A2 | 3/2002 |
| WO | 03086294 A2 | 10/2003 |
| WO | 2004043958 A1 | 5/2004 |
| WO | 2005099353 A2 | 10/2005 |
| WO | 2006008754 A1 | 1/2006 |
| WO | 2006122156 A2 | 11/2006 |
| WO | 2007056124 A2 | 5/2007 |
| WO | 2010004379 A2 | 1/2010 |
| WO | 2010070452 A1 | 6/2010 |
| WO | 2012019315 A1 | 2/2012 |
| WO | 2013062964 A1 | 5/2013 |
| WO | 2013062966 A2 | 5/2013 |

OTHER PUBLICATIONS

Alexander et al., "The Photochemical Synthesis of a Tricyclo[2.2.0. 02,5]hexane," J. American Chem. Soc., 1976, 98(14): 4324-4325.

(Continued)

*Primary Examiner* — Sreeni Padmanabhan
*Assistant Examiner* — Sahar Javanmard

(57) ABSTRACT

Disclosed herein are modulators of TRPV3 of formula (I)

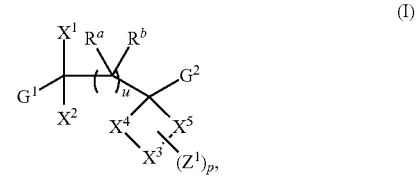

wherein $G^1$, $X^1$, $X^2$, $X^3$, $X^4$, $X^5$, $G^2$, $Z^1$, $R^a$, $R^b$, u, and p are as defined in the specification. Compositions comprising such compounds and methods for treating conditions and disorders using such compounds and compositions are also presented.

11 Claims, No Drawings

(56) References Cited

OTHER PUBLICATIONS

Aley et al., "Nitric oxide signaling in pain and nociceptor sensitization in the rat," J Neurosci., 1998, 18(17): 7008-7014.
Berge et al., "Pharmaceutical salts," J. Pharm Sci., 1977, 66(1): 1-19.
Beylot et al., "In vivo studies of intrahepatic metabolic pathways," Diabetes Metab., 1997, 23(3): 251-257.
Blagojevic et al., "Role of Heavy Water in Boron Neutron Capture Therapy," Topics in Dosimetry & Treatment Planning for Neutron Capture Therapy, R. Zamenhoff, G. Solares, O. Harling, Editors, 1994, Advanced Medical Publishing, Madison Wisconsin pp. 125-134.
Blake et al., "Studies with deuterated drugs," J Pharm Sci., 1975, 64(3): 367-391.
Brickner et al., "Synthesis and antibacterial activity of U-100592 and U-100766, two oxazolidinone antibacterial agents for the potential treatment of multidrug-resistant gram-positive bacterial infections," J Med Chem., 1996, 39(3): 673-679.
Caterina, MJ, "Transient receptor potential ion channels as participants in thermosensation and thermoregulation," Am J Physiol Regul Integr Comp Physiol., 2007, 292(1): R64-R76.
Caterina et al., "A capsaicin-receptor homologue with a high threshold for noxious heat," Nature, 1999, 398(6726): 436-441.
Chung et al., "2-aminoethoxydiphenyl borate activates and sensitizes the heat-gated ion channel TRPV3," J Neurosci. 2004, 24(22):5177-5182.
Chung et al., "Biphasic currents evoked by chemical or thermal activation of the heat-gated ion channel, TRPV3," J Biol Chem., 2005, 280(16): 15928-15941.
Chung et al., "Warm temperatures activate TRPV4 in mouse 308 keratinocytes," J Biol Chem., 2003, 278(34): 32037-32046.
Chung et al., "TRPV3 and TRPV4 mediate warmth-evoked currents in primary mouse keratinocytes," J Biol Chem., 2004, 279(20): 21569-21575.
Coppi et al., "2-Lithiated-2-phenyloxetane: a new attractive synthon for the preparation of oxetane derivatives," Chem. Commun (Camb)., 2011, 47(35): 9918-9920.
Czajka et al., "Effect of deuterium oxide on the reproductive potential of mice," Ann N Y Acad Sci., 1960, 84: 770-779.
Czajka et al., "Physiological effects of deuterium on dogs," Am J Physiol. 1961, 201(2): 357-362.
Dörwald, FZ, "1.3 Hard and Soft Acids and Bases," Side Reactions in Organic Synthesis, 2005, Wiley-VCH, Weinheim (390 pages).
Drug labeling information for Tylenol® with codeine, Revised Aug. 2010, taken from PDR® 3D™ (Digital Drug Database) available at www.pdrnetwork.com, printed Mar. 22, 2013 (9 pages).
Facer et al., "Differential expression of the capsaicin receptor TRPV1 and related novel receptors TRPV3, TRPV4 and TRPM8 in normal human tissues and changes in traumatic and diabetic neuropathy," BMC Neurol., 2007, 7: 11-22.
Foster et al., "Deuterium Isotope Effects in the Metabolism of Drugs and Xenobiotics: Implications for Drug Design," Advances in Drug Research, 1985, vol. 14 Academic press, London, pp. 2-36.
Green et al. Editors, Protecting Groups in Organic Synthesis, 3rd Ed., John Wiley & Sons, NY, 1999, 20 pages.
Güler et al., "Heat-evoked activation of the ion channel, TRPV4," J Neurosci., 2002, 22(15): 6408-6414.
Hailes et al., "2.05—Oxetanes and Oxetenes: Monocyclic" Comprehensive Heterocyclic Chemistry III, Elsevier, Oxford, 2008, pp. 321-364.
Hardouin et al, "BF3•OEt2-Mediated Rearrangement of Cyclopropyl Carbinols: A Concise Route to Polycyclic Cyclobutanes," J. Org. Chem., 66(12): 4450-4452 (2001).
Harper et al., "1-3,4-Dichlorobenzamidomethyl)cyclohexyldimethylamine and Related Compounds as Potential Analgesics," Journal of Medicinal Chemistry, 1974, 17(11): 1188-1193.
Hattersley et al., "Some Reactions with 4-Cyano-4-phenyltetrahydropyran" Journal of Medicinal Chemistry, 1967, 10(1): 128-129.
Hu et al., "2-aminoethoxydiphenyl borate is a common activator of TRPV1, TRPV2, and TRPV3," J Biol Chem., 2004, 279(34): 35741-35748.
Hu et al., "Potentiation of TRPV3 channel function by unsaturated fatty acids," J Cell Physiol. 2006, 208(1): 201-212.
International Search Report and Written Opinion for PCT/CN2010/001213, mailed May 19, 2011 (11 pages).
International Search Report and Written Opinion for PCT/CN2011/001761, mailed Aug 2, 2012 (17 pages).
International Search Report and Written Opinion for PCT/US2012/061476, mailed Jun. 17, 2013 (17 pages).
International Search Report and Written Opinion for PCT/US2012/061478, mailed Jun. 17, 2013 (19 pages).
IUPAC 1974 Recommendations for Section E, Fundamental Stereochemistry, Pure Appl. Chem., 1976, 45: 13-30.
Kanemoto et al., "Novel Synthesis of Monofluorocyclobutanes by the Ring Expansion Fluorination of Cyclopropylmethanols With an Amine-Metal, Fluoride-Pyridinium Poly(Hydrogen Fluoride)-Complex," Tetrahedron Letters, 28(5): 6313-6316 (1987).
Kato et al., "Synthesis of Deuterated Mosapride Citrate," J Labelled Compd Rad., 1995, 36(10): 927-932.
Kushner et al., "Pharmacological uses and perspectives of heavy water and deuterated compounds," Can J Physiol Pharmacol., 1999, 77(2): 79-88.
Lee et al., "TRPV channels as thermosensory receptors in epithelial cells," Pflugers Arch.—Eur J Physiol. 2005, 451(1): 160-167.
Lee-Ruff et al., "Enantiomerically pure cyclobutane derivatives and their use in organic synthesis," Chem Rev., 2003, 103(4): 1449-1483.
Lizondo et al., "Linezolid. Oxazolidinone Antibacterial," Drugs Fut., 1996, 21(11): 1116-1123.
MacPherson et al., "More than cool: promiscuous relationships of menthol and other sensory compounds" Mol Cell Neurosci. 2006, 32(4): 335-343.
Mallesham et al., "Highly efficient CuI-catalyzed coupling of aryl bromides with oxazolidinones using Buchwald's protocol: a short route to linezolid and toloxatone," Org Left., 2003, 5(7): 963-965.
McCarty et al., "Central Stimulants. α,α-Disubstituted 2-Piperidinemethanols and 1,1-Disubstitued Heptahydrooxazolo [3,4-a]pyridines," J. Am. Chem. Soc., 179(2): 472-480 (1957).
Montell, C. "Preventing a Perm with TRPV3," Cell, 2010, 141(2): 218-220.
Moqrich et al., "Impaired thermosensation in mice lacking TRPV3, a heat and camphor sensor in the skin," Science, 2005, 307(5714): 1468-1472.
Moussaieff et al., "Incensole acetate, an incense component, elicits psychoactivity by activating TRPV3 channels in the brain," FASEB J., 2008, 22(8): 3024-3034.
Nilius et al., "Transient receptor potential cation channels in disease," Physiol Rev., 2007, 87(1): 165-217.
Okuhara et al., "Transient receptor potential channels as drug targets," Expert Opin Ther Targets, 2007, 11(3): 391-401.
Ong et al., "Novel Tetracyclic Spiropiperidines. II. Synthesis of 2-Aryl-2,3-dihydrospiro[benzofuran-3,4'-piperidines] (1,2)," Journal of Heterocyclic Chemistry, 1981, 18(4): 815-820.
Peier et al., "A heat-sensitive TRP channel expressed in keratinocytes," Science, 2002, 296(5575): 2046-2049.
Prescott, D.M., Editor, "Methods in Cell Biology," vol. XIV, Academic Press, New York, N.Y. 1976, 12 pages.
Smith et al., "TRPV3 is a temperature-sensitive vanilloid receptor-like protein," Nature 2002, 418(6894): 186-190.
Steinhoff et al., "A TR(I)P to pruritus research: role of TRPV3 in inflammation and itch," J. Invest. Dermatology, 2009, 129(3): 531-535.
Thomson JF, "Physiological effects of D20 in mammals," Ann NY Acad Sci., 1960, 84: 736-744.
Vogt-Eisele et al., "Monoterpenoid agonists of TRPV3," Br J Pharmacol. 2007, 151(4): 530-540.
Wermuth Editor, The Practice of Medicinal Chemistry, 3rd Edition, Elsevier, 2008, pp. 126, 276, 294, 328, 343, 350, 431, 432, 440, 452, 533, 535, 536, 724 and 725.

(56) References Cited

OTHER PUBLICATIONS

Wissenbach et al., "TRP channels as potential drug targets," Biology of the Cell., (2004), 96(1): 47-54.

Xu et al., "Camphor activates and strongly desensitizes the transient receptor potential vanilloid subtype 1 channel in a vanilloid-independent mechanism," J Neurosci. 2005, 25(39): 8924-8937.

Xu et al., "Oregano, thyme and clove-derived flavors and skin sensitizers activate specific TRP channels," Nat Neurosci. 2006, 9(5): 628-635.

Xu et al., "TRPV3 is a calcium-permeable temperature-sensitive cation channel," Nature, 2002, 418(6894): 181-186.

Yoshida et al., Editors, "Nitric oxide activates TRP channels by cysteine S-nitrosylation," Nat Chem Biol., 2006, 2(11): 596-607.

Yus et al., "Intramolecular carbolithiation promoted by a DTBB-catalysed chlorine—lithium exchange," Tetrahedron, 59(43):8525-8542 (2003).

Zhang et al., "Cyclization reactions of 3,3-dimethyl-1-(1H-1,2,4-triazolo-1-yl)-2-butanone or substituted 1-(1H-1,2,4-triazolo-1-yl)acetophenone with dibromide compounds and its biological activities," Gaodeng Xuexiao Huaxue Xuebao, 24(3): 431-435 (retrieved from STN Database accession No. 2003:247751 abstract).

U.S. Appl. No. 13/658,374, filed Oct. 23, 2012, File History.

U.S. Appl. No. 13/658,355, filed Oct. 23, 2012, File History.

Extended European Search Report for Application No. 10855736.4 dated Dec. 4, 2013.

TRPV3 MODULATORS

CROSS REFERENCE SECTION TO RELATED APPLICATION

This application is a continuation of International Application No. PCT/CN2010/001213 filed on Aug. 10, 2010, which is incorporated by reference in its entirety.

TECHNICAL FIELD

Compounds that are Transient Receptor Potential Vanilloid 3 (TRPV3) modulators, compositions comprising such compounds, and methods for treating conditions and disorders using such compounds and compositions, are disclosed herein.

BACKGROUND OF THE INVENTION

A subset of the vanilloid channels (TRPV1-4) are referred to as thermoTRPs to reflect the observation that heat elicits channel opening across a continuum of temperatures with thresholds ranging from 25° C. to 52° C. (Caterina, M. J.; Rosen, T. A.; Tominaga, M.; Brake, A. J.; Julius, D., *Nature* 1999, 398, 436-441). TRPV3 characteristically responds to innocuous heat >31° C., exhibits exquisite sensitivity around the physiological temperature of humans, 37° C., and sensitizes dramatically following repetitive heating (Smith, G. D.; Gunthorpe, M. J.; Kelsell, R. E.; Hayes, P. D.; Reilly, P.; Facer, P.; Wright, J. E.; Jerman, J. C.; Walhin, J. P.; Ooi, L.; Egerton, J.; Charles, K. J.; Smart, D.; Randall, A. D.; Anand, P.; Davis, J. B., *Nature* 2002, 418, 186-190.; Xu, H.; Ramsey, I. S.; Kotecha, S. A.; Moran, M. M.; Chong, J. A.; Lawson, D.; Ge, P.; Lilly, J.; Silos-Santiago, I.; Xie, Y.; DiStefano, P. S.; Curtis, R.; Clapham, D. E., *Nature* 2002, 418, 181-186; Peier, A. M.; Reeve, A. J.; Andersson, D. A.; Moqrich, A.; Earley, T. J.; Hergarden, A. C.; Story, G. M.; Colley, S.; Hogenesch, J. B.; McIntyre, P.; Bevan, S.; Patapoutian, A., *Science* 2002, 296, 2046-2049).

TRPV3 is a nonselective cation channel with permeability for calcium, but also to other cations, for example sodium. Multiple compounds that have been shown to activate TRPV3, include: monoterpenes, camphor (Peier, A. M. et al., 2002; Moqrich, A.; Hwang, S. W.; Earley, T. J.; Petrus, M. J.; Murray, A. N.; Spencer, K. S.; Andahazy, M.; Story, G. M.; Patapoutian, A., *Science* 2005, 307, 1468-1472; Xu, H.; Blair, N. T.; Clapham, D. E., J. Neurosci. 2005, 25, 8924-8937), carvacrol, and thymol (Xu, H.; Delling, M.; Jun, J. C.; Clapham, D. E. *Nat. Neurosci.* 2006, 9, 628-635; Vogt-Eisele, A. K.; Weber, K.; Sherkheli, M. A.; Vielhaber, G.; Panten, J.; Gisselmann, G.; Hatt, H., *Br J Pharmacol.* 2007, 151, 530-540; Earley, S.; Gonzales, A. L.; Garcia, Z. I., *Mol Pharmacol.* 2010, Jan. 19. [Epub ahead of print]); menthol (Macpherson, L. J.; Hwang, S. W.; Miyamoto, T.; Dubin, A. E.; Patapoutian, A; Story, G. M., *Mol Cell Neurosci.* 2006, 32, 335-343; Vogt-Eisele, A. K. et al., 2007); cinnamaldehyde (Macpherson, L. J. et al., 2006); incensole acetate (Moussaieff, A.; Rimmerman, N.; Bregman, T.; Straiker, A.; Felder, C. C.; Shoham, S.; Kashman, Y.; Huang, S. M.; Lee, H.; Shohami, E.; Mackie, K.; Caterina, M. J.; Walker, J. M.; Fride, E.; Mechoulam, R., *FASEB J.* 2008, 22, 3024-3034.); and vanilloid analogs, eugenol and ethyl vanillin (Hu, H. Z.; Gu, Q.; Wang, C.; Colton, C. K.; Tang, J.; Kinoshita-Kawada, M.; Lee, L. Y.; Wood, J. D.; Zhu, M. X., *J Biol. Chem.* 2004, 279, 35741-35748; Vogt-Eisele, A. K. et al., 2007; Xu, H. et al., 2006). Though relatively weak ($EC_{50}$, ~40 M) and non-specific across TRPs, 2-aminoethoxydiphenylborate (2-APB) and diphenylboronic anhydride (DPBA) have been widely and productively used to characterize key attributes of TRPV3 in cellular assays and electrophysiology (Hu, H. Z. et al., 2004; Chung, M. K.; Lee, H.; Mizuno, A.; Suzuki, M.; Caterina, M. J. *J Neurosci.* 2004, 24, 5177-5182; Chung, M. K.; Güler, A. D.; Caterina, M. J., *J Biol. Chem.* 2005, 280, 15928-15941). While heat and direct ligand binding are clearly central to TRPV3 pharmacology, accumulating evidence of potentiation by arachidonic acid, other unsaturated fatty acid derivatives (Hu, H. Z.; Xiao, R.; Wang, C.; Gao, N.; Colton, C. K.; Wood, J. D.; Zhu, M. X., *J Cell Physiol.* 2006, 208, 201-212), and nitric oxide (Aley, K. O.; McCarter, G.; Levine, J. D., *J Neurosci.* 1998, 18, 7008-7014; Yoshida, T.; Inoue, R.; Morii, T.; Takahashi, N.; Yamamoto, S.; Hara, Y.; Tominaga, M.; Shimizu, S.; Sato, Y.; Mori, Y., *Nat Chem. Biol.* 2006, 2, 596-607) suggests that authentic activation involves stimulation of G protein-coupled receptors and downstream second messenger signal cascades (e.g., phospholipase C, protein kinase C) that mediate local inflammatory responses and nociceptor sensitization that could enhance TRPV3 function (Xu, H. et al., 2006) in a pathophysiological, as compared to basal, state.

Evidence suggests that transcriptional regulation of the TRPV3 gene restricts its basal expression and is responsible for enhanced expression following nerve injury. Levels of TRPV3 mRNA recovered from rat L4 and L5 DRG neurons is elevated in the spinal nerve ligation model of neuropathic pain, as compared to uninjured rats (U.S. Pat. No. 7,396,910). Similar upregulation of TRPV3 has been observed in sensory neurons following peripheral nerve injury in humans (Facer, P.; Casula, M. A.; Smith, G. D.; Benham, C. D.; Chessell, I. P.; Bountra, C.; Sinisi, M.; Birch, R.; Anand, P., *BMC Neurol.* 2007, 7, 11-22; Smith G. D. et al., 2002).

One feature that distinguishes TRPV3 from the other thermoTRPs is its relatively prominent localization in skin (Peier, A. M. et al., 2002; Xu, H. et al., 2002). TRPV3 is also expressed in dorsal root ganglion, trigeminal ganglion, spinal cord and brain (Xu, H. et al., 2002; Smith G. D. et al., 2002). Its distinctive tissue profile, with significant expression in keratinocytes proximal to nociceptive neurons (Chung, M. K.; Lee, H.; Caterina, M. J., *J Biol. Chem.* 2003, 278, 32037-32046; Chung, M. K.; Lee, H.; Mizuno, A.; Suzuki, M.; Caterina, M. J. *J Biol. Chem.* 2004, 279, 21569-21575; Peier, A. M. et al., 2002; Xu, H. et al., 2002) as well as upregulation of TRPV3 in disease states is consistent with a likely role of TRPV3 in pain (Caterina M J., *Am J Physiol Regul Integr Comp Physiol.* 2007, 292, R64-R76; Lee, H.; Caterina, M. J., *Pflugers Arch.* 2005, 451, 160-167; Güler, A. D.; Lee, H.; Iida, T.; Shimizu, I.; Tominaga, M.; Caterina, M., *J Neurosci.* 2002, 22, 6408-6414; Chung, M. K. et al., 2003; Chung, M. K.; Lee, H.; Mizuno, A.; Suzuki, M.; Caterina, M. J. *J Biol. Chem.* 2004, 279, 21569-21575). In a keratinocyte cell line, stimulation of TRPV3 leads to release of inflammatory mediators including interleukin-1. Thus TRPV3 may also play an important role in regulating inflammation, itch (Steinhoff, M. and Biro, T. *J. Invest. Dermatology*, 2009, 129, 531-535) and pain that results from the release of inflammatory stimuli. In addition, localization of TRPV3 in non-neuronal tissues, especially skin, suggests also that pharmacological modulation of the channel may provide a therapy to treat diseases that impair the skin barrier (Montell, C. *Cell*, 2010, Apr. 16, 218-220) and have additional, as yet unidentified, benefit for disease states beyond pain. Accordingly, compounds that can modulate one or more functions of TRPV3 can have various therapeutic utilities.

SUMMARY OF THE INVENTION

Disclosed herein are compounds of formula (I)

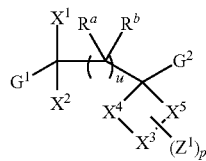

(I)

or pharmaceutically acceptable salts, solvates, salts of solvates, or solvates of salts thereof, wherein each occurrence of $R^a$ and $R^b$, are each independently hydrogen, alkyl, haloalkyl, halogen, OH, O(alkyl), or optionally substituted phenyl;

u is 0, 1, or 2;

$X^3$ is $CH_2$, O, S, $S(O)_2$, or $N(R^{1x})(R^{2x})$ wherein $R^{1x}$ and $R^{2x}$ are the same or different, and are each independently hydrogen, alkyl, or —C(O)CH$_3$;

$X^4$ is a bond or $(CH_2)_m$ and $X^5$ is a bond or $(CH_2)_n$; with the proviso that only one of $X^4$ and $X^5$ is a bond, and that when one of $X^4$ and $X^5$ is a bond, and m or n is 1, then $X^3$ is $CH_2$;

m and n are integers that can be the same or different, and are each independently 1, 2, 3, or 4;

each $Z^1$ group is an optional substituent on any substitutable carbon atom of the ring containing $X^3$, $X^4$, and $X^5$, and is independently alkyl, O(alkyl), oxo, halogen, haloalkyl, or OH; two $Z^1$ groups that are resided on the same carbon atom, together with the carbon atom to which they are attached optionally form a 4-6 membered monocyclic heterocycle ring containing one or two oxygen atoms;

p is 0, 1, 2, 3, or 4;

—X is —OH and $X^2$ is hydrogen; or —$X^1$ is =NOR$^{10}$ and $X^2$ is absent wherein $R^{10}$ is hydrogen, alkyl, or —C(O)alkyl;

$G^1$ is aryl, heteroaryl, cycloalkyl, heterocycle, or cyclaoalkenyl; optionally substituted with 1, 2, 3, 4, or 5 substituents independently selected from the group consisting of alkyl, alkenyl, alkynyl, halogen, haloalkyl, OH, O(alkyl), NH$_2$, N(H)(alkyl), N(alkyl)$_2$, heteroaryl, and heterocycle; wherein the heteroaryl and the heterocycle moieties are each independently unsubstituted or substituted with 1, 2, 3, 4, or 5 substituents selected from the group consisting of alkyl, O(alkyl), halogen, and haloalkyl;

$G^2$ is $G^{2d}$ or —$(CR^{1g}R^{2g})_r$-$G^{2d}$ wherein r is 1, 2, or 3;

$R^{1g}$ and $R^{2g}$ are the same or different, and are each independently hydrogen, alkyl, O(alkyl), C(O)CH$_3$, or haloalkyl;

$G^{2d}$ is aryl, heteroaryl, cycloalkyl, heterocycle, or cyclaoalkenyl, optionally substituted with 1, 2, 3, 4, or 5 substituents independently selected from the group consisting of $G^d$, alkyl, alkenyl, alkynyl, halogen, haloalkyl, —CN, —OR$^f$, —OC(O)R$^f$, —OC(O)N(R$^f$)$_2$, —S(O)$_2$R$^e$, —S(O)$_2$N(R$^f$)$_2$, —C(O)R$^f$, —C(O)OR$^f$, —C(O)N(R$^f$)$_2$, —N(R$^f$)$_2$, —N(R$^f$)C(O)R$^f$, —N(R$^f$)S(O)$_2$R$^e$, —N(R$^f$)C(O)O(R$^e$), —N(R$^f$)C(O)N(R$^f$)$_2$, —(CR$^{1a}$R$^{1b}$)$_q$-G$^d$, —(CR$^{1a}$R$^{1b}$)$_q$—OR$^f$, —(CR$^{1a}$R$^{1b}$)$_q$—OC(O)R$^f$, —(CR$^{1a}$R$^{1b}$)$_q$—OC(O)N(R$^f$)$_2$, —(CR$^{1a}$R$^{1b}$)$_q$—S(O)$_2$R$^e$, —(CR$^{1a}$R$^{1b}$)$_q$—S(O)$_2$N(R$^f$)$_2$, —(CR$^{1a}$R$^{1b}$)$_q$—C(O)R$^f$, —(CR$^{1a}$R$^{1b}$)$_q$—C(O)OR$^f$, —(CR$^{1a}$R$^{1b}$)$_q$—C(O)N(R$^f$)$_2$, —(CR$^{1a}$R$^{1b}$)$_q$—N(R$^f$)$_2$, —(CR$^{1a}$R$^{1b}$)$_q$—N(R$^f$)C(O)R$^f$, —(CR$^{1a}$R$^{1b}$)$_q$—N(R$^f$)S(O)$_2$R$^e$, —(CR$^{1a}$R$^{1b}$)$_q$—N(R$^f$)C(O)O(R$^e$), —(CR$^{1a}$R$^{1b}$)$_q$—N(R$^f$)C(O)N(R$^f$)$_2$, and —(CR$^{1a}$R$^{1b}$)$_q$—CN;

$R^{1a}$ and $R^{1b}$, are the same or different, and at each occurrence are each independently hydrogen, alkyl, or haloalkyl;

each occurrence of $R^f$ is independently hydrogen, alkyl, haloalkyl, $G^d$, or —(CR$^{1a}$R$^{1b}$)$_q$-G$^d$;

each occurrence of $R^e$ is independently alkyl, haloalkyl, $G^d$, or —(CR$^{1a}$R$^{1b}$)$_q$-G$^d$;

q, at each occurrence, is independently 1, 2, or 3;

each occurrence of $G^d$ is independently aryl, heteroaryl, cycloalkyl, heterocycle, or cyclaoalkenyl; and is each optionally substituted with 1, 2, 3, 4, or 5 substituents independently selected from the group consisting of alkyl, alkenyl, alkynyl, halogen, haloalkyl, —CN, —OR$^j$, —OC(O)R$^j$, —OC(O)N(R$^j$)$_2$, —S(O)$_2$R$^k$, —S(O)$_2$N(R$^j$)$_2$, —C(O)R$^j$, —C(O)OR$^j$, —C(O)N(R$^j$)$_2$, —N(R$^j$)$_2$, —N(R$^j$)C(O)R$^j$, —N(R$^j$)S(O)$_2$R$^k$, —N(R$^j$)C(O)O(R$^k$), —N(R$^j$)C(O)N(R$^j$)$_2$, —(CR$^{1a}$R$^{1b}$)$_q$—OR$^j$, —(CR$^{1a}$R$^{1b}$)$_q$—OC(O)R$^j$, —(CR$^{1a}$R$^{1b}$)$_q$—OC(O)N(R$^j$)$_2$, —(CR$^{1a}$R$^{1b}$)$_q$—S(O)$_2$R$^k$, —(CR$^{1a}$R$^{1b}$)$_q$—S(O)$_2$N(R$^j$)$_2$, —(CR$^{1a}$R$^{1b}$)$_q$—C(O)R$^j$, —(CR$^{1a}$R$^{1b}$)$_q$—C(O)OR$^j$, —(CR$^{1a}$R$^{1b}$)$_q$—C(O)N(R$^j$)$_2$, —(CR$^{1a}$R$^{1b}$)$_q$—N(R$^j$)$_2$, —(CR$^{1a}$R$^{1b}$)$_q$—N(R$^j$)C(O)R$^j$, —(CR$^{1a}$R$^{1b}$)$_q$—N(R$^j$)S(O)$_2$R$^k$, —(CR$^{1a}$R$^{1b}$)$_q$—N(R$^j$)C(O)O(R$^k$), —(CR$^{1a}$R$^{1b}$)$_q$—N(R$^j$)C(O)N(R$^j$)$_2$, and —(CR$^{1a}$R$^{1b}$)$_q$—CN;

each occurrence of $R^j$ is independently hydrogen, alkyl, or haloalkyl; and each occurrence of $R^k$ is independently alkyl or haloalkyl.

Another aspect relates to pharmaceutical compositions comprising therapeutically effective amount of a compound described herein or pharmaceutically acceptable salt, solvate, salt of a solvate, or solvate of a salt thereof, in combination with a pharmaceutically acceptable carrier. Such compositions can be administered in accordance with methods described herein, typically as part of a therapeutic regimen for treatment or prevention of conditions and disorders related to TRPV3 activity. More particularly, the methods are useful for treating conditions related to pain such as, but not limited to, chronic pain, neuropathic pain, nociceptive pain, osteoarthritic pain, inflammatory pain, cancer pain, lower back pain, post operative pain, and eye pain.

Further, provided herein are uses of the present compounds or pharmaceutically acceptable salts, solvates, or salts of solvates thereof, in the manufacture of medicaments for the treatment of the disease or conditions described above, alone or in combination with a pharmaceutically acceptable carrier, particularly for the treatment of pain such as, but not limited to, chronic pain, neuropathic pain, nociceptive pain, osteoarthritic pain, inflammatory pain, cancer pain (e.g. bone cancer pain), lower back pain, post operative pain, and eye pain, or combinations thereof.

The compounds, compositions comprising the compounds, pharmaceutically acceptable salts, solvates, salts of the solvates, or solvates of the salts thereof, and methods for treating or preventing conditions and disorders by administering the compounds or compositions thereof, are further described herein.

These and other objectives are described further in the following paragraphs. These objectives should not be deemed to narrow the scope of the invention.

DETAILED DESCRIPTION OF THE INVENTION

Compounds of formula (I)

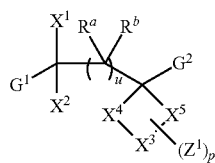

wherein $G^1$, $X^1$, $X^2$, $X^3$, $X^4$, $X^5$, $G^2$, $Z^1$, $R^a$, $R^b$, u, and p are as defined above in the Summary and below in the Detailed Description are disclosed. Compositions comprising such compounds and methods for treating conditions and disorders using such compounds and compositions are also disclosed.

In various embodiments, compounds described herein may contain variables that occur more than one time in any substituent or in the compound described or any other formulae herein. Definition of a variable on each occurrence is independent of its definition at another occurrence. Further, combinations of variables are permissible only if such combinations result in stable compounds. Stable compounds are compounds that can be isolated from a reaction mixture.

A. DEFINITIONS

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optional a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_4$ alkenyl" means an alkenyl group containing 2-4 carbon atoms. Non-limiting examples of alkenyl include buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double.

Representative examples of alkenylene include, but are not limited to, —CH═CH— and —CH$_2$CH═CH—.

The term "alkyl" as used herein, means a straight or branched, saturated hydrocarbon chain containing from 1 to 10 carbon atoms. The term "$C_x$-$C_y$ alkyl" means a straight or branched chain, saturated hydrocarbon containing x to y carbon atoms. For example "$C_2$-$C_{10}$ alkyl" means a straight or branched chain, saturated hydrocarbon containing 2 to 10 carbon atoms. For example "$C_1$-$C_4$ alkyl" means a straight or branched chain, saturated hydrocarbon containing 1 to 4 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched, saturated hydrocarbon chain of 1 to 10 carbon atoms, for example, of 1 to 4 carbon atoms. Examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "$C_2$-$C_4$ alkynyl" means an alkynyl group containing from 2 to 4 carbon atoms. Representative examples of alkynyl include, but are not limited to, acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the aryl groups include dihydroindenyl (e.g. 2,3-dihydro-1H-inden-1-yl), indenyl, naphthyl, dihydronaphthalenyl, and tetrahydronaphthalenyl (e.g. 1,2,3,4-tetrahydronaphthalen-1-yl). The aryl groups can be unsubstituted or substituted, and the bicyclic aryl is attached to the parent molecular moiety through any substitutable carbon atom contained within the bicyclic ring system.

The term "cycloalkyl" or "cycloalkane" as used herein, means a monocyclic or a bicyclic. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. The monocyclic or bicyclic cycloalkyl ring may contain one or two alkylene bridges, each consisting of one, two, three, or four carbon atoms, each linking two non-adjacent carbon atoms of the ring system. Non-limiting examples of such bridged cycloalkyl ring systems include bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic and the bicyclic cycloalkyls can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, three, or four carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. The term "$C_1$-$C_4$ haloalkyl" means a $C_1$-$C_4$ alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, trifluorobutyl (such as, but not limited to, 4,4,4-trifluorobutyl), and trifluoropropyl (such as, but not limited thereto, 3,3,3-trifluoropropyl).

The term "heterocycle" or "heterocyclic" as used herein, means a monocyclic heterocycle or a bicyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S, Non-limiting examples of monocyclic heterocycles include azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Non-limiting examples of bicyclic heterocycles include e.g. dihydrochromenyl (e.g. 3,4-dihydro-2H-chromen-4-yl), benzopyranyl, benzothiopyranyl, 2,3-dihydrobenzofuranyl, 2,3-dihydrobenzothienyl, and 2,3-dihydro-1H-indolyl. The monocyclic and the bicyclic heterocycles may contain an alkenylene bridge of two, three, or four carbon atoms, or one or two alkylene bridges of 1, 2, 3, or 4 carbon atoms, or combinations thereof, wherein each bridge links two non-adjacent atoms of the ring system. Non-limiting examples of such bridged heterocycles include octahydro-2,5-epoxypentalene, azabicyclo[2.2.1]heptyl (including 2-azabicyclo[2.2.1]hept-2-yl), hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The monocyclic and the bicyclic heterocycles can be unsubstituted or substituted, and are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quarternized.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Non-limiting examples of bicyclic heteroaryl groups include benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups can be substituted or unsubstituted and are connected to the parent molecular moiety through any substitutable carbon atom or any substitutable nitrogen atom contained within the ring systems.

The term "heteroatom" as used herein, means a nitrogen, oxygen, or sulfur atom.

The term "oxo" as used herein, means a =O group.

"Treatment" or "treating" pain includes acute or chronic pain and refers to: (1) preventing pain, i.e. causing pain not to develop or occur with less intensity in a subject that may be exposed or predisposed to pain but does not yet experience or display pain, (2) inhibiting pain, i.e., arresting the development or reversing pain, or (3) relieving pain, i.e., decreasing the amount of pain experienced by the subject.

The term "subject" includes animals such as mammals, including, but not limited to, primates (e.g., humans), cows, sheep, goats, horses, dogs, cats, rabbits, rats, mice and the like. In preferred embodiments, the subject is a human.

B. COMPOUNDS

Compounds of formula (I) are as described above.

Particular values of variable groups in compounds of formula (I) are as follows. Such values may be used where appropriate with any of the other values, definitions, claims or embodiments defined hereinbefore or hereinafter.

$R^a$, $R^b$, and u have values as described in the Summary. For example, in certain embodiments, u is 0 or 1. In certain embodiments, u is 0. In yet other embodiments, u is 1. In conjunction with any of the embodiments described herein above or below, $R^a$ and $R^b$, for example, are hydrogen.

Examples of compounds of formula (I) wherein u is 0 can be exemplified by compounds of formula (I-a)

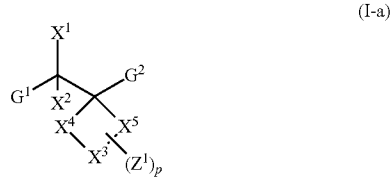

(I-a)

wherein $G^1$, $G^2$, $X^1$, $X^2$, $X^3$, $X^4$, $X^5$, $Z^1$, and p are as disclosed in the Summary and embodiments herein below.

$X^1$ and $X^2$ for formula (I) and (I-a) have values as described in the Summary.

For example, in certain embodiments, —$X^1$ is —OH and $X^2$ is hydrogen, as exemplified by formula (I-i)

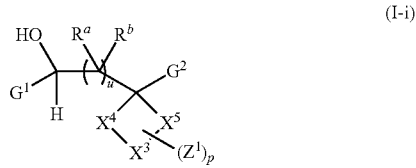

(I-i)

Compounds of formula (I-i) may exist as stereoisomers wherein asymmetric or chiral centers are present. Thus, contemplated are compounds of formula (I-i-a), (I-i-b), and mixtures (including racemic mixtures) of various ratios thereof:

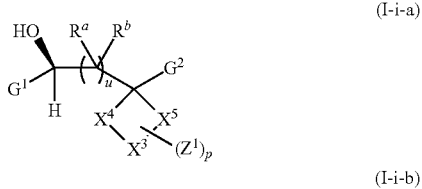

(I-i-a)

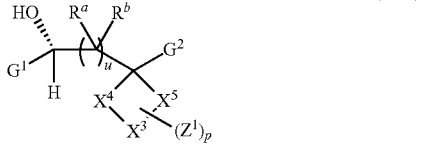

(I-i-b)

In certain embodiments, $X^2$ is absent, and —$X^1$ is =$NOR^{10}$ wherein $R^{10}$ is hydrogen, alkyl, or —C(O)alkyl, and $X^2$ is absent. Thus, included, but not limited to, are compounds of formula (I-ii)

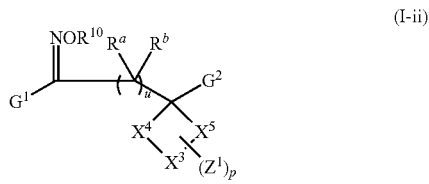

(I-ii)

$G^1$, $G^2$, $X^3$, $X^4$, $X^5$, $Z^1$, $R^{10}$, $R^a$, $R^b$, u, and p for formula (I-a), (I-i), (I-i-a), (I-i-b), and (I-ii) have values as described in the Summary for formula (I) and embodiments herein.

In conjunction with any of the embodiments disclosed above and below, $R^{10}$ has values as described in the Summary and herein. For example, in certain embodiments $R^{10}$ is hydrogen.

$X^3$, $X^4$, and $X^5$ for compounds of formula (I), (I-a), (I-i), (I-i-a), (I-i-b), and (I-ii) are as described in the Summary. $X^3$, for example, is $CH_2$ or O. In certain embodiments, $X^3$ is O. In certain embodiments, $X^3$ is $CH_2$.

In certain embodiments, $X^3$ is O, $X^4$ is $(CH_2)_m$, and $X^5$ is $(CH_2)_n$ wherein m and n are each independently 1 or 2.

In certain embodiments, $X^3$ is O, one of $X^4$ and $X^5$ is a bond, and the other is $(CH_2)_3$ or $(CH_2)_4$.

In certain embodiments, $X^3$ is $CH_2$, $X^4$ is a bond or $(CH_2)_m$, and $X^5$ is $(CH_2)_n$ wherein m and n are each independently 1 or 2.

In certain embodiments, $X^3$, $X^4$, and $X^5$ together is

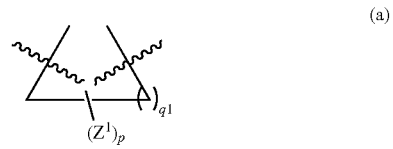

(a)

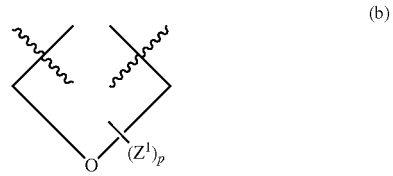

(b)

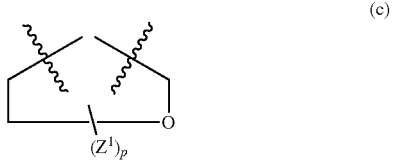

(c)

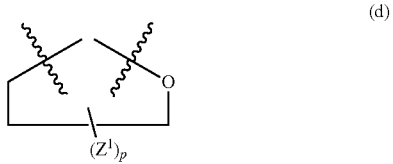

(d)

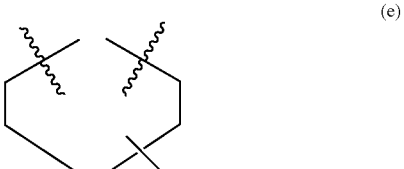

(e)

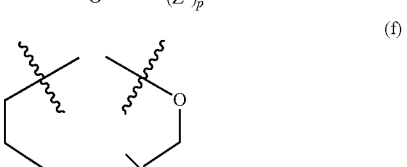

(f)

wherein q1 is 1, 2, 3, or 4, and the curvy lines represent the points of attachment.

Each $Z^1$ represents optional substituent on any substitutable carbon atom of the ring containing $X^3$, $X^4$, and $X^5$, and has values as disclosed in the Summary.

p is 0, 1, 2, 3, or 4. In certain embodiments, p is 0, 1, or 2. In other embodiments, p is 0 or 1. In yet other embodiments, p is 0. In still other embodiments, p is 1.

$G^1$ for formula (I), (I-a), (I-i), (I-i-a), (I-i-b), and (I-ii) are as described in the Summary. In certain embodiments, $G^1$ is aryl or heteroaryl, each of which is optionally substituted as described in the Summary and embodiments herein.

In certain embodiments, $G^1$ is optionally substituted heteroaryl. In certain embodiments, $G^1$ is an optionally substituted monocyclic heteroaryl. In yet other embodiments, $G^1$ is an optionally substituted bicyclic heteroaryl. Examples of $G^1$ include, but not limited thereto, pyridinyl, pyrimidinyl, thiazolyl, oxazolyl, and pyrazolyl, each of which is optionally substituted as described in the Summary and embodiments herein. In certain embodiments, $G^1$ is optionally substituted pyridinyl.

In conjunction with embodiments described herein above and below, examples of the optional substituents of the heteroaryl group of $G^1$ include, but not limited to, alkyl, halogen, and haloalkyl.

In other embodiments, $G^1$ is an optionally substituted aryl. For example, $G^1$ is phenyl substituted with an optionally substituted monocyclic heteroaryl or an optionally substituted monocyclic heterocycle, and the phenyl group is optionally further substituted with one or two groups selected from the group consisting of alkyl, alkenyl, alkynyl, halogen, haloalkyl, $N(H)_2$, $N(H)(alkyl)$, $N(alkyl)_2$, —OH, and O(alkyl).

$G^2$ for formula (I), (I-a), (I-i), (I-i-a), (I-i-b), and (I-ii) are as described in the Summary. In certain embodiments, $G^2$ is $G^{2d}$. In certain embodiments, $G^2$ is $G^{2d}$ wherein $G^{2d}$ is aryl, heteroaryl, or heterocycle, each of which is optionally substituted. In yet other embodiments, $G^2$ is $G^{2d}$ wherein $G^{2d}$ is optionally substituted aryl (e.g. optionally substituted phenyl, optionally substituted dihyroindenyl, or optionally substituted tetrahydronaphthalenyl). In yet other embodiments, $G^2$ is $G^{2d}$ wherein $G^{2d}$ is optionally substituted phenyl. In yet other embodiments, $G^2$ is $G^{2d}$ wherein $G^{2d}$ is optionally substituted heteroaryl (e.g. optionally substituted monocyclic heteroaryl such as, but not limited to, optionally substituted pyridinyl). In still other embodiments, $G^2$ is $G^{2d}$ wherein $G^{2d}$ is optionally substituted heterocycle (e.g. optionally substituted dihydrochromenyl). In certain embodiments, $G^2$ is $G^{2d}$ wherein $G^{2d}$ is optionally substituted heteroaryl (e.g. optionally substituted imidazolyl, optionally substituted pyridinyl). The optional substituents of the above mentioned $G^{2d}$ are as described in the Summary and embodiments herein.

In yet other embodiments, $G^2$ is $—(CR^{1g}R^{2g})_r-G^{2d}$ wherein $R^{1g}$, $R^{2g}$, r, and $G^{2d}$ are as described in the Summary and embodiments herein. In other embodiments, $G^2$ is $—(CR^{1g}R^{2g})-G^{2d}$ wherein $G^{2d}$ is aryl or heteroaryl, each of which is optionally substituted. In still other embodiments, $G^2$ is $—(CR^{1g}R^{2g})_r-G^{2d}$ wherein $G^{2d}$ is optionally substituted aryl (e.g. optionally substituted phenyl). In still other embodiments, $G^2$ is $—(CR^{1g}R^{2g})_r-G^{2d}$ wherein $G^{2d}$ is optionally substituted heteroaryl (e.g. optionally substituted monocyclic heteroaryl such as, but not limited to, optionally substituted pyridinyl). In conjunction with the embodiments described herein above and below, $R^{1g}$, $R^{2g}$, and r, and the optional substituents of $G^{2d}$, are as described in the Summary and herein. In certain embodiments, $R^{1g}$ and $R^{2g}$ are hydrogen. In certain embodiments, one of $R^{1g}$ and $R^{2g}$ is hydrogen, and the other is alkyl (e.g. methyl) or haloalkyl (e.g. trifluoromethyl). In yet other embodiments, one of $R^{1g}$ and $R^{2g}$ is hydrogen, and the other is alkyl (e.g. methyl). In yet other embodiments, one of $R^{1g}$ and $R^{2g}$ is hydrogen, and the other is methyl. r, for example, is 1 or 2. In certain embodiments, r is 1.

In conjunction with the above and below embodiments, examples of the optional substituents of $G^{2d}$ include, but are not limited to, alkyl (e.g. methyl), halogen (e.g. fluorine, chlorine), haloalkyl (e.g. trifluoromethyl), $—OR^f$ ($R^f$ is as described in the Summary, for example, $R^f$ is alkyl such as, but not limited to, methyl; haloalkyl such as, but not limited to, trifluoromethyl; or optionally substituted phenyl,), $—S(O)_2R^e$ ($R^e$, for example, is $C_1$-$C_4$ alkyl such as, but not limited to, methyl), $G^d$ (e.g. optionally substituted phenyl), $N(R^f)_2$ (each $R^f$, for example, is independently hydrogen, $C_1$-$C_6$ alkyl such as, but not limited to, methyl, ethyl), and $—(CR^{1a}R^{1b})_q-G^d$ (e.g. $CH_2$-phenyl). In certain embodiments, the optional substituents of $G^{2d}$ is alkyl (e.g. methyl), halogen (e.g. fluorine, chlorine), haloalkyl (e.g. trifluoromethyl), —O(alkyl), or —O(haloalkyl).

It is appreciated that the present invention contemplates compounds of formula (I), (I-a), (I-i), (I-i-a), (I-i-b), and (I-ii) with combinations of the above embodiments, including particular, more particular and preferred embodiments.

Accordingly, one aspect is directed to a group of compounds of formula (I), (I-a), (I-i), (I-i-a), (I-i-b), and (II-ii) wherein $G^1$ is aryl or heteroaryl, each of which is optionally substituted; and $G^2$ is $G^{2d}$. In certain embodiments, $G^{2d}$ is aryl, heteroaryl, or heterocycle, each of which is optionally substituted. The optional substituents of $G^1$ and $G^{2d}$ are as described in the Summary and embodiments herein above.

Another aspect is directed to a group of compounds of formula (I), (I-a), (I-i), (I-i-a), (I-i-b), and (II-ii) wherein $G^1$ is phenyl substituted with an optionally substituted monocyclic heteroaryl or an optionally substituted monocyclic heterocyle, and the phenyl group is optionally further substituted with one or two groups selected from the group consisting of alkyl, alkenyl, alkynyl, halogen, haloalkyl, $N(H)_2$, $N(H)(alkyl)$, $N(alkyl)_2$, —OH, and O(alkyl); and $G^2$ is $G^{2d}$. In certain embodiments, $G^{2d}$ is aryl, heteroaryl, or heterocycle. The optional substituents of $G^{2d}$ are as described in the Summary and embodiments herein above.

Another aspect is directed to a group of compounds of formula (I), (I-a), (I-i), (I-i-a), (I-i-b), and (II-ii) wherein $G^1$ is optionally substituted heteroaryl; and $G^2$ is $G^{2d}$. In certain embodiments, $G^{2d}$ is aryl, heteroaryl, or heterocycle, each of which is optionally substituted. The optional substituents of $G^1$ and $G^{2d}$ are as described in the Summary and embodiments herein above.

Another aspect is directed to a group of compounds of formula (I), (I-a), (I-i), (I-i-a), (I-i-b), and (II-ii) wherein $G^1$ is optionally substituted monocyclic heteroaryl (e.g. pyridinyl, pyrimidinyl, thiazolyl, oxazolyl, or pyrazolyl, each of which is optionally substituted); and $G^2$ is $G^{2d}$. In certain embodiments, $G^{2d}$ is aryl, heteroaryl, or heterocycle, each of which is optionally substituted. The optional substituents of $G^1$ and $G^{2d}$ are as described in the Summary and embodiments herein above.

Another aspect is directed to a group of compounds of formula (I), (I-a), (I-i), (I-i-a), (I-i-b), and (II-ii) wherein $G^1$ is optionally substituted pyridinyl; and $G^2$ is $G^{2d}$. In certain embodiments, $G^{2d}$ is aryl, heteroaryl, or heterocycle, each of which is optionally substituted. The optional substituents of $G^1$ and $G^{2d}$ are as described in the Summary and embodiments herein above.

Another aspect is directed to a group of compounds of formula (I), (I-a), (I-i), (I-i-a), (I-i-b), and (II-ii) wherein $G^1$ is optionally substituted pyridinyl; and $G^2$ is $G^{2d}$ wherein $G^{2d}$ is optionally substituted aryl (e.g. optionally substituted phenyl, optionally substituted dihyroindenyl, or optionally substituted tetrahydronaphthalenyl). The optional substituents of $G^1$ and $G^{2d}$ are as described in the Summary and embodiments herein above.

Another aspect is directed to a group of compounds of formula (I), (I-a), (I-i), (I-i-a), (I-i-b), and (II-ii) wherein $G^1$ is optionally substituted pyridinyl; and $G^2$ is $G^{2d}$ wherein $G^{2d}$ is optionally substituted phenyl. The optional substituents of $G^1$ and $G^{2d}$ are as described in the Summary and embodiments herein above.

Another aspect is directed to a group of compounds of formula (I), (I-a), (I-i), (I-i-a), (I-i-b), and (II-ii) wherein $G^1$ is optionally substituted pyridinyl; and $G^2$ is $G^{2d}$ wherein $G^{2d}$ is optionally substituted heteroaryl (e.g. optionally substituted imidazolyl, optionally substituted pyridinyl). The optional substituents of $G^1$ and $G^{2d}$ are as described in the Summary and embodiments herein above.

Yet another aspect is directed to a group of compounds of formula (I), (I-a), (I-i), (I-i-a), (I-i-b), and (II-ii) wherein $G^1$ is aryl or heteroaryl, each of which is optionally substituted; and $G^2$ is —$(CR^{1g}R^{2g})_r$-$G^{2d}$. In one embodiment, $G^{2d}$ is aryl or heteroaryl, each of which is optionally substituted. $R^{1g}$, $R^{2g}$, r, and the optional substituents of $G^1$ and $G^{2d}$ are as described in the Summary and embodiments herein above.

Another aspect is directed to a group of compounds of formula (I), (I-a), (I-i), (I-i-a), (I-i-b), and (II-ii) wherein $G^1$ is phenyl substituted with an optionally substituted monocyclic heteroaryl or an optionally substituted monocyclic heterocyle, and the phenyl group is optionally further substituted with one or two groups selected from the group consisting of alkyl, alkenyl, alkynyl, halogen, haloalkyl, $N(H)_2$, $N(H)$(alkyl), $N(alkyl)_2$, —OH, and O(alkyl); and $G^2$ is —$(CR^{1g}R^{2g})_r$-$G^{2d}$. In one embodiment, $G^{2d}$ is aryl or heteroaryl, each of which is optionally substituted. $R^{1g}$, $R^{2g}$, r, and the optional substituents of $G^{2d}$ are as described in the Summary and embodiments herein above.

Another aspect is directed to a group of compounds of formula (I), (I-a), (I-i), (I-i-a), (I-i-b), and (II-ii) wherein $G^1$ is optionally substituted heteroaryl; and $G^2$ is —$(CR^{1g}R^{2g})_r$-$G^{2d}$. In one embodiment, $G^{2d}$ is aryl or heteroaryl, each of which is optionally substituted. $R^{1g}$, $R^{2g}$, r, and the optional substituents of $G^1$ and $G^{2d}$ are as described in the Summary and embodiments herein above.

Another aspect is directed to a group of compounds of formula (I), (I-a), (I-i), (I-i-a), (I-i-b), and (II-ii) wherein $G^1$ is optionally substituted monocyclic heteroaryl (e.g. pyridinyl, pyrimidinyl, thiazolyl, oxazolyl, or pyrazolyl, each of which is optionally substituted); and $G^2$ is —$(CR^{1g}R^{2g})_r$-$G^{2d}$. In one embodiment, $G^{2d}$ is aryl or heteroaryl, each of which is optionally substituted. $R^{1g}$, $R^{2g}$, r, and the optional substituents of $G^1$ and $G^{2d}$ are as described in the Summary and embodiments herein above.

Another aspect is directed to a group of compounds of formula (I), (I-a), (I-i), (I-i-a), (I-i-b), and (II-ii) wherein $G^1$ is optionally substituted pyridinyl; and $G^2$ is —$(CR^{1g}R^{2g})_r$-$G^{2d}$. In one embodiment, $G^{2d}$ is aryl or heteroaryl, each of which is optionally substituted. $R^{1g}$, $R^{2g}$, r, and the optional substituents of $G^1$ and $G^{2d}$ are as described in the Summary and embodiments herein above.

Another aspect is directed to a group of compounds of formula (I), (I-a), (I-i), (I-i-a), (I-i-b), and (II-ii) wherein $G^1$ is optionally substituted pyridinyl; and $G^2$ is —$(CR^{1g}R^{2g})_r$-$G^{2d}$ wherein $G^{2d}$ is optionally substituted aryl (e.g. optionally substituted phenyl). The optional substituents of $G^1$ and $G^{2d}$, $R^{1g}$, $R^{2g}$, and r, are as described in the Summary and embodiments herein above.

Another aspect is directed to a group of compounds of formula (I), (I-a), (I-i), (I-i-a), (I-i-b), and (II-ii) wherein $G^1$ is optionally substituted pyridinyl; and $G^2$ is —$(CR^{1g}R^{2g})_r$-$G^{2d}$ wherein $G^{2d}$ optionally substituted phenyl. The optional substituents of $G^1$ and $G^{2d}$, $R^{1g}$, $R^{2g}$, and r are as described in the Summary and embodiments herein above.

Another aspect is directed to a group of compounds of formula (I), (I-a), (I-i), (I-i-a), (I-i-b), and (II-ii) wherein $G^1$ is optionally substituted pyridinyl; and $G^2$ is —$(CR^{1g}R^{2g})_r$-$G^{2d}$ wherein $G^{2d}$ is optionally substituted heteroaryl (e.g. optionally substituted monocyclic heteroaryl such as, but not limited to, optionally substituted pyridinyl). The optional substituents of $G^1$ and $G^{2d}$, $R^{1g}$, $R^{2g}$, and r are as described in the Summary and embodiments herein above.

Within each group of the compounds described above, examples of a subgroup of compounds of formula (I), (I-a), (I-i), (I-i-a), (I-i-b), and (I-ii) include, but not limited to, those wherein $X^3$ is O or $CH_2$.

Examples of another subgroup of compounds of formula (I), (I-a), (I-i), (I-i-a), (I-i-b), and (II-ii) include, but not limited to, those wherein $X^3$ is O.

Other examples of a subgroup of compounds of formula (I), (I-a), (I-i), (I-i-a), (I-i-b), and (II-ii) include, but not limited to, those wherein $X^3$ is $CH_2$.

Yet other examples of a subgroup of compounds of formula (I), (I-a), (I-i), (I-i-a), (I-i-b), and (II-ii) include, but not limited to, those wherein $X^3$ is O, $X^4$ is $(CH_2)_m$, and $X^5$ is $(CH_2)_n$ wherein m and n are each independently 1 or 2.

Yet other examples of a subgroup of compounds of formula (I), (I-a), (I-i), (I-i-a), (I-i-b), and (II-ii) include, but not limited to, those wherein $X^3$ is $CH_2$, $X^4$ is a bond or $(CH_2)_m$, $X^5$ is $(CH_2)_n$, and m and n are each independently 1 or 2.

Yet other examples of a subgroup of compounds of formula (I), (I-a), (I-i), (I-i-a), (I-i-b), and (II-ii) include, but not limited to, those wherein $X^3$ is O, one of $X^4$ and $X^5$ is a bond, and the other is $(CH_2)_3$ or $(CH_2)_4$.

Yet other examples of a subgroup of compounds of formula (I), (I-a), (I-i), (I-i-a), (I-i-b), and (II-ii) include, but not limited to, those wherein $X^3$, $X^4$, and $X^5$ together are formula (a), (b), (c), (d), (e), or (f) wherein q1 is 1, 2, 3, or 4.

Exemplary compounds include, but are not limited to:
[1-(2-fluorophenyl)cyclobutyl](pyridin-2-yl)methanol;
[1-(3-fluorophenyl)cyclobutyl](pyridin-2-yl)methanol;
[1-(4-fluorophenyl)cyclobutyl](pyridin-2-yl)methanol;
[1-(3,4-difluorophenyl)cyclobutyl](pyridin-2-yl)methanol;
pyridin-2-yl{1-[2-(trifluoromethyl)phenyl]cyclobutyl}methanol;
pyridin-2-yl{1-[3-(trifluoromethyl)phenyl]cyclobutyl}methanol;
[1-(2-methylphenyl)cyclobutyl](pyridin-2-yl)methanol;
[1-(3-methylphenyl)cyclobutyl](pyridin-2-yl)methanol;
[1-(4-methylphenyl)cyclobutyl](pyridin-2-yl)methanol;
pyridin-2-yl{1-[2-(trifluoromethoxy)phenyl]cyclobutyl}methanol;
pyridin-2-yl{1-[3-(trifluoromethoxy)phenyl]cyclobutyl}methanol;
pyridin-2-yl{1-[4-(trifluoromethoxy)phenyl]cyclobutyl}methanol;
{1-[3,5-bis(trifluoromethyl)phenyl]cyclobutyl}(pyridin-2-yl)methanol;
{1-[3-fluoro-5-(trifluoromethyl)phenyl]cyclobutyl}(pyridin-2-yl)methanol;
{1-[4-fluoro-3-(trifluoromethyl)phenyl]cyclobutyl}(pyridin-2-yl)methanol;
{1-[4-(methylsulfonyl)phenyl]cyclobutyl}(pyridin-2-yl)methanol;
{1-[3-fluoro-4-(trifluoromethyl)phenyl]cyclobutyl}(pyridin-2-yl)methanol;
{1-[4-(diethylamino)phenyl]cyclobutyl}(pyridin-2-yl)methanol;
pyridin-2-yl(1-pyridin-2-ylcyclobutyl)methanol;
pyridin-2-yl(1-pyridin-3-ylcyclobutyl)methanol;
pyridin-2-yl(1-pyridin-4-ylcyclobutyl)methanol;

[1-(1,1'-biphenyl-4-yl)cyclobutyl](pyridin-2-yl)methanol;
[1-(3-phenoxyphenyl)cyclobutyl](pyridin-2-yl)methanol;
[1-(4-phenoxyphenyl)cyclobutyl](pyridin-2-yl)methanol;
[1-(4-benzylphenyl)cyclobutyl](pyridin-2-yl)methanol;
(S)-[1-(3,4-dichlorophenyl)cyclobutyl](pyridin-2-yl)methanol;
(S)-{1-[2-fluoro-4-(trifluoromethyl)phenyl]cyclobutyl}(pyridin-2-yl)methanol;
(S)-pyridin-2-yl{1-[4-(trifluoromethyl)phenyl]cyclobutyl}methanol;
(S)-{1-[3-fluoro-4-(trifluoromethyl)phenyl]cyclobutyl}(pyridin-2-yl)methanol;
(S)-[1-(3,4-dichlorophenyl)cyclobutyl](3-methylpyridin-2-yl)methanol;
pyrimidin-2-yl{1-[4-(trifluoromethoxy)phenyl]cyclobutyl}methanol;
[1-(2-fluorophenyl)cyclobutyl](pyrimidin-2-yl)methanol;
[1-(3-fluorophenyl)cyclobutyl](pyrimidin-2-yl)methanol;
[1-(4-fluorophenyl)cyclobutyl](pyrimidin-2-yl)methanol;
[1-(3,4-difluorophenyl)cyclobutyl](pyrimidin-2-yl)methanol;
pyrimidin-2-yl{1-[2-(trifluoromethoxy)phenyl]cyclobutyl}methanol;
pyrimidin-2-yl{1-[3-(trifluoromethoxy)phenyl]cyclobutyl}methanol;
[1-(3,4-dichlorophenyl)cyclobutyl](pyrimidin-2-yl)methanol;
(S)-[1-(3,4-dichlorophenyl)cyclobutyl](pyrimidin-2-yl)methanol;
(R)-[1-(3,4-dichlorophenyl)cyclobutyl](pyrimidin-2-yl)methanol;
(S)-pyrimidin-2-yl{1-[4-(trifluoromethyl)phenyl]cyclobutyl}methanol;
(R)-pyrimidin-2-yl{1-[4-(trifluoromethyl)phenyl]cyclobutyl}methanol;
[1-(3,4-dichlorophenyl)cyclohexyl](pyridin-2-yl)methanol;
{1-[1-(3-chlorophenyl)ethyl]cyclobutyl}(pyridin-2-yl)methanol;
{1-[1-(2-methylphenyl)ethyl]cyclobutyl}(pyridin-2-yl)methanol;
{1-[1-(4-fluorophenyl)ethyl]cyclobutyl}(pyridin-2-yl)methanol;
{1-[1-(3-fluorophenyl)ethyl]cyclobutyl}(pyridin-2-yl)methanol;
{1-[1-(2-fluorophenyl)ethyl]cyclobutyl}(pyridin-2-yl)methanol;
{1-[1-(4-chlorophenyl)ethyl]cyclobutyl}(pyridin-2-yl)methanol;
{1-[1-(2-chlorophenyl)ethyl]cyclobutyl}(pyridin-2-yl)methanol;
[1-(1-phenylethyl)cyclobutyl](pyridin-2-yl)methanol;
[1-(4-methylbenzyl)cyclobutyl](pyridin-2-yl)methanol;
3-{3-[(5-fluoro-1-naphthyl)oxy]propyl}-7-[(2-methoxypyridin-3-yl)amino]-1-(2-morpholin-4-ylethyl)-1H-indole-2-carboxylic acid;
pyridin-2-yl(1-{1-[3-(trifluoromethyl)phenyl]ethyl}cyclobutyl)methanol;
[1-(2,3-dihydro-1H-inden-1-yl)cyclobutyl](pyridin-2-yl)methanol; pyridin-2-yl[1-(1,2,3,4-tetrahydronaphthalen-1-yl)cyclobutyl]methanol;
[1-(3,4-dihydro-2H-chromen-4-yl)cyclobutyl](pyridin-2-yl)methanol;
pyridin-2-yl[1-(2,2,2-trifluoro-1-phenylethyl)cyclobutyl]methanol;
[4-(3,4-dichlorophenyl)tetrahydro-2H-pyran-4-yl](pyridin-2-yl)methanol;
(4-phenyltetrahydro-2H-pyran-4-yl)(pyridin-2-yl)methanol;
[4-(3-fluorophenyl)tetrahydro-2H-pyran-4-yl](pyridin-2-yl)methanol;
[4-(4-fluorophenyl)tetrahydro-2H-pyran-4-yl](pyridin-2-yl)methanol;
[4-(3,4-difluorophenyl)tetrahydro-2H-pyran-4-yl](pyridin-2-yl)methanol;
[4-(4-chlorophenyl)tetrahydro-2H-pyran-4-yl](pyridin-2-yl)methanol;
pyridin-2-yl {4-[4-(trifluoromethyl)phenyl]tetrahydro-2H-pyran-4-yl}methanol;
pyridin-2-yl {4-[3-(trifluoromethoxy)phenyl]tetrahydro-2H-pyran-4-yl}methanol;
pyridin-2-yl {4-[4-(trifluoromethoxy)phenyl]tetrahydro-2H-pyran-4-yl}methanol;
2-(1-phenylcyclobutyl)-1-(pyridin-2-yl)ethanol;
2-[1-(4-chlorophenyl)cyclobutyl]-1-(pyridin-2-yl)ethanol;
2-[1-(4-fluorophenyl)cyclobutyl]-1-(pyridin-2-yl)ethanol;
2-[1-(3-fluorophenyl)cyclobutyl]-1-(pyridin-2-yl)ethanol;
2-[1-(3-chlorophenyl)cyclobutyl]-1-(pyridin-2-yl)ethanol;
2-[1-(3,4-dichlorophenyl)cyclobutyl]-1-(pyridin-2-yl)ethanol;
1-(pyridin-2-yl)-2-{1-[3-(trifluoromethyl)phenyl]cyclobutyl}ethanol;
1-(pyridin-2-yl)-2-{1-[4-(trifluoromethyl)phenyl]cyclobutyl}ethanol;
1-(pyridin-2-yl)-2-{1-[4-(trifluoromethoxy)phenyl]cyclobutyl}ethanol;
1-(pyridin-2-yl)-2-{1-[3-(trifluoromethoxy)phenyl]cyclobutyl}ethanol;
(Z)-1-[1-(3,4-dichlorophenyl)cyclobutyl]-N-hydroxy-1-(pyridin-2-yl)methanimine; and
(S)-[1-(3,4-dichlorophenyl)cyclopropyl](pyridin-2-yl)methanol.

The present compounds may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

Various stereoisomers of the present compounds and mixtures thereof are included within the scope of this application. Stereoisomers include enantiomers and diastereomers, and mixtures of enantiomers or diastereomers. Individual stereoisomers may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers may exist in the present compounds. Various geometric isomers and mixtures thereof resulting from the disposition of substituents around a carbon-carbon double bond, a carbon-nitrogen double bond, a cycloalkyl group, or a heterocycle group are contemplated. Substituents around a carbon-carbon double bond or a carbon-nitrogen bond are designated as being of Z or E configuration and substituents around a cycloalkyl or a heterocycle are designated as being of cis or trans configuration.

Compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^2$H, $^3$H, $^{13}$C, $^{14}$C, $^{15}$N, $^{18}$O, $^{32}$P, $^{35}$S, $^{18}$F, $^{36}$Cl, and $^{125}$I. Compounds that contain other isotopes of these and/or other atoms are within the scope of this invention.

In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7531685; 7528131; 7521421; 7514068; 7511013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of TRPV3 modulators in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., *Advances in Drug Research Vol.* 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999).

In addition, non-radio active isotope containing drugs, such as deuterated drugs called "heavy drugs," can be used for the treatment of diseases and conditions related to TRPV3 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug may alter its physicochemical properties such as pKa and lipid solubility. These effects and alterations may affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmcokinetic profile or efficacy relative to the non-isotopic compound.

C. BIOLOGICAL DATA (i) In Vitro Methods-Calcium Flux Assays:

Experiments were conducted using the FLIPR$^{TETRA}$®. On the day prior to the experiment, recombinant HEK293 cells that stably express human and mouse TRPV3 were removed from tissue culture flasks and plated in growth medium at 20,000 cells/well into black-walled clear-bottom 384-well Biocoat™ poly-D-lysine assay plates (BD Biosciences, Bedford, Mass.) using a Multidrop® dispenser (ThermoScientific, Waltham, Mass.). On the day of the experiment, growth medium was removed, and the no-wash FLIPR® Calcium-4 dye ($\lambda_{EX}$=470-495 nm, $\lambda_{EM}$=515-575 nm; Molecular Devices, Sunnyvale, Calif.) was added to each well using the Multidrop® dispenser. Cells were incubated for 90-120 minutes in the dark. Compounds were dissolved in DMSO to prepare a 10 mM stock solution. The intensity of the fluorescence was captured and digitally transferred to an interfaced PC. The peak increase in fluorescence over baseline (relative fluorescence units) was calculated and expressed as the percentage of the maximal 2-APB (2-aminoethoxyldiphenyl borate) response (in the absence of compound). The concentration of 2-APB corresponds to its $EC_{50}$. $IC_{50}$ of the compounds for human TRPV3 are shown in Table 1 wherein "A" refers to an $IC_{50}$ value of greater than 20 μM, "B" refers to an $IC_{50}$ value in range of 5.1 μM to 20 μM, "C" refers to an $IC_{50}$ value in range of 1.1 μM to 5 μM, "D" refers to an $IC_{50}$ value in range of 501 nM to 1,000 nM, "E" refers to an $IC_{50}$ value in range of 50 nM to 500 nM.

TABLE 1

| Example # | $IC_{50}$ (μM) |
| --- | --- |
| 1 | C |
| 2 | E |
| 3 | D |
| 4 | E |
| 5 | B |

TABLE 1-continued

| Example # | IC$_{50}$ (µM) |
|---|---|
| 6 | E |
| 7 | B |
| 8 | E |
| 9 | C |
| 10 | C |
| 11 | E |
| 12 | E |
| 13 | D |
| 14 | B |
| 15 | E |
| 16 | B |
| 17 | C |
| 18 | D |
| 19 | B |
| 20 | B |
| 21 | B |
| 22 | B |
| 23 | D |
| 24 | C |
| 25 | C |
| 26 | E |
| 27 | D |
| 28 | E |
| 29 | C |
| 30 | C |
| 31 | C |
| 32 | B |
| 33 | B |
| 34 | B |
| 35 | B |
| 36 | B |
| 37 | D |
| 38 | E |
| 39 | D |
| 40 | B |
| 41 | B |
| 42 | C |
| 43 | E |
| 44 | B |
| 45 | C |
| 46 | B |
| 47 | C |
| 48 | B |
| 49 | C |
| 50 | C |
| 51 | B |
| 52 | C |
| 53 | C |
| 54 | B |
| 55 | B |
| 56 | C |
| 57 | B |
| 58 | C |
| 59 | C |
| 60 | B |
| 61 | B |
| 62 | B |
| 63 | B |
| 64 | C |
| 65 | C |
| 66 | C |
| 67 | C |
| 68 | C |
| 69 | C |
| 70 | B |
| 71 | C |
| 72 | C |
| 73 | C |
| 74 | E |
| 75 | D |
| 76 | D |
| 77 | D |

(ii) In Vivo Data Animals

Adult male Sprague-Dawley rats (250-300 g body weight, Charles River Laboratories, Portage, Mich.) were used. Animal handling and experimental protocols were approved by the Institutional Animal Care and Use Committee (IACUC) at Abbott Laboratories. For all surgical procedures, animals were maintained under isoflurane anesthesia (4-5% to induce, 1-3% to maintain), and the incision sites were sterilized using a 10% povidone-iodine solution prior to and after surgeries.

Sodium Iodoacetate-Induced Knee Joint Osteoarthritic Pain Model

Unilateral knee joint osteoarthritis was induced in the rats by a single intra-articular (i.a.) injection of sodium iodoacetate (3 mg in 0.05 mL sterile isotonic saline) into the right knee joint cavity under light isoflurane anesthesia using a 26 G needle. The dose of the sodium iodoacetate (3 mg/i.a. injection) was selected based on results obtained from preliminary studies wherein an optimal pain behavior was observed at this dose. Pain behavioral assessment of hind limb grip force was conducted by recording the maximum compressive force exerted on the hind limb strain gauge setup, in a commercially available grip force measurement system (Columbus Instruments, Columbus, Ohio). The grip force data was converted to a maximum hindlimb cumulative compressive force (CFmax) (gram force)/kg body weight for each animal. The analgesic effects of test compounds were determined 20 days following the i.a. injection of sodium iodoacetate. The vehicle control group for each compound being tested was assigned 0% whereas the age matched naïve group was assigned as being 100% (normal). The % effect for each dose group was then expressed as % return to normalcy compared to the naïve group. Compounds were administered either intraperitoneally (i.p.) or orally (p.o.). The assessment of the analgesic effects of test compounds is typically made anytime between about 1 hour and about 5 hours following oral administration. The assessment of the analgesic effects of test compounds is typically made anytime between about 0.5 hour and about 2 hours following i.p. administration. Selection of the preferred time points for measuring the analgesic effects of test compounds was based upon consideration of the individual pharmacokinetic characteristics of test compounds in the rat. Time points that were known or expected to provide higher plasma concentrations of test compounds were preferred over those that were known or expected to provide lower concentrations.

Compounds tested showed a statistically significant change in hind limb grip force strength versus a saline vehicle at less than about 300 µmol/kg in the sodium iodoacetate-induced model of osteoarthritic pain following a single dose, for example, at less than about 50 µmol/kg in the sodium iodoacetate-induced model of osteoarthritic pain following a single dose.

D. METHODS OF USING THE COMPOUNDS

Data in Table 1 demonstrates that present compounds are modulators of TRPV3 receptors, and thus are useful in the treatment of diseases, conditions, and/or disorders modulated by TRPV3. The relationship between therapeutic effect and inhibition of TRPV3 has been shown in WO2007/056124; Wissenbach, U. et al., Biology of the cell (2004), 96, 47-54; Nilius, B. et al., Physiol Rev (2007), 87, 165-217; Okuhara, D. Y. et al., Expert Opinion on Therapeutic Targets (2007), 11, 391-401; Hu, H. Z. et al., *Journal of Cellular Physiology* (2006), 208, 201-212.

One embodiment is therefore directed to a method for treating a disease, condition, and/or disorder modulated by TRPV3 in a subject in need thereof, said method comprises administering to the subject a therapeutically effective amount of a compound, or pharmaceutically acceptable salt, solvate, salt of a solvate or solvate of a salt thereof, with or without a pharmaceutically acceptable carrier.

Diseases, conditions, and/or disorders that are modulated by TRPV3 include, but are not limited to, migraine, arthralgia, cardiac pain arising from an ischemic myocardium, acute pain, chronic pain, nociceptive pain, neuropathic pain, post-operative pain, pain due to neuralgia (e.g., post-herpetic neuralgia, traumatic neuralgia, fibromyalgia, trigeminal neuralgia), pain due to diabetic neuropathy, dental pain and cancer pain, inflammatory pain conditions (e.g. arthritis and osteoarthritis).

Diseases, conditions, and/or disorders that are modulated by TRPV3 also include, but are not limited to, pain such as neuropathic pain, nociceptive pain, dental pain, HIV pain, cardiac pain arising from an ischemic myocardium, pain due to migraine, arthralgia, neuropathies, neurodegeneration, retinopathy, neurotic skin disorder, stroke, urinary bladder hypersensitiveness, urinary incontinence, vulvodynia, gastrointestinal disorders such as irritable bowel syndrome, gastro-esophageal reflux disease, enteritis, ileitis, stomach-duodenal ulcer, inflammatory bowel disease, Crohn's disease, celiac disease, an inflammatory disease such as pancreatitis, a respiratory disorder such as allergic and non-allergic rhinitis, asthma or chronic obstructive pulmonary disease, irritation of skin, eye or mucous membrane, dermatitis, pruritic conditions such as uremic pruritus, fervescence, muscle spasms, emesis, dyskinesias, depression, Huntington's disease, memory deficits, restricted brain function, amyotrophic lateral sclerosis (ALS), dementia, arthritis, osteoarthritis, diabetes, obesity, urticaria, actinic keratosis, keratocanthoma, alopecia, Meniere's disease, tinnitus, hyperacusis, anxiety disorders and benign prostate hyperplasia.

One embodiment provides methods for treating pain (for example, migraine, inflammatory pain, acute pain, chronic pain, neuropathic pain, nociceptive pain, arthritic pain, osteoarthritic pain, post-operative pain, cancer pain, lower back pain, eye pain) in a subject (including human) in need of such treatment. The methods comprise administering to the subject therapeutically effective amount of a compound as described herein, or a pharmaceutically acceptable salt, solvate, salt of a solvate, or solvate of a salt thereof, alone or in combination with a pharmaceutically acceptable carrier. The method further comprises administration of the present compound as a single dose. The method also comprises repeated or chronic administration of the present compound over a period of days, weeks, months, or longer. In certain embodiments, the method comprises administering to the subject a therapeutically effective amount of any of the compounds as described herein, or a pharmaceutically acceptable salt, solvate, salt of a solvate, or solvate of a salt thereof, in combination with a nonsteroidal anti-inflammatory drugs (NSAIDs), or other analgesic (for example, acetaminophen, opioids such as morphine or other related opioids), or combinations thereof.

Another embodiment provides method for increasing the therapeutic effectiveness or potency of compounds described herein by repeated or chronic administration over a period of days, weeks, or months.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level will depend upon the activity of the particular compound, the route of administration, the duration of treatment, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved. In the treatment of certain medical conditions, repeated or chronic administration of the compounds may be required to achieve the desired therapeutic response. "Repeated or chronic administration" refers to the administration of the compounds daily (i.e., every day) or intermittently (i.e., not every day) over a period of days, weeks, months, or longer. In particular, the treatment of chronic painful conditions is anticipated to require such repeated or chronic administration of compounds described herein. The compounds may become more effective upon repeated or chronic administration such that the therapeutically effective doses on repeated or chronic administration may be lower than the therapeutically effective dose from a single administration.

Compounds can also be administered as a pharmaceutical composition comprising the compounds of interest, or pharmaceutically acceptable salts, solvates, or salts of solvates thereof, in combination with one or more pharmaceutically acceptable carriers. The phrase "therapeutically effective amount" of a compound means a sufficient amount of the compound to treat disorders, at a reasonable benefit/risk ratio applicable to any medical treatment. It will be understood, however, that the total daily usage of the compounds and compositions will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The compounds may be administered alone, or in combination with one or more other compounds described herein, or in combination (i.e. co-administered) with one or more additional pharmaceutical agents. For example, one or more compounds, or pharmaceutically acceptable salts, solvates, salts of solvates, or solvates of salts thereof, may be administered in combination with one or more analgesic (e.g. acetaminophen, opioid such as morphine), or with one or more nonsteroidal anti-inflammatory drugs (NSAIDs), or combinations thereof. Non-limiting examples of NSAIDs include, but not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. Combination therapy includes administration of a single pharmaceutical dosage formulation containing one or more of the compounds and one or more additional pharmaceutical agents, as well as administration of the compounds and each additional pharmaceutical agent, in its own separate pharmaceutical dosage formulation. For example, one or more compounds described herein and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, the compounds and one or more additional pharmaceutical agents may be administered at essentially the same time (e.g., concurrently) or at separately staggered times (e.g., sequentially).

The total daily dose of the compounds administered to a human or other animal range from about 0.01 mg/kg body weight to about 100 mg/kg body weight, for example, in the range of from about 0.03 mg/kg body weight to about 30 mg/kg body weight. If desired, the effective daily dose can be divided into multiple doses for purposes of administration. Consequently, single dose compositions may contain such amounts or submultiples thereof to make up the daily dose. It is understood that the effective daily dose may vary with the duration of the treatment.

E. PHARMACEUTICAL COMPOSITIONS

Further provided herein is a pharmaceutical composition that comprises a compound or a pharmaceutically acceptable salt, solvate, salt of a solvate, or solvate of a salt thereof, formulated together with a pharmaceutically acceptable carrier.

Another aspect provides pharmaceutical composition comprising a compound or a pharmaceutically acceptable salt, solvate, salt of a solvate, or solvate of a salt thereof, in combination with an analgesic (e.g. acetaminophen or opioid such as morphine or other related opioids), or in combination with a nonsteroidal anti-inflammatory drugs (NSAIDs), or a combination thereof, formulated together with a pharmaceutically acceptable carrier.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

The present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of the compounds by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The compounds can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

F. GENERAL SYNTHESIS

Compounds described herein when prepared by synthetic processes or by metabolic processes are encompassed within the scope of this application. Preparation of the compounds by metabolic processes includes those occurring in the human or animal body (in vivo) or processes occurring in vitro.

The compounds can be prepared by a variety of processes well known for the preparation of compounds of this class. For example, the compounds described herein wherein the groups $G^1, X^1, X^2, X^3, X^4, X^5, G^2, G^{2d}, R^{10}, R^{1g}, R^a, R^b$, u, p, and $Z^1$ have the meanings as set forth in the summary section unless otherwise noted, can be synthesized as shown in Schemes 1-5.

Abbreviations which have been used in the descriptions of the Schemes and the Examples that follow are: DMSO for dimethyl sulfoxide, EtOAc for ethyl acetate, HATU for O-(7-azabenzotriazol-1-yl)-N,N,N',N'-tetramethyluronium hexafluorophosphate, HMDS for hexamethyl disilylazide, IPA of isopropanol, MTBE for methyl tert-butyl ether, n-BuLi for n-butyl lithium, prep-TLC for preparatory thick layer chromatography, SFC for supercritical fluid chromatography, and THF for tetrahydrofuran.

Compounds of formula (I) wherein u is 0 can be prepared using general procedures as illustrated in Scheme 1.

Reduction of nitriles of formula (1) with a reducing agent such as, but not limited to, diisobutylaluminum hydride, at a temperature of about −78° C., and in a solvent such as, but not limited to, dichloromethane, produces aldehydes of formula (2). Treatment of the aldehydes (2) with trialkylstannyl of formula (3) in the presence of n-butyllithium and in a solvent such as, but not limited to, tetrahydrofuran, provides alcohols of formula (4). The reaction is generally conducted at low temperature, such as at about −78° C. to about −100° C.

Alternatively, compounds of formula (4) can be prepared from the nitriles of formula (1) by (a) treatment with a bromide of formula $G^1$-Br in the presence of n-butyllithium and at about −78° C.; and (b) treating the intermediate from step (a) with sulfuric acid at about 40 to about 60° C.; to provide ketones of formula (5); and subsequently reducing the ketones with a reducing agent such as, but not limited to, sodium borohydride at about room temperature, in a solvent such as, but not limited to, methanol.

Chiral alcohols of formula (4a) and (4b) can be obtained by separation of the enantiomers using chiral columns or by chiral reduction of the ketones of formula (5), for example, by reducing (5) in the presence of a chiral agent such as, but not limited to, (S,S)—N-(p-touenesulfonyl)-1,2-diphenylethanediamine(chloro)(p-cumene)ruthenium (II), and a hydrogen source such as, but not limited to, formic acid, ammonium formate, or gaseous hydrogen.

Oximes of formula (6) can be prepared by treatment of the ketones (5) with compounds of formula $H_2NOR^{10}$ using reaction conditions that are known to one skilled in the art.

Nitriles of formula (I) may be purchased or prepared using general procedures known in the art such as those illustrated in Scheme 2:

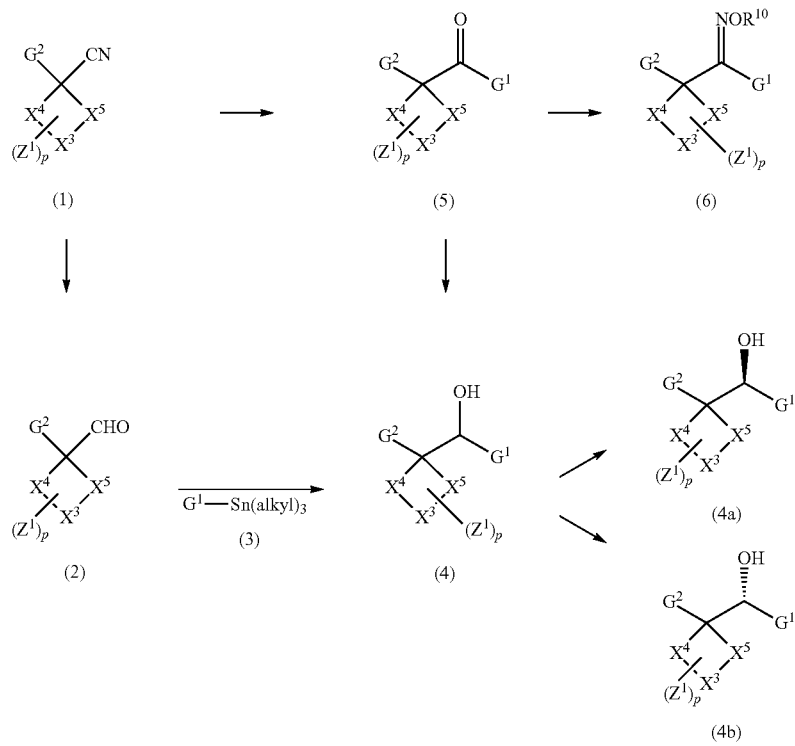

Scheme 2

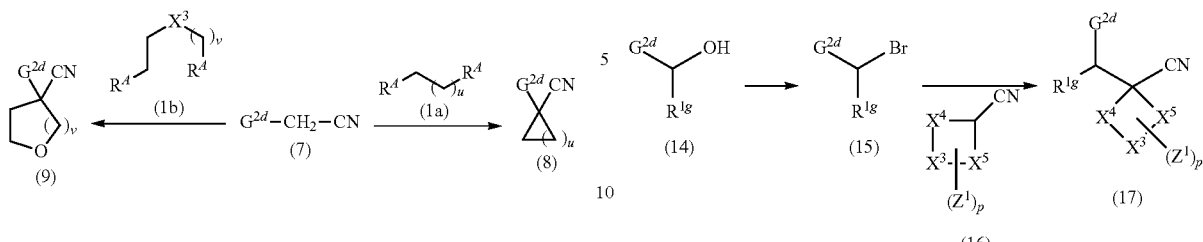

Nitriles of formula (7) can be treated with compounds of formula (1a) wherein u is 1, 2, 3, 4, 5, or 6, or formula (1b) wherein v is 1 or 2, and each $R^A$ in formula (1a) and (1b) is the same or different, and is chloro, bromo, mesylate, or tosylate, to provide nitriles of formula (8) and (9) respectively. The reaction is generally conducted in the presence of a base such as, but not limited to, sodium hydride, and in an aprotic solvent such as, but not limited to, DMSO, and at a temperature ranging from about 0° C. to about 50° C., typically at about room temperature. Alternatively, the conversion can be achieved utilizing lithium diisopropyl amide as a base, and at a temperature of about –78° C.

Scheme 3 further illustrates synthetic methods for the preparation of the intermediate nitriles used in Scheme 1.

Scheme 3

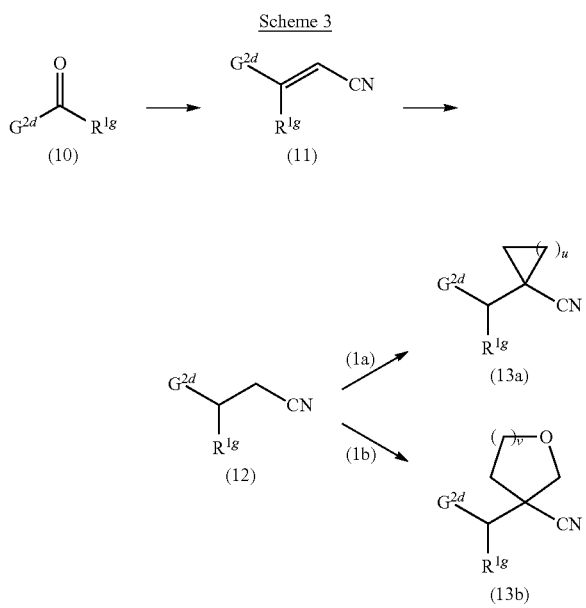

Reaction of ketones of formula (10) with diethyl cyanomethylphosphonate in the presence of a base such as, but not limited to, sodium hydride at about room temperature provides alkenes of formula (11). Reduction of the alkenes to compounds of formula (12) can be accomplished by hydrogenation in the presence of Pd/C catalyst. Alternatively, the reduction reaction can be conducted in the presence of a reducing agent such as, but not limited to, sodium borohydride, in methanol, at about room temperature. Treatment of compounds of formula (12) with (1a) or (1b) utilizing conditions as described in Scheme 1 provide the intermediate nitrile of formula (13a) or (13b) respectively.

Scheme 4

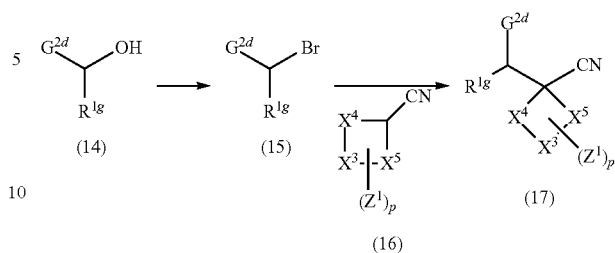

Nitriles of formula (17) can be prepared from alcohols of formula (14) via a two-step reactions. The alcohols are first treated with tribromophosphine at about room temperature, followed by the reaction of the resulting bromides of formula (15) with nitriles of formula (16) in the presence of lithium diisopropyl amide at about –78° C.

Compounds of formula (I) wherein u is 0, $X^1$ is OH, $X^2$ is hydrogen, $X^3$ is O, $X^4$ and $X^5$ are $CH_2$, and $G^2$ is $G^{2d}$ can be prepared using general procedure as shown in Scheme 5.

Scheme 5

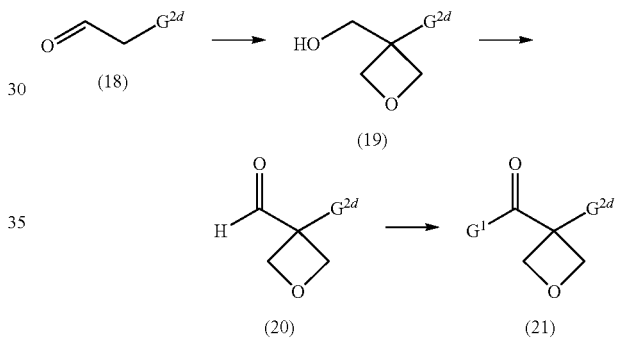

Aldehydes of formula (18) can be treated with paraformaldehyde and calcium hydroxide to form oxenatyl alcohols of formula (19). Swern oxidation of (19) provides aldehydes of formula (20). Treatment of (20) with bromides of formula $G^1$-Br in the presence of n-butyllithium provides compounds of formula (21).

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

EXAMPLES

Generally, LCMS measurement were run on Agilent 1200 HPLC/6100 SQ System using the follow condition: Mobile Phase: A: Water (0.05% TFA) B: Acetonitrile (0.05% TFA); Gradient Phase: 5%-95% in 1.3 min; Flow rate: 1.6 mL/min; Column: XBridge, 2.5 min; Oven temp: 50° C.

Example 1

[1-(2-fluorophenyl)cyclobutyl](pyridin-2-yl)methanol

Example 1A 1-(2-fluorophenyl)cyclobutanecarbonitrile

Sodium hydride (0.317 g, 13.2 mmol) was slowly added to DMSO (40 mL) at 0° C., and the mixture was warmed to ambient temperature. After stirring for 10 minutes, a solution of 2-(2-fluorophenyl)acetonitrile (0.702 g, 6.0 mmol) and 1,3-dibromopropane (1.206 g, 6.0 mmol) in diethyl ether (20 mL) was added over 30 min at <30° C. Additional 10 mL of DMSO was added to ease the stirring. The mixture was stirred overnight at room temperature and then diluted with 25 mL of ether and 15 mL of water. The organic layer was separated and washed with water and brine. After drying ($Na_2SO_4$), filtering, and concentrating, the residue was purified by column chromatography on silica gel (petroleum ether: EtOAc=10:1) to give Example 1A (0.5 g, 3.18 mmol, 53% yield). LC-MS: m/z 176 (M+H).

Example 1B (1-(2-fluorophenyl)cyclobutyl)(pyridin-2-yl)methanone

To a solution of 2-bromopyridine (0.474 g, 3.0 mmol) in dry THF was added n-BuLi (1.2 mL, 2.5 M solution in n-hexane) at −78° C. After stirring for 15 minutes, the solution of Example 1A (0.35 g, 2 mmol) in THF (2 mL) was added. The mixture was stirred at −78° C. for 15 min and 2 mL of 1 M $H_2SO_4$ solution was added slowly. The mixture was heated to 50°-60° C. for 30 minutes. The aqueous phase was separated and extracted with EtOAc. The combined organic phases were washed with water, brine, dried over $Na_2SO_4$, and filtered. After concentration in vacuo, the crude product was purified by column chromatography on silica gel (petroleum ether: EtOAc=10:1) to give the desired Example 1B (0.33 g, 1.29 mol, 64.7% yield). LC-MS: m/z 256 (M+H).

Example 1C

[1-(2-fluorophenyl)cyclobutyl](pyridin-2-yl)methanol

To solution of Example 1B (0.1 g, 0.392 mmol) in methanol was added $NaBH_4$ (0.045 g, 1.176 mmol) in portions, and the mixture was stirred overnight at room temperature. After removal of the solvent, the pH of the remainder was adjusted to 7-8 by addition of 1 N HCl and then extracted with EtOAc. The organic phase was dried over $Na_2SO_4$, and filtered. After concentration in vacuo the residue was purified by prep-TLC (petroleum ether: EtOAc=10:1) to give Example 1C (43.1 mg, 0.168 mmol, 42.8% yield). LC-MS: m/z 258 (M+H); $^1$H-NMR (400 MHz, DMSO-$d_6$): δ ppm 8.37 (d, J=4.8 Hz, 1H), 7.58-7.53 (m, 1H), 7.19-7.12 (m, 1H), 7.00-6.96 (m, 2H), 6.91-6.87 (m, 2H), 6.83-6.79 (m, 1H), 5.55 (d, J=4.8 Hz, 1H), 4.93 (d, J=4.8 Hz, 1H), 2.76-2.69 (m, 2H), 2.27-2.21 (m, 2H), 1.84-1.79 (m, 1H), 1.73-1.70 (m, 1H).

Example 2

[1-(3-fluorophenyl)cyclobutyl](pyridin-2-yl)methanol

Example 2A 1-(3-fluorophenyl)cyclobutanecarbonitrile

The title compound was prepared according to the procedure of Example 1A, substituting 2-(3-fluorophenyl)acetonitrile for 2-(2-fluorophenyl)acetonitrile. LC-MS: m/z 176 (M+H).

Example 2B (1-(3-fluorophenyl)cyclobutyl)(pyridin-2-yl)methanone

The title compound was prepared according to the procedure of Example 1B, substituting Example 2A for Example 1A. LC-MS: m/z 256 (M+H).

Example 2C

[1-(3-fluorophenyl)cyclobutyl](pyridin-2-yl)methanol

The title compound was prepared according to the procedure of Example 1C, substituting Example 2B for Example 1B. LC-MS: m/z 258 (M+H); $^1$H-NMR (400 MHz, DMSO-$d_6$): δ ppm 8.40 (d, J=4.8 Hz, 1H), 7.53-7.49 (m, 1H), 7.18-7.11 (m, 2H), 6.92-6.87 (m, 1H), 6.74-6.72 (m, 1H), 6.58-6.52 (m, 2H), 5.60 (d, J=4.8 Hz, 1H), 4.90 (d, J=4.8 Hz, 1H), 2.79-2.66 (m, 2H), 2.25-2.10 (m, 2H), 1.93-1.86 (m, 1H), 1.75-1.67 (m, 1H).

Example 3

[1-(4-fluorophenyl)cyclobutyl](pyridin-2-yl)methanol

Example 3A 1-(4-fluorophenyl)cyclobutanecarbonitrile

The title compound was prepared according to the procedure of Example 1A, substituting 2-(4-fluorophenyl)acetonitrile for 2-(2-fluorophenyl)acetonitrile. LC-MS: m/z 176 (M+H).

Example 3B (1-(4-fluorophenyl)cyclobutyl)(pyridin-2-yl)methanone

The title compound was prepared according to the procedure of Example 1B, substituting Example 3A for Example 1A. LC-MS: m/z 256 (M+H).

Example 3C

[1-(4-fluorophenyl)cyclobutyl](pyridin-2-yl)methanol

The title compound was prepared according to the procedure of Example 1C, substituting Example 3B for Example 1B. LC-MS: m/z 258 (M+H); $^1$H-NMR (400 MHz, DMSO-$d_6$): δ ppm 8.40 (d, J=4.8 Hz, 1H), 7.52-8.48 (m, 1H), 7.17-7.14 (m, 2H), 6.95-6.91 (m, 2H), 6.78-6.74 (m, 2H), 6.68 (d, J=8 Hz, 1H), 5.55 (d, J=4.8 Hz, 1H), 4.90 (d, J=4.8 Hz, 1H), 2.76-2.66 (m, 2H), 2.15-2.10 (m, 2H), 1.92-1.89 (m, 1H), 1.73-1.69 (m, 1H).

Example 4

[1-(3,4-difluorophenyl)cyclobutyl](pyridin-2-yl)methanol

Example 4A 1-(3,4-difluorophenyl)cyclobutanecarbonitrile

The title compound was prepared according to the procedure of Example 1A, substituting 2-(3,4-difluorophenyl)acetonitrile for 2-(2-fluorophenyl)acetonitrile. LC-MS: m/z 194 (M+H).

Example 4B (1-(3,4-difluorophenyl)cyclobutyl)(pyridin-2-yl)methanone

The title compound was prepared according to the procedure of Example 1B, substituting Example 4A for Example 1A. LC-MS: m/z 274 (M+H).

Example 4C

[1-(3,4-difluorophenyl)cyclobutyl](pyridin-2-yl)methanol

The title compound was prepared according to the procedure of Example 1C, substituting Example 4B for Example 1B. LC-MS: m/z 276 (M+H); $^1$H-NMR (400 MHz, DMSO-$d_6$): δ ppm 8.41 (d, J=4.8 Hz, 1H), 7.50-7.46 (m, 2H), 7.39-7.35 (m, 1H), 7.13 (d, J=7.6 Hz, 1H), 6.88-6.87 (m, 1H), 6.63 (d, J=7.6 Hz, 1H), 5.66 (d, J=4.4 Hz, 1H), 4.96 (d, J=4.8 Hz, 1H), 2.85-2.70 (m, 2H), 2.30-2.20 (m, 2H), 1.99-1.92 (m, 1H), 1.78-1.72 (m, 1H).

Example 5 pyridin-2-yl{1-[2-(trifluoromethyl)phenyl]cyclobutyl}methanol

Example 5A 1-(2-(trifluoromethyl)phenyl)cyclobutanecarbonitrile

The title compound was prepared according to the procedure of Example 1A, substituting 2-(2-(trifluoromethyl)phenyl)acetonitrile for 2-(2-fluorophenyl)acetonitrile. LC-MS: m/z 226 (M+H).

Example 5B pyridin-2-yl(1-(2-(trifluoromethyl)phenyl)cyclobutyl)methanone

The title compound was prepared according to the procedure of Example 1B, substituting Example 5A for Example 1A. LC-MS: m/z 306 (M+H).

Example 5C pyridin-2-yl{1-[2-(trifluoromethyl)phenyl]cyclobutyl}methanol

The title compound was prepared according to the procedure of Example 1C, substituting Example 5B for Example 1B. LC-MS: m/z 308 (M+H); $^1$H-NMR (400 MHz, CD$_3$OD): δ ppm 8.28-8.27 (m, 1H), 7.66-7.47 (m, 2H), 7.21-7.17 (m, 2H), 7.12-7.11 (m, 1H), 6.80-6.79 (m, 2H), 4.96 (s, 1H), 2.88-2.68 (m, 2H), 2.44-2.36 (m, 1H), 2.29-2.23 (m, 1H), 1.53-1.52 (m, 2H).

Example 6 pyridin-2-yl{1-[3-(trifluoromethyl)phenyl]cyclobutyl}methanol

Example 6A 1-(3-(trifluoromethyl)phenyl)cyclobutanecarbonitrile

The title compound was prepared according to the procedure of Example 1A, substituting 2-(3-(trifluoromethyl)phenyl)acetonitrile for 2-(2-fluorophenyl)acetonitrile. LC-MS: m/z 226 (M+H).

Example 6B pyridin-2-yl(1-(3-(trifluoromethyl)phenyl)cyclobutyl)methanone

The title compound was prepared according to the procedure of Example 1B, substituting Example 6A for Example 1A. LC-MS: m/z 306 (M+H).

Example 6C pyridin-2-yl{1-[3-(trifluoromethyl)phenyl]cyclobutyl}methanol

The title compound was prepared according to the procedure of Example 1C, substituting Example 6B for Example 1B. LC-MS: m/z 308 (M+H); $^1$H-NMR (400 MHz, CDCl$_3$): δ ppm 8.42-8.41 (m, 1H), 7.50-7.43 (m, 1H), 7.39-7.35 (m, 1H), 7.18-7.15 (m, 2H), 7.09-7.08 (m, 1H), 6.87 (s, 1H), 6.63 (d, J=8 Hz, 1H), 5.68 (d, J=4.8 Hz, 1H), 4.96 (d, J=4.8 Hz, 1H), 2.85-2.70 (m, 2H), 2.30-2.12 (m, 2H), 1.99-1.92 (m, 1H), 1.77-1.72 (m, 1H).

Example 7

[1-(2-methylphenyl)cyclobutyl](pyridin-2-yl)methanol

Example 7A 1-o-tolylcyclobutanecarbonitrile

The title compound was prepared according to the procedure of Example 1A, substituting 2-o-tolylacetonitrile for 2-(2-fluorophenyl)acetonitrile. LC-MS: m/z 172 (M+H).

Example 7B pyridin-2-yl(1-o-tolylcyclobutyl)methanone

The title compound was prepared according to the procedure of Example 1B, substituting Example 7A for Example 1A. LC-MS: m/z 252 (M+H).

Example 7C

[1-(2-methylphenyl)cyclobutyl](pyridin-2-yl)methanol

The title compound was prepared according to the procedure of Example 1C, substituting Example 7B for Example 1B. LC-MS: m/z 254 (M+H); $^1$H-NMR (400 MHz, CD$_3$OD): δ ppm 8.40 (d, J=4.4 Hz, 1H), 7.53-7.49 (m, 2H), 7.24-7.21 (m, 1H), 7.03-6.99 (m, 3H), 6.74-6.72 (m, 2H), 5.14 (s, 1H), 2.73-2.67 (m, 2H), 2.42-2.40 (m, 2H), 2.20-1.80 (m, 2H), 1.80-1.75 (s, 3H).

Example 8

[1-(3-methylphenyl)cyclobutyl](pyridin-2-yl)methanol

Example 8A 1-m-tolylcyclobutanecarbonitrile

The title compound was prepared according to the procedure of Example 1A, substituting m-tolylacetonitrile for 2-(2-fluorophenyl)acetonitrile. LC-MS: m/z 172 (M+H).

Example 8B pyridin-2-yl(1-m-tolylcyclobutyl)methanone

The title compound was prepared according to the procedure of Example 1B, substituting Example 8A for Example 1A. LC-MS: m/z 252 (M+H).

Example 8C

[1-(3-methylphenyl)cyclobutyl](pyridin-2-yl)methanol

The title compound was prepared according to the procedure of Example 1C, substituting Example 8B for Example 1B. LC-MS: m/z 254 (M+H); $^1$H-NMR (400 MHz, DMSO-d$_6$): δ ppm 8.40 (d, J=4.8 Hz, 1H), 7.51-7.48 (m, 1H), 7.17-7.14 (m, 1H), 7.01-6.97 (m, 1H), 6.88 (d, J=7.6 Hz, 1H), 6.69 (d, J=4.4 Hz, 1H), 6.58-6.32 (m, 2H), 5.42 (d, J=4.8 Hz, 1H), 4.86 (d, J=4.8 Hz, 1H), 2.71-2.51 (m, 2H), 2.24-2.08 (m, 2H), 2.16 (s, 3H), 1.87-1.81 (m, 1H), 1.72-1.65 (m, 1H).

Example 9

[1-(4-methylphenyl)cyclobutyl](pyridin-2-yl)methanol

Example 9A 1-p-tolylcyclobutanecarbonitrile

The title compound was prepared according to the procedure of Example 1A, substituting p-tolylacetonitrile for 2-(2-fluorophenyl)acetonitrile. LC-MS: m/z 172 (M+H).

Example 9B pyridin-2-yl(1-p-tolylcyclobutyl)methanone

The title compound was prepared according to the procedure of Example 1B, substituting Example 9A for Example 1A. LC-MS: m/z 252 (M+H).

Example 9

[1-(4-methylphenyl)cyclobutyl](pyridin-2-yl)methanol C

The title compound was prepared according to the procedure of Example 1C, substituting Example 9B for Example 1B. LC-MS: m/z 254 (M+H); $^1$H-NMR (400 MHz, DMSO-d$_6$): δ ppm 8.40 (d, J=4.8 Hz, 1H), 7.51-7.47 (m, 1H), 7.16-7.13 (m, 1H), 6.93-6.91 (m, 2H), 6.71-6.65 (m, 3H), 5.42 (d, J=4.8 Hz, 1H), 4.86 (d, J=4.8 Hz, 1H), 2.75-2.62 (m, 2H), 2.21 (s, 3H), 2.19-2.06 (m, 2H), 1.89-1.82 (m, 1H), 1.70-1.67 (m, 1H).

Example 10 pyridin-2-yl{1-[2-(trifluoromethoxy)phenyl]cyclobutyl}methanol

Example 10A 1-(2-(trifluoromethoxy)phenyl)cyclobutanecarbonitrile

The title compound was prepared according to the procedure of Example 1A, substituting 2-(2-(trifluoromethoxy)phenyl)acetonitrile for 2-(2-fluorophenyl)acetonitrile. LC-MS: m/z 242 (M+H).

Example 10B pyridin-2-yl(1-(2-(trifluoromethoxy)phenyl)cyclobutyl)methanone

The title compound was prepared according to the procedure of Example 1B, substituting Example 10A for Example 1A. LC-MS: m/z 322 (M+H).

Example 10C pyridin-2-yl{1-[2-(trifluoromethoxy)phenyl]cyclobutyl}methanol

The title compound was prepared according to the procedure of Example 1C, substituting Example 10B for Example 1B. LC-MS: m/z 324 (M+H); $^1$H-NMR (400 MHz, CD$_3$OD): δ ppm 8.26 (d, J=4.0 Hz, 1H), 7.44-7.40 (m, 1H), 7.12-7.08 (m, 2H), 7.01-6.92 (m, 2H), 6.83 (d, J=7.6 Hz, 2H), 7.70 (d, J=7.6 Hz, 1H), 5.01 (s, 1H), 2.72-2.61 (m, 2H), 2.31-2.21 (m, 2H), 1.98-1.96 (m, 1H), 1.73-1.67 (m, 1H).

Example 11 pyridin-2-yl{1-[3-(trifluoromethoxy)phenyl]cyclobutyl}methanol

Example 11A 1-(3-(trifluoromethoxy)phenyl)cyclobutanecarbonitrile

The title compound was prepared according to the procedure of Example 1A, substituting 2-(3-(trifluoromethoxy)phenyl)acetonitrile for 2-(2-fluorophenyl)acetonitrile. LC-MS: m/z 242 (M+H).

Example 11B pyridin-2-yl(1-(3-(trifluoromethoxy)phenyl)cyclobutyl)methanone

The title compound was prepared according to the procedure of Example 1B, substituting Example 11A for Example 1A. LC-MS: m/z 322 (M+H).

Example 11C pyridin-2-yl{1-[3-(trifluoromethoxy)phenyl]cyclobutyl}methanol

The title compound was prepared according to the procedure of Example 1C, substituting Example 11B for Example 1B. LC-MS: m/z 324 (M+H); $^1$H-NMR (400 MHz, CDCl$_3$): δ pm 8.34 (d, J=4.8, Hz, 1H), 7.48-7.44 (m, 1H), 7.26-7.19 (m, 1H), 7.12-7.09 (m, 1H), 6.99-6.97 (m, 1H), 6.90 (d, J=6.8 Hz, 1H), 6.67 (d, J=8 Hz, 1H), 6.54 (s, 1H), 4.90 (s, 1H), 4.51 (s, 1H), 2.74-2.65 (m, 2H), 2.35-2.23 (m, 2H), 2.12-2.01 (m, 1H), 1.89-1.79 (m, 1H).

Example 12 pyridin-2-yl{1-[4-(trifluoromethoxy)phenyl]cyclobutyl}methanol

Example 12A 1-(4-(trifluoromethoxy)phenyl)cyclobutanecarbonitrile

The title compound was prepared according to the procedure of Example 1A, substituting 2-(4-(trifluoromethoxy)phenyl)acetonitrile for 2-(2-fluorophenyl)acetonitrile. LC-MS: m/z 242 (M+H).

Example 12B pyridin-2-yl(1-(4-(trifluoromethoxy)phenyl)cyclobutyl)methanone

The title compound was prepared according to the procedure of Example 1B, substituting Example 12A for Example 1A. LC-MS: m/z 322 (M+H).

Example 12C pyridin-2-yl{1-[4-(trifluoromethoxy)phenyl]cyclobutyl}methanol

The title compound was prepared according to the procedure of Example 1C, substituting Example 12B for Example 1B. LC-MS: m/z 324 (M+H); $^1$H-NMR (400 MHz, CDCl$_3$): δ ppm 8.32 (d, J=4.8 Hz, 1H), 7.49-7.45 (m, 1H), 7.12-7.09 (m, 1H), 6.85 (d, J=8 Hz, 2H), 6.86-6.83 (m, 2H), 6.70 (d, J=8 Hz, 1H), 4.90 (s, 1H), 4.69 (s, 1H), 2.75-2.65 (m, 2H), 2.35-2.24 (m, 2H), 2.07-1.99 (m, 1H), 1.87-1.80 (m, 1H).

Example 13

{1-[3,5-bis(trifluoromethyl)phenyl]cyclobutyl}(pyridin-2-yl)methanol

Example 13A 1-(3,5-bis(trifluoromethyl)phenyl)cyclobutanecarbonitrile

The title compound was prepared according to the procedure of Example 1A, substituting 2-(3,5-bis(trifluoromethyl)phenyl)acetonitrile for 2-(2-fluorophenyl)acetonitrile. LC-MS: m/z 294 (M+H).

Example 13B (1-(3,5-bis(trifluoromethyl)phenyl)cyclobutyl)(pyridin-2-yl)methanone The title compound was prepared according to the procedure of Example 1B, substituting Example 13A for Example 1A. LC-MS: m/z 374 (M+H).

Example 13C

{1-[3,5-bis(trifluoromethyl)phenyl]cyclobutyl}(pyridin-2-yl)methanol

The title compound was prepared according to the procedure of Example 1C, substituting Example 13B for Example 1B. LC-MS: m/z 376 (M+H); $^1$H NMR (400 MHz, CDCl$_3$): δ ppm 8.28-8.27 (m, 1H), 7.62-7.56 (m, 2H), 7.16-7.13 (m, 3H), 6.96-6.94 (m, 1H), 5.03 (s, 1H), 4.43-4.32 (m, 2H), 2.84-2.69 (m, 2H), 2.43-2.33 (m, 2H), 2.18-2.09 (m, 1H) 1.95-1.81 (m, 1H).

Example 14

{1-[3-fluoro-5-(trifluoromethyl)phenyl]cyclobutyl}(pyridin-2-yl)methanol

Example 14A 1-(3-fluoro-5-(trifluoromethyl)phenyl)cyclobutanecarbonitrile

The title compound was prepared according to the procedure of Example 1A, substituting 2-(3-fluoro-5-(trifluoromethyl)phenyl)acetonitrile for 2-(2-fluorophenyl)acetonitrile. LC-MS: m/z 244 (M+H)

Example 14B (1-(3-fluoro-5-(trifluoromethyl)phenyl)cyclobutyl)(pyridin-2-yl)methanone The title compound was prepared according to the procedure of Example 1B, substituting Example 14A for Example 1A. LC-MS: m/z 324 (M+H)

Example 14C

{1-[3-fluoro-5-(trifluoromethyl)phenyl]cyclobutyl}(pyridin-2-yl)methanol

The title compound was prepared according to the procedure of Example 1C, substituting Example 14B for Example 1B. LC-MS: m/z 326 (M+H); $^1$H NMR (400 MHz, CDCl$_3$): δ ppm 8.44 (s, 1H), 7.51-7.48 (m, 1H), 7.13-7.10 (m, 2H), 6.86-6.80 (m, 1H), 6.71 (s, 1H), 4.28 (s, 1H), 2.68-2.66 (m, 2H), 2.40-2.27 (m, 2H), 191-1.80 (m, 2H).

Example 15

{1-[4-fluoro-3-(trifluoromethyl)phenyl]cyclobutyl}(pyridin-2-yl)methanol

Example 15A 1-(4-fluoro-3-(trifluoromethyl)phenyl)cyclobutanecarbonitrile

The title compound was prepared according to the procedure of Example 1A, substituting 2-(4-fluoro-3-(trifluoromethyl)phenyl)acetonitrile for 2-(2-fluorophenyl)acetonitrile. LC-MS: m/z 244 (M+H).

Example 15B (1-(4-fluoro-3-(trifluoromethyl)phenyl)cyclobutyl)(pyridin-2-yl)methanone The title compound was prepared according to the procedure of Example 1B, substituting Example 15A for Example 1A. LC-MS: m/z 324 (M+H).

Example 15C

{1-[4-fluoro-3-(trifluoromethyl)phenyl]cyclobutyl}(pyridin-2-yl)methanol

The title compound was prepared according to the procedure of Example 1C, substituting Example 15B for Example 1B. LC-MS: m/z 326 (M+H); $^1$H NMR (400 MHz, CDCl$_3$): δ ppm 8.32-8.31 (m, 1H), 7.56-7.52 (m, 2H), 7.14-6.95 (m, 3H), 6.88-6.84 (m, 1H), 4.94 (s, 1H), 4.38 (s, 1H), 2.76-2.67 (m, 2H), 2.35-2.26 (m, 2H), 2.13-2.04 (m, 1H) 1.91-1.82 (m, 1H).

Example 16

{1-[4-(methylsulfonyl)phenyl]cyclobutyl}(pyridin-2-yl)methanol

Example 16A 1-(4-(methylsulfonyl)phenyl)cyclobutanecarbonitrile

The title compound was prepared according to the procedure of Example 1A, substituting 2-(4-(methylsulfonyl)phenyl)acetonitrile for 2-(2-fluorophenyl)acetonitrile. LC-MS: m/z 236 (M+H).

Example 16B (1-(4-(methylsulfonyl)phenyl)cyclobutyl)(pyridin-2-yl)methanone

The title compound was prepared according to the procedure of Example 1B, substituting Example 16A for Example 1A. LC-MS: m/z 316 (M+H).

Example 16C

{1-[4-(methylsulfonyl)phenyl]cyclobutyl}(pyridin-2-yl)methanol

The title compound was prepared according to the procedure of Example 1C, substituting Example 16B for Example 1B. LC-MS: m/z 318 (M+H); ¹H NMR (400 MHz, CDCl₃): δ ppm 8.31 (d, J=4.4 Hz, 1H), 7.71 (d, J=8.4 Hz, 2H), 7.55-7.51 (m, 1H), 7.14-7.12 (m, 1H), 7.03 (d, J=8.8 Hz, 2H), 6.85-6.83 (d, J=7.6 Hz, 1H), 4.98 (s, 1H), 3.02 (s, 1H), 2.79-2.72 (m, 2H), 2.37-2.30 (m, 2H), 2.09-2.02 (m, 1H), 1.88-1.82 (m, 1H).

Example 17

{1-[3-fluoro-4-(trifluoromethyl)phenyl]cyclobutyl}(pyridin-2-yl)methanol

Example 17A 1-(3,4-bis(trifluoromethyl)phenyl)cyclobutanecarbonitrile

The title compound was prepared according to the procedure of Example 1A, substituting 2-(3-fluoro-4-(trifluoromethyl)phenyl)acetonitrile for 2-(2-fluorophenyl)acetonitrile. LC-MS: m/z 244 (M+H).

Example 17B (1-(3-fluoro-4-(trifluoromethyl)phenyl)cyclobutyl)(pyridin-2-yl)methanone The title compound was prepared according to the procedure of Example 1B, substituting Example 17A for Example 1A. LC-MS: m/z 324 (M+H).

Example 17C

{1-[3-fluoro-4-(trifluoromethyl)phenyl]cyclobutyl}(pyridin-2-yl)methanol

The title compound was prepared according to the procedure of Example 1C, substituting Example 17B for Example 1B. LC-MS: m/z 326 (M+H); ¹H NMR (400 MHz, CDCl₃): δ ppm 8.34-8.33 (m, 1H), 7.57-7.53 (m, 1H), 7.37-7.33 (m, 3H), 7.16-7.13 (m, 1H), 6.88-6.86 (m, 1H), 6.71-6.66 (m, 2H), 4.96 (s, 1H), 2.75-2.69 (m, 2H), 2.35-2.26 (m, 2H), 2.08-2.01 (m, 1H), 1.87-1.80 (m, 1H).

Example 18

{1-[4-(diethylamino)phenyl]cyclobutyl}(pyridin-2-yl)methanol

Example 18A 1-(4-(diethylamino)phenyl)cyclobutanecarbonitrile

The title compound was prepared according to the procedure of Example 1A, substituting 2-(4-(diethylamino)phenyl)acetonitrile for 2-(2-fluorophenyl)acetonitrile. LC-MS: m/z 229 (M+H).

Example 18B (1-(4-(diethylamino)phenyl)cyclobutyl)(pyridin-2-yl)methanone

The title compound was prepared according to the procedure of Example 1B, substituting Example 18A for Example 1A. LC-MS: m/z 309 (M+H).

Example 18C

{1-[4-(diethylamino)phenyl]cyclobutyl}(pyridin-2-yl)methanol

The title compound was prepared according to the procedure of Example 1C, substituting Example 18B for Example 1B. LC-MS: m/z 311 (M+H); ¹H NMR (400 MHz, CDCl₃): δ ppm 8.63 (d, J=4 Hz, 1H), 7.51-7.47 (m, 1H), 7.41-7.39 (m, 1H), 7.32-7.22 (m, 3H), 7.06-7.05 (m, 1H), 6.79-6.77 (m, 1H), 3.25-3.18 (m, 2H), 2.52-2.45 (m, 2H), 2.15-2.13 (m, 1H), 1.90-1.86 (m, 1H).

Example 19 pyridin-2-yl(1-pyridin-2-ylcyclobutyl)methanol

Example 19A 1-(pyridin-2-yl)cyclobutanecarbonitrile

The title compound was prepared according to the procedure of Example 1A, substituting 2-(pyridin-2-yl)acetonitrile for 2-(2-fluorophenyl)acetonitrile. LC-MS: m/z 159 (M+H).

Example 19B pyridin-2-yl(1-(pyridin-2-yl)cyclobutyl)methanone

The title compound was prepared according to the procedure of Example 1B, substituting Example 19A for Example 1A. LC-MS: m/z 239 (M+H).

Example 19C pyridin-2-yl(1-pyridin-2-ylcyclobutyl)methanol

The title compound was prepared according to the procedure of Example 1C, substituting Example 19B for Example 1B. LC-MS: m/z 241 (M+H); ¹H NMR (400 MHz, CDCl₃): δ ppm 8.54-8.45 (m, 1H), 7.48-7.46 (m, 2H), 7.09 (s, 2H), 6.88-6.81 (m, 1H), 4.42 (s, 1H), 2.70-2.59 (m, 2H), 2.46-2.41 (m, 2H), 1.75-1.72 (m, 2H).

Example 20 pyridin-2-yl(1-pyridin-3-ylcyclobutyl)methanol

Example 20A 1-(pyridin-3-yl)cyclobutanecarbonitrile

The title compound was prepared according to the procedure of Example 1A, substituting 2-(pyridin-3-yl)acetonitrile for 2-(2-fluorophenyl)acetonitrile. LC-MS: m/z 159 (M+H).

Example 20B pyridin-2-yl(1-(pyridin-3-yl)cyclobutyl)methanone

The title compound was prepared according to the procedure of Example 1B, substituting Example 20A for Example 1A. LC-MS: m/z 239 (M+H).

Example 20C pyridin-2-yl(1-pyridin-3-ylcyclobutyl)methanol

The title compound was prepared according to the procedure of Example 1C, substituting Example 20B for Example 1B. LC-MS: m/z 241 (M+H); $^1$H NMR (400 MHz, CDCl$_3$): δ ppm 8.44-8.42 (m, 1H), 8.39-8.38 (m, 1H), 8.04-8.03 (m, 1H), 7.51-7.47 (m, 1H), 7.19-7.09 (m, 3H), 6.85-6.83 (m, 1H), 4.32 (s, 1H), 2.73-2.60 (m, 2H), 2.44-2.37 (m, 1H), 2.30-2.23 (m, 1H), 1.96-1.77 (m, 2H).

Example 21 pyridin-2-yl(1-pyridin-4-ylcyclobutyl)methanol

Example 21A 1-(pyridin-4-yl)cyclobutanecarbonitrile

The title compound was prepared according to the procedure of Example 1A, substituting 2-(pyridin-4-yl)acetonitrile for 2-(2-fluorophenyl)acetonitrile. LC-MS: m/z 159 (M+H).

Example 21B pyridin-2-yl(1-(pyridin-4-yl)cyclobutyl)methanone

The title compound was prepared according to the procedure of Example 1B, substituting Example 21A for Example 1A. LC-MS: m/z 239 (M+H).

Example 21C pyridin-2-yl(1-pyridin-4-ylcyclobutyl)methanol

The title compound was prepared according to the procedure of Example 1C, substituting Example 21B for Example 1B. LC-MS: m/z 241 (M+H); $^1$H NMR (400 MHz, CDCl$_3$): δ ppm 8.44-8.42 (m, 1H), 8.39-8.38 (m, 1H), 8.04-8.03 (m, 1H), 7.51-7.47 (m, 1H), 7.19-7.09 (m, 3H), 6.85-6.83 (m, 1H), 4.32 (s, 1H), 2.71-2.60 (m, 2H), 2.44-2.37 (m, 1H), 2.30-2.16 (m, 1H), 1.96-1.78 (m, 2H).

Example 22

[1-(1,1'-biphenyl-4-yl)cyclobutyl](pyridin-2-yl)methanol

Example 22A 1-(biphenyl-4-yl)cyclobutanecarbonitrile

The title compound was prepared according to the procedure of Example 1A, substituting 2-(biphenyl-4-yl)acetonitrile for 2-(2-fluorophenyl)acetonitrile. LC-MS: m/z 256 (M+Na).

Example 22B (1-(biphenyl-4-yl)cyclobutyl)(pyridin-2-yl)methanone

The title compound was prepared according to the procedure of Example 1B, substituting Example 22A for Example 1A. LC-MS: m/z 314 (M+H).

Example 22C

Meiling Sun

[1-(1,1'-biphenyl-4-yl)cyclobutyl](pyridin-2-yl)methanol

The title compound was prepared according to the procedure of Example 1C, substituting Example 22B for Example 1B. LC-MS: m/z 316 (M+H); $^1$H NMR (400 MHz, CDCl$_3$): δ ppm 8.39-8.37 (m, 1H), 7.59-7.57 (m, 2H), 7.45-7.40 (m, 5H), 7.33-7.35 (m, 1H), 7.11-7.08 (m, 1H), 6.96-6.93 (m, 1H), 6.64-6.62 (m, 1H), 4.91 (s, 1H), 4.47 (s, 1H), 2.84-2.78 (m, 1H), 2.70-2.65 (m, 1H), 2.40-2.27 (m, 2H), 1.96-1.79 (m, 2H).

Example 23

[1-(3-phenoxyphenyl)cyclobutyl](pyridin-2-yl)methanol

Example 23A 1-(3-phenoxyphenyl)cyclobutanecarbonitrile

The title compound was prepared according to the procedure of Example 1A, substituting 2-(3-phenoxyphenyl)acetonitrile for 2-(2-fluorophenyl)acetonitrile. LC-MS: m/z 272 (M+Na).

Example 23B (1-(3-phenoxyphenyl)cyclobutyl)(pyridin-2-yl)methanone

The title compound was prepared according to the procedure of Example 1B, substituting Example 23A for Example 1A. LC-MS: m/z 330 (M+H).

Example 23C

[1-(3-phenoxyphenyl)cyclobutyl](pyridin-2-yl)methanol

The title compound was prepared according to the procedure of Example 1C, substituting Example 23B for Example 1B. LC-MS: m/z 332 (M+H); $^1$H NMR (400 MHz, CDCl$_3$): δ ppm 8.35-8.34 (m, 1H), 7.43-7.39 (m, 1H), 7.43-7.39 (m, 1H), 7.27-7.23 (m, 2H), 7.15-7.11 (m, 1H), 7.07-7.00 (m, 1H), 6.86 (d, J=8.0 Hz, 2H), 6.78 (d, J=6.0 Hz, 1H), 6.70-6.64 (m, 2H), 6.51 (s, 1H), 4.87 (s, 1H), 4.57 (s, 1H), 2.74-2.60 (m, 2H), 2.32-2.19 (m, 2H), 2.02-1.95 (m, 1H), 1.83-1.77 (m, 1H).

Example 24

[1-(4-phenoxyphenyl)cyclobutyl](pyridin-2-yl)methanol

Example 24A 1-(4-phenoxyphenyl)cyclobutanecarbonitrile

The title compound was prepared according to the procedure of Example 1A, substituting 2-(4-phenoxyphenyl)acetonitrile for 2-(2-fluorophenyl)acetonitrile. LC-MS: m/z 250 (M+H).

Example 24B (1-(4-phenoxyphenyl)cyclobutyl)(pyridin-2-yl)methanone

The title compound was prepared according to the procedure of Example 1B, substituting Example 24A for Example 1A. LC-MS: m/z 330 (M+H).

Example 24C

[1-(4-phenoxyphenyl)cyclobutyl](pyridin-2-yl)methanol

The title compound was prepared according to the procedure of Example 1C, substituting Example 24B for Example 1B. LC-MS: m/z 332 (M+H); $^1$H NMR (400 MHz, CDCl$_3$): δ ppm 8.38-8.37 (m, 1H), 7.49-7.44 (m, 1H), 7.34-7.29 (m, 2H), 7.12-7.05 (m, 2H), 6.98-6.94 (m, 2H), 6.82 (s, 4H), 6.67 (d, J=7.6 Hz, 1H), 4.89 (s, 1H), 2.77-2.72 (m, 1H), 2.68-2.62 (m, 1H), 2.36-2.23 (m, 2H), 2.06-1.98 (m, 1H), 1.89-1.80 (m, 1H).

Example 25

[1-(4-benzylphenyl)cyclobutyl](pyridin-2-yl)methanol

Example 25A 1-(4-benzylphenyl)cyclobutanecarbonitrile

The title compound was prepared according to the procedure of Example 1A, substituting 2-(4-benzylphenyl)acetonitrile for 2-(2-fluorophenyl)acetonitrile. LC-MS: m/z 248 (M+H).

Example 25B (1-(4-benzylphenyl)cyclobutyl)(pyridin-2-yl)methanone

The title compound was prepared according to the procedure of Example 1B, substituting Example 25A for Example 1A. LC-MS: m/z 328 (M+H).

Example 25C

[1-(4-benzylphenyl)cyclobutyl](pyridin-2-yl)methanol

The title compound was prepared according to the procedure of Example 1C, substituting Example 25B for Example 1B. LC-MS: m/z 330 (M+H); $^1$H NMR (400 MHz, CDCl$_3$): δ ppm 8.37 (d, J=4.4 Hz, 1H), 7.43-7.39 (m, 1H), 7.30-7.25 (m, 2H), 7.21-7.15 (m, 3H), 7.11-7.08 (m, 1H), 6.79 (d, J=8 Hz 2H), 6.56 (d, J=7.6 Hz 1H), 4.86 (s, 1H), 3.93 (m, 2H), 2.75-2.74 (m, 1H), 2.62-2.58 (m, 1H), 2.31-2.21 (m, 2H), 1.98-1.94 (m, 1H), 1.82-1.78 (m, 1H).

Example 26

(S)-[1-(3,4-dichlorophenyl)cyclobutyl](pyridin-2-yl)methanol

Example 26A (1-(3,4-dichlorophenyl)cyclobutyl)(pyridin-2-yl)methanone

The title compound was prepared according to the procedure of Example 1B, substituting 1-(3,4-dichlorophenyl)cyclobutanecarbonitrile for Example 1A. MS (DCI$^+$) M/Z 307 (M+H)$^+$. $^1$H NMR (300 MHz, DMSO-d$_6$) δ ppm 8.58 (dt, J=4.7, 1.3 Hz, 1H), 7.96-7.98 (m, 2H), 7.65 (t, J=8.0 Hz, 1H), 7.51-7.62 (m, 2H), 7.30-7.35 (m, 2H), 2.88-2.95 (m, 2H), 2.61-2.65 (m, 2H), 1.78-2.01 (m, 2H).

Example 26B (S)-[1-(3,4-dichlorophenyl)cyclobutyl](pyridin-2-yl)methanol

Example 26A (3.44 g, 11.23 mmol) and formic acid (1.853 ml, 48.3 mmol) were cooled in an ice bath and triethylamine (3.91 ml, 28.1 mmol) was added. The white slurry was warmed to room temperature and (S,S)—N-(p-touenesulfonyl)-1,2-diphenylethanediamine(chloro)(p-cumene)ruthenium (II) (0.072 g, 0.112 mmol) added. The reaction mixture was warmed to 35° C. After 15 hours, LCMS showed nearly complete conversion. After 18 hours, the reaction mixture was diluted with dichloromethane and saturated aqueous NaHCO$_3$, extracted 2× with dichloromethane. The organic layers were dried (Na$_2$SO$_4$), filtered, and concentrated. The residue was chromatographed on silica gel (0-75% EtOAc/hexanes) to give the title compound (3.378 g, 10.96 mmol, 98% yield). Chiral HPLC (2% IPA/hexanes isochratic, 0.7 mL/min, OJ-H column, minor=11.8 min, major=13.1 min) showed 96% ee in favor of the title compound. MS (DCI$^+$) M/Z 308 (M+H)+. $^1$H NMR (300 MHz, DMSO-d$_6$) δ ppm 8.42 (ddd, J=4.8, 1.8, 0.9 Hz, 1H), 7.55 (td, J=7.7, 1.8 Hz, 1H), 7.36 (d, J=8.3 Hz, 1H), 7.18 (ddd, J=7.5, 4.8, 1.2 Hz, 1H), 6.90 (d, J=2.1 Hz, 1H), 6.77 (d, J=7.9 Hz, 1H), 6.70 (dd, J=8.3, 2.1 Hz, 1H), 5.65 (d, J=4.4 Hz, 1H), 4.92 (d, J=4.3 Hz, 1H), 2.62-2.82 (m, 2H), 2.07-2.27 (m, 2H), 1.99 (s, 1H), 1.64-1.78 (m, 1H). [α]$_D$=−57.40 (c=0.50 CH$_3$OH).

Example 27

(S)-{1-[2-fluoro-4-(trifluoromethyl)phenyl]cyclobutyl}(pyridin-2-yl)methanol

Example 27A 1-(2-fluoro-4-(trifluoromethyl)phenyl)cyclobutanecarbonitrile

The title compound was prepared according to the procedure of Example 1A, substituting 2-(2-fluoro-4-(trifluoromethyl)phenyl)acetonitrile for 2-(2-fluorophenyl)acetonitrile.

Example 27B (1-(2-fluoro-4-(trifluoromethyl)phenyl)cyclobutyl)(pyridin-2-yl)methanone The title compound was prepared according to the procedure of Example 1B, substituting Example 27A for Example 1A. MS (DCI/NH$_3$) m/z 324 (M+H)$^+$. $^1$H NMR (300 MHz, CDCl$_3$) δ ppm 8.37 (ddd, J=4.7, 1.8, 0.9 Hz, 1H), 7.91-8.02 (m, 2H), 7.73 (td, J=7.7, 1.8 Hz, 1H), 7.37-7.42 (m, 1H), 7.26 (m, 1H), 7.10 (dd, J=10.6, 1.8 Hz, 1H), 3.03-3.13 (m, 2H), 2.61-2.72 (m, 2H), 1.96-2.08 (m, 2H).

Example 27C (S)-{1-[2-fluoro-4-(trifluoromethyl)phenyl]cyclobutyl}(pyridin-2-yl)methanol The title compound was prepared according to the procedure of Example 26B, substituting Example 27B for Example 26A. Chiral HPLC (2% IPA/hexanes, OD-H column) showed 76% ee in favor of the title compound. MS (DCI/NH₃) m/z 326 (M+H)⁺. ¹H NMR (300 MHz, DMSO-d₆) δ 8.37 (ddd, J=4.8, 1.7, 0.9, 1H), 7.60 (td, J=7.7, 1.8, 1H), 7.46-7.27 (m, 2H), 7.20 (ddd, J=7.5, 4.8, 1.1, 1H), 7.12-6.89 (m, 2H), 5.67 (d, J=4.9, 1H), 4.97 (d, J=4.8, 1H), 2.87-2.65 (m, 2H), 2.40-2.13 (m, 2H), 1.94-1.62 (m, 2H). [α]$_D$=−20.45° (c=0.25 CH₃OH).

Example 28

(S)-pyridin-2-yl{1-[4-(trifluoromethyl)phenyl]cyclobutyl}methanol

Example 28A 1-(4-(trifluoromethyl)phenyl)cyclobutanecarbonitrile

The title compound was prepared according to the procedure of Example 1A, substituting 2-(4-(trifluoromethyl)phenyl)acetonitrile for 2-(2-fluorophenyl)acetonitrile.

Example 28B pyridin-2-yl(1-(4-(trifluoromethyl)phenyl)cyclobutyl)methanone

The title compound was prepared according to the procedure of Example 1B, substituting Example 28A for Example 1A. MS (DCI/NH₃) m/z 226 (M+H)⁺. ¹H NMR (300 MHz, DMSO-d₆) d ppm 7.80-7.81 (bs, 2H), 7.69-7.73 (m, 2H), 2.61-2.84 (m, 4H), 2.29 (s, 1H), 1.97-2.10 (m, 1H).

Example 28C (S)-pyridin-2-yl{1-[4-(trifluoromethyl)phenyl]cyclobutyl}methanol The title compound was prepared according to the procedure of Example 26B, substituting Example 28B for Example 26A. Chiral HPLC (2% IPA/hexanes isochratic, 0.7 mL/min, OJ-H column, minor=9.6 min, major=10.9 min) showed 97% ee in favor of the title compound. MS (DCI/NH₃) m/z 307 (M+H)⁺. ¹H NMR (300 MHz, DMSO-d₆) δ ppm 8.41 (ddd, J=4.8, 1.8, 0.9 Hz, 1H), 7.49-7.55 (m, 2H), 7.46 (d, J=0.9 Hz, 1H), 7.17 (ddd, J=7.5, 4.8, 1.2 Hz, 1H), 6.96-7.00 (m, 2H), 6.72-6.76 (m, 1H), 5.63 (d, J=3.5 Hz, 1H), 4.94 (d, J=3.3 Hz, 1H), 2.67-2.86 (m, 2H), 2.12-2.27 (m, 2H), 1.84-1.97 (m, 1H), 1.64-1.78 (m, 1H). [α]$_D$=−47.21° (c=1.0 CH₃OH).

Example 29

(S)-{1-[3-fluoro-4-(trifluoromethyl)phenyl]cyclobutyl}(pyridin-2-yl)methanol

Example 29A 1-(3-fluoro-4-(trifluoromethyl)phenyl)cyclobutanecarbonitrile

The title compound was prepared according to the procedure of Example 1A, substituting 2-(3-fluoro-4-(trifluoromethyl)phenyl)acetonitrile for 2-(2-fluorophenyl)acetonitrile. MS (DCI/NH₃) m/z 244 (M+H)⁺. ¹H NMR (300 MHz, DMSO-d₆) δ ppm 7.86 (d, J=7.9 Hz, 1H), 7.71 (dd, J=11.9, 1.7 Hz, 1H), 7.50-7.54 (m, 1H), 2.66-2.79 (m, 4H), 2.24-2.34 (m, 1H), 1.96-2.10 (m, 1H).

Example 29B (1-(3-fluoro-4-(trifluoromethyl)phenyl)cyclobutyl)(pyridin-2-yl)methanone The title compound was prepared according to the procedure of Example 1B, substituting Example 29A for Example 1A. MS (DCI/NH₃) m/z 324. ¹H NMR (300 MHz, DMSO-d₆) δ ppm 8.54 (dt, J=4.7, 1.3 Hz, 1H), 7.96-7.98 (m, 2H), 7.67 (t, J=8.0 Hz, 1H), 7.51-7.62 (m, 2H), 7.29-7.35 (m, 1H), 2.88-2.98 (m, 2H), 2.64 (dd, J=21.5, 5.6 Hz, 1H), 2.61-2.65 (m, 1H), 1.78-2.01 (m, 2H).

Example 29C (S)-{1-[3-fluoro-4-(trifluoromethyl)phenyl]cyclobutyl}(pyridin-2-yl)methanol The title compound was prepared according to the procedure of Example 26B, substituting Example 29B for Example 26A. Chiral HPLC (2% IPA/hexanes isochratic, 0.7 mL/min, OJ-H column) showed 97% ee in favor of the title compound. MS (DCI/NH₃) m/z 326 (M+H). ¹H NMR (300 MHz, DMSO-d₆) δ ppm 8.42 (ddd, J=4.8, 1.8, 0.9 Hz, 1H), 7.49-7.59 (m, 2H), 7.16-7.24 (m, 1H), 6.75-6.83 (m, 3H), 5.72 (d, J=4.7 Hz, 1H), 4.95 (d, J=4.6 Hz, 1H), 2.65-2.85 (m, 2H), 2.13-2.30 (m, 2H), 1.69-1.91 (m, 2H). [α]$_D$=−29.47° (c=0.21 CH₃OH).

Example 30

(S)-[1-(3,4-dichlorophenyl)cyclobutyl](3-methylpyridin-2-yl)methanol

Example 30A (1-(3,4-dichlorophenyl)cyclobutyl)(3-methylpyridin-2-yl)methanone The title compound was prepared according to the procedure of Example 1B, substituting 1-(3,4-dichlorophenyl)cyclobutanecarbonitrile for Example 1A and substituting 2-bromo-3-methylpyridine for 2-bromo-pyridine. MS (DCI/NH₃) m/z 320 (M+H)⁺. ¹H NMR (300 MHz, DMSO-d₆) δ ppm 8.34-8.37 (m, 1H), 7.65-7.76 (m, 1H), 7.49-7.54 (m, 2H), 7.35 (dd, J=7.8, 4.6 Hz, 1H), 7.28 (dd, J=8.4, 2.2 Hz, 1H), 2.93 (dd, J=7.1, 3.0 Hz, 1H), 2.93 (dd, J=21.1, 7.4 Hz, 1H), 2.52-2.58 (m, 2H), 2.32 (s, 3H), 1.79-2.11 (m, 2H).

Example 30B (S)-[1-(3,4-dichlorophenyl)cyclobutyl](3-methylpyridin-2-yl)methanol The title compound was prepared according to the procedure of Example 26B, substituting Example 30A for Example 26A. Chiral HPLC (2% IPA/hexanes isochratic, 0.7 mL/min, OJ-H column, showed 96% ee in favor of the title compound. MS (DCI/NH₃) m/z 322 (M+H)⁺. ¹H NMR (300 MHz, DMSO-d₆) δ ppm 8.35 (dd, J=4.7, 1.7 Hz, 1H), 7.37-7.42 (m, 2H), 7.13 (dd, J=7.6, 4.7 Hz, 1H), 7.04 (d, J=2.1 Hz, 1H), 6.90 (dd, J=8.3, 2.2 Hz, 1H), 5.21-5.24 (m, 1H), 4.84-4.87 (m, 1H), 2.72-2.94 (m, 2H), 2.10-2.18 (m, 2H), 1.79-1.96 (m, 1H), 1.75 (s, 4H). [α]$_D$=−23.50° (c=0.50 CH$_3$OH).

Example 31 pyrimidin-2-yl{1-[4-(trifluoromethoxy)phenyl] cyclobutyl}methanol

Example 31A

1-[4-(trifluoromethoxy)phenyl]cyclobutanecarbonitrile

To sodium hydride (4.4 g, 110 mmol) was slowly added DMSO (100 mL) at 0° C. The mixture was warmed to room temperature and stirred for 10 minutes. A solution of 2-(4-(trifluoromethoxy)phenyl)acetonitrile (10.05 g, 50 mmol) and 1,3-dibromopropane (11.0 g, 55 mmol) in diethyl ether (50 ml) was added over 30 min at ≤30° C. Near the end of the addition, the mixture became very thick purple slurry that could not be stirred. An additional 50 mL of DMSO was added. After stirring for 75 min at room temperature, the reaction was complete according to LCMS. The reaction mixture was diluted with 25 mL of isopropanol and 15 mL of water, and extracted with ether. The organic layer was washed with water and brine, dried (Na$_2$SO$_4$), filtered, and concentrated to give the title compound. (10.85 g yield 90%).

Example 31B 1-(4-(trifluoromethoxy)phenyl)cyclobutanecarbaldehyde

To a solution of Example 31A (4.82 g, 0.02 mol) in dry dichloromethane (100 mL) at −78° C. under an argon atmosphere was added diisobutylaluminum hydride (24 mL, 1M solution in toluene). The reaction mixture was stirred at the same temperature for 1 hour and then quenched by dropwise addition of potassium sodium tartrate (10% solution in water). The resulting mixture was warmed to room temperature, stirred vigorously for 40 minutes and then diluted with dichloromethane. The organic phase was separated and the aqueous phase extracted with dichloromethane. The combined organic layers were washed with brine, dried over Na$_2$SO$_4$, filtered, and the solvent was evaporated under reduced pressure. The crude product was purified by silica gel column chromatography, eluted with 100% petroleum ether to petroleum ether: ethyl acetate=50:1 to 30:1) to give title compound as a viscous oil (2.7 g, yield 55.3%). LC-MS: m/z (M+H)$^+$ 245.

Example 31C pyrimidin-2-yl{1-[4-(trifluoromethoxy)phenyl] cyclobutyl}methanol To a solution of n-butyllithium (0.48 mL, 1.2 mmol, 2.5 M in hexanes) was added 2-(tributylstannyl)pyrimidine (369 mg, 1.0 mmol) in THF (6.0 mL) under nitrogen atmosphere at −95° C.~1-100° C. After 45 minutes, Example 31B (244 mg, 1.0 mmol) was added at −95° C., and the resulting mixture was stirred for an additional 30 min and then warmed to room temperature for 10 min. Saturated aq. NH$_4$Cl was added and the mixture was extracted with dichloromethane (30 mL), concentrated and purified by Prep-TLC (petroleum ether: ethyl acetate=15:1 to 10:1) to give the title compound (30 mg, yield 9.26%). $^1$H NMR (400 MHz, CDCl$_3$): 8.58 (d, J=8 Hz, 2H), 7.17 (t, J=4 Hz, 1H), 6.95 (d, J=8 Hz, 2H), 6.81 (d, J=8 Hz, 2H), 5.24 (s, 1H), 3.53 (br, 1H), 3.05-2.97 (m, 1H), 2.86-2.79 (m, 1H), 2.46-2.35 (m, 2H), 2.23-2.11 (m, 1H), 1.96-1.86 (m, 1H). LC-MS: m/z (M+H)$^+$ 325.1.

Example 32

[1-(2-fluorophenyl)cyclobutyl](pyrimidin-2-yl) methanol

Example 32A 1-(2-fluorophenyl)cyclobutanecarbonitrile

The title compound was prepared according to the procedure of Example 31A, substituting 2-(2-fluorophenyl)acetonitrile for 2-(4-(trifluoromethoxy)phenyl)acetonitrile.

Example 32B 1-(2-fluorophenyl)cyclobutanecarbaldehyde

The title compound was prepared according to the procedure of Example 31B, substituting Example 32A for Example 31A.

Example 32C

[1-(2-fluorophenyl)cyclobutyl](pyrimidin-2-yl) methanol

The title compound was prepared according to the procedure of Example 31C, substituting Example 32B for Example 31B. $^1$H NMR (400 MHz, CDCl$_3$): 8.59 (d, J=4 Hz, 2H), 7.17 (t, J=4 Hz, 1H), 7.14-7.09 (m, 1H), 7.03-6.96 (m, 2H), 6.74-6.69 (m, 1H), 5.24 (s, 1H), 2.97-2.92 (m, 1H), 2.83-2.76 (m, 1H), 2.51-2.34 (m, 2H), 2.22-2.12 (m, 1H), 1.94-1.85 (m, 1H). LC-MS: m/z (M+H) 259.1.

Example 33

[1-(3-fluorophenyl)cyclobutyl](pyrimidin-2-yl) methanol

Example 33A 1-(3-fluorophenyl)cyclobutanecarbonitrile

The title compound was prepared according to the procedure of Example 31A, substituting 2-(3-fluorophenyl)acetonitrile for 2-(4-(trifluoromethoxy)phenyl)acetonitrile.

Example 33B 1-(3-fluorophenyl)cyclobutanecarbaldehyde

The title compound was prepared according to the procedure of Example 31B, substituting Example 33A for Example 31A.

Example 33C

[1-(3-fluorophenyl)cyclobutyl](pyrimidin-2-yl) methanol

The title compound was prepared according to the procedure of Example 31C, substituting Example 33B for Example 31B. $^1$H NMR (400 MHz, CDCl$_3$): 8.55 (d, J=4 Hz, 2H), 7.12 (t, J=4 Hz, 1H), 7.07-7.00 (m, 1H), 6.78-6.73 (m, 1H), 6.56 (d, J=8 Hz, 1H), 6.46 (d, J=16 Hz, 1H), 5.20 (s, 1H), 3.05-2.98 (m, 1H), 2.85-2.77 (m, 1H), 2.44-2.32 (m, 2H), 2.19-2.12 (m, 1H), 1.94-1.84 (m, 1H). LC-MS: m/z (M+H)$^+$ 259.1.

Example 34

[1-(4-fluorophenyl)cyclobutyl](pyrimidin-2-yl) methanol

Example 34A 1-(4-fluorophenyl)cyclobutanecarbonitrile

The title compound was prepared according to the procedure of Example 31A, substituting 2-(4-fluorophenyl)acetonitrile for 2-(4-(trifluoromethoxy)phenyl)acetonitrile.

Example 34B 1-(4-fluorophenyl)cyclobutanecarbonitrile

The title compound was prepared according to the procedure of Example 31B, substituting Example 34A for Example 31A.

Example 34C

[1-(4-fluorophenyl)cyclobutyl](pyrimidin-2-yl) methanol

The title compound was prepared according to the procedure of Example 31C, substituting Example 34B for Example 31B. $^1$H NMR (400 MHz, CDCl$_3$): 8.55 (d, J=4 Hz, 2H), 7.11 (t, J=4 Hz, 1H), 6.79-6.70 (m, 4H), 5.19 (s, 1H), 3.04-2.97 (m, 1H), 2.83-2.75 (m, 1H), 2.43-2.31 (m, 2H), 2.21-2.12 (m, 1H), 1.93-1.83 (m, 1H). LC-MS: m/z (M+H)$^+$ 259.1.

Example 35

[1-(3,4-difluorophenyl)cyclobutyl](pyrimidin-2-yl) methanol

Example 35A 1-(3,4-difluorophenyl)cyclobutanecarbonitrile

The title compound was prepared according to the procedure of Example 31A, substituting 2-(3,4-difluorophenyl) acetonitrile for 2-(4-(trifluoromethoxy)phenyl)acetonitrile.

Example 35B 1-(3,4-difluorophenyl)cyclobutanecarbaldehyde

The title compound was prepared according to the procedure of Example 31B, substituting Example 35A for Example 31A.

Example 35C

[1-(3,4-difluorophenyl)cyclobutyl](pyrimidin-2-yl) methanol

The title compound was prepared according to the procedure of Example 31C, substituting Example 35B for Example 31B. $^1$H NMR (400 MHz, CDCl$_3$): 8.57 (d, J=4 Hz, 2H), 7.14 (t, J=4 Hz, 1H), 6.89-6.82 (m, 1H), 6.61-6.56 (m, 1H), 6.50-6.46 (m, 1H), 5.19 (s, 1H), 3.04-2.97 (m, 1H), 2.83-2.75 (m, 1H), 2.43-2.31 (m, 2H), 2.21-2.12 (m, 1H), 1.93-1.83 (m, 1H). LC-MS: m/z (M+H)$^+$ 277.1.

Example 36 pyrimidin-2-yl{1-[2-(trifluoromethoxy)phenyl] cyclobutyl}methanol

Example 36A 1-(2-(trifluoromethoxy)phenyl)cyclobutanecarbonitrile

The title compound was prepared according to the procedure of Example 31A, substituting 2-(2-(trifluoromethoxy) phenyl)acetonitrile for 2-(4-(trifluoromethoxy)phenyl)acetonitrile.

Example 36B 1-(2-(trifluoromethoxy)phenyl)cyclobutanecarbaldehyde

The title compound was prepared according to the procedure of Example 31B, substituting Example 36A for Example 31A.

Example 36C pyrimidin-2-yl{1-[2-(trifluoromethoxy)phenyl]cyclobutyl}methanol

The title compound was prepared according to the procedure of Example 31C, substituting Example 36B for Example 31B. $^1$H NMR (400 MHz, CDCl$_3$): 8.57 (d, J=8 Hz, 2H), 7.19-7.08 (m, 4H), 6.93 (d, J=8 Hz, 1H), 5.25 (s, 1H), 2.97-2.90 (m, 1H), 2.85-2.78 (m, 1H), 2.49-2.35 (m, 2H), 2.22-2.14 (m, 1H), 1.92-1.83 (m, 1H). LC-MS: m/z (M+H)$^+$ 325.1.

Example 37 pyrimidin-2-yl{1-[3-(trifluoromethoxy)phenyl] cyclobutyl}methanol

Example 37A 1-(3-(trifluoromethoxy)phenyl)cyclobutanecarbonitrile

The title compound was prepared according to the procedure of Example 31A, substituting 2-(3-(trifluoromethoxy) phenyl)acetonitrile for 2-(4-(trifluoromethoxy)phenyl)acetonitrile.

Example 37B 1-(3-(trifluoromethoxy)phenyl)cyclobutanecarbaldehyde

The title compound was prepared according to the procedure of Example 31B, substituting Example 37A for Example 31A.

Example 37C pyrimidin-2-yl{1-[3-(trifluoromethoxy)phenyl]cyclobutyl}methanol

The title compound was prepared according to the procedure of Example 31C, substituting Example 37B for Example 31B. $^1$H NMR (400 MHz, CDCl$_3$): 8.54 (d, J=8 Hz, 2H), 7.18-7.11 (m, 2H), 6.93-6.87 (m, 2H), 6.45 (s, 1H), 5.23 (s, 1H), 3.08-3.00 (m, 1H), 2.87-2.79 (m, 1H), 2.45-2.33 (m, 2H), 2.26-2.16 (m, 1H), 1.96-1.87 (m, 1H). LC-MS: m/z (M+H)$^+$ 325.1.

Example 38

[1-(3,4-dichlorophenyl)cyclobutyl](pyrimidin-2-yl)methanol

Example 38A 1-(3,4-dichlorophenyl)cyclobutanecarbaldehyde

The title compound was prepared according to the procedure of Example 31B, substituting 1-(3,4-dichlorophenyl)cyclobutanecarbonitrile for Example 31A.). $^1$H NMR (300 MHz, DMSO-d$_6$) δ ppm 9.65 (s, 1H), 7.64 (d, J=8.3 Hz, 1H), 7.44 (d, J=2.1 Hz, 1H), 7.61 (dd, J=8.3, 2.1 Hz, 1H), 2.61-2.71 (m, 2H), 2.45-2.16 (m, 2H), 1.79-2.01 (m, 2H). MS (DCI/NH$_3$) m/z (M+H)$^+$ 230.

Example 38B

[1-(3,4-dichlorophenyl)cyclobutyl](pyrimidin-2-yl)methanol

The title compound was prepared according to the procedure of Example 31C, substituting Example 38A for Example 31B. $^1$H NMR (300 MHz, DMSO-d$_6$) δ ppm 8.66-8.69 (m, 2H), 7.33-7.37 (m, 2H), 6.98 (d, J=2.1 Hz, 1H), 6.74 (dd, J=8.3, 2.1 Hz, 1H), 5.17-5.20 (m, 1H), 4.88-4.91 (m, 1H), 2.68-2.93 (m, 2H), 2.15-2.28 (m, 2H), 1.66-1.92 (m, 2H). MS (DCI/NH$_3$) m/z (M+H)$^+$ 309.

Example 39

(S)-[1-(3,4-dichlorophenyl)cyclobutyl](pyrimidin-2-yl)methanol

Chiral separation of Example 38B using SFC chromatography with Chiral-cel AD column with 5% methanol/CO$_2$ with 0.1% diethylamine gave the title compound. Absolute stereochemistry was established by X-Ray analysis. $^1$H NMR (300 MHz, DMSO-d$_6$) δ ppm 8.66-8.69 (m, 2H), 7.33-7.37 (m, 2H), 6.97 (d, J=2.1 Hz, 1H), 6.74 (dd, J=8.3, 2.1 Hz, 1H), 5.18 (d, J=6.3 Hz, 1H), 4.91 (s, 1H), 2.74-2.92 (m, 2H), 2.15-2.28 (m, 2H), 1.79-1.92 (m, 1H), 1.64-1.79 (m, 1H). MS (DCI/NH$_3$) m/z (M+H)$^+$ 309. [α]$_D$=−23.2° (c=0.415 CH$_3$OH).

Example 40

(R)-[1-(3,4-dichlorophenyl)cyclobutyl](pyrimidin-2-yl)methanol

Chiral separation of Example 38B using SFC chromatography with Chiral-cel AD column with 5% MeOH/CO$_2$ with 0.1% diethylamine gave the title compound. $^1$H NMR (300 MHz, DMSO-d$_6$) δ ppm 8.87 (d, J=4.8 Hz, 1H), 7.55-7.57 (m, 2H), 7.29 (dd, J=8.4, 2.2 Hz, 1H), 2.89-2.97 (m, 1H), 2.54-2.74 (m, 2H), 1.23-2.00 (m, 5H). MS (DCI/NH$_3$) m/z (M+H)$^+$ 309. [α]$_D$=+27.5° (c=0.455 CH$_3$OH).

Example 41

(S)-pyrimidin-2-yl{1-[4-(trifluoromethyl)phenyl]cyclobutyl}methanol

Example 41A 1-(4-(trifluoromethyl)phenyl)cyclobutanecarbonitrile

The title compound was prepared according to the procedure of Example 31A, substituting 2-(4-(trifluoromethyl)phenyl)acetonitrile for 2-(4-(trifluoromethoxy)phenyl)acetonitrile. $^1$H NMR (300 MHz, DMSO-d$_6$) δ ppm 7.80-7.81 (bs, 2H), 7.69-7.73 (m, 2H), 2.61-2.84 (m, 4H), 2.29 (s, 1H), 1.97-2.10 (m, 1H). MS (DCI/NH$_3$) m/z (M+H)$^+$ 226.

Example 41B 1-(4-(trifluoromethyl)phenyl)cyclobutanecarbaldehyde

The title compound was prepared according to the procedure of Example 31B, substituting Example 41A for Example 31A. $^1$H NMR (300 MHz, DMSO-d$_6$) δ ppm 9.64 (s, 1H), 7.73-7.77 (m, 1H), 7.53-7.59 (m, 1H), 7.39-7.43 (m, 1H), 7.15-7.24 (m, 1H), 2.67-2.76 (m, 2H), 2.26-2.46 (m, 2H), 1.90-1.99 (m, 2H). MS (DCI/NH$_3$) m/z (M+H)$^+$ 229.

Example 41C pyrimidin-2-yl(1-(4-(trifluoromethyl)phenyl)cyclobutyl)methanol

The title compound was prepared according to the procedure of Example 31C, substituting Example 41B for Example 31B. This racemic material was used directly for chiral separation.

Example 41D (S)-pyrimidin-2-yl{1-[4-(trifluoromethyl)phenyl]cyclobutyl}methanol Chiral separation of Example 41C using SFC and Chiralcel AD-H column with 0-5 methanol/100 psi CO$_2$ gave title compound. $^1$H NMR (300 MHz, DMSO-d$_6$) δ ppm 8.63-8.66 (m, 2H), 7.47 (s, 1H), 7.45 (s, 1H), 7.34 (t, J=4.9 Hz, 1H), 7.00-7.04 (m, 2H), 5.12-5.15 (m, 1H), 4.91-4.94 (m, 1H), 2.79-2.99 (m, 2H), 2.20-2.30 (m, 2H), 1.64-1.94 (m, 2H). MS (DCI/NH$_3$) m/z (M+H)$^+$ 309. [α]$_D$=−35.42 (c=0.35 CH$_3$OH).

Example 42

(R)-pyrimidin-2-yl{1-[4-(trifluoromethyl)phenyl]cyclobutyl}methanol

Chiral separation of Example 41C using SFC and Chiralcel AD-H column with 0-5-methanol/100 psi CO$_2$ gave title compound. $^1$H NMR (300 MHz, DMSO-d$_6$) δ ppm 8.63-8.66 (m, 2H), 7.44-7.48 (m, 2H), 7.34 (t, J=4.9 Hz, 1H), 7.00-7.04 (m, 2H), 5.12-5.15 (m, 1H), 4.91-4.94 (m, 1H), 2.79-2.98 (m, 2H), 2.20-2.33 (m, 2H), 1.66-1.92 (m, 2H). MS (DCI/NH$_3$) m/z (M+H)$^+$ 309. [α]$_D$=+36.71 (c=0.30 CH$_3$OH).

Example 43

[1-(3,4-dichlorophenyl)cyclohexyl](pyridin-2-yl)methano

A solution of 2-bromopyridine (0.574 ml, 5.90 mmol) and THF (10 ml) was cooled to <−70° C. and N-hexyllithium (2.57 ml, 5.90 mmol) was added dropwise, keeping the internal temperature ≤−70° C. After 10 min, 1-(3,4-dichlorophenyl)cyclohexanecarbonitrile (1.00 g, 3.93 mmol) was added. After 15 min, LCMS showed complete conversion to two peaks. 2N H$_2$SO$_4$ (10 mL) was added and the mixture was heated at 50° C. for 15 min, cooled, diluted with MTBE (50 mL) and water (50 mL), and the layers separated. The organic layer was washed with brine (20 mL), dried (Na$_2$SO$_4$), filtered, and concentrated, and purified using SFC (0-20% EtOAc/hexanes) gave impure title compound (767 mg, 2.295 mmol, 58.3% yield). This crude material was dissolved in MeOH (2.2 ml), cooled to <5° C., and sodium borohydride (12.56 mg, 0.332 mmol) was added. After the addition, LCMS showed complete conversion. 2N HCl (50 mL) was added and the mixture was extracted with MTBE (50 mL). The organic layer was washed with water (50 mL), and the aqueous layer was basified with 2N NaOH (60 mL), and extracted with dichloromethane (50 mL×2) The dichloromethane layer was dried (Na$_2$SO$_4$), filtered, and concentrated to provide the title compound (48 mg, 0.143 mmol, 43.0% yield). $^1$H NMR (300 MHz, DMSO-d$_6$) δ ppm 8.39 (ddd, J=4.8, 1.8, 0.9 Hz, 1H), 7.55 (td, J=7.7, 1.8 Hz, 1H), 7.42 (d, J=8.3 Hz, 1H), 7.22-7.10 (m, 2H), 6.99 (d, J=2.1 Hz, 1H), 6.77 (d, J=7.9 Hz, 1H), 6.70 (dd, J=8.3, 2.1 Hz, 1H), 5.65 (d, J=4.4 Hz, 1H), 4.92 (d, J=4.3 Hz, 1H), 2.62-2.82 (m, 2H), 2.07-2.27 (m, 2H), 1.99 (s, 1H), 1.64-1.78 (m, 1H). MS (DCI$^+$) M/Z (M+H)$^+$ 336.

Example 44

{1-[1-(3-chlorophenyl)ethyl]cyclobutyl}(pyridin-2-yl)methanol

Example 44A 1-(1-bromoethyl)-3-chlorobenzene

To a solution of 1-(3-chlorophenyl)ethanol (0.2 g, 1.28 mmol) in diethyl ether (10 mL) at 0° C. was added tribromophosphine (0.38 g, 1.41 mmol). The mixture was warmed to room temperature and stirred overnight, then diluted with ether (10 mL). After quenching with water (10 mL), the organic phase was separated, dried over Na$_2$SO$_4$, filtered and concentrated. The residue was purified by column chromatography on silica gel and eluted with petroleum ether to give the title compound as an oil (0.16 g, yield 57.1%).

Example 44B 1-(1-(3-chlorophenyl)ethyl)cyclobutanecarbonitrile n-BuLi (4.7 mL, 11.8 mmol, 2.5 M in hexane) was added to a solution of diisopropylamine (1.13 g, 11.2 mmol) in THF (20 mL) at −78° C. After stirring for 5 min, neat cyclobutanecarbonitrile (0.8 g, 9.87 mmol) was added and the mixture was stirred at −78° C. for 1 hour. Then a solution of Example 44A (2.6 g, 11.8 mmol) in THF (10 mL) was added and the mixture was stirred at −78° C. for 1 h. The mixture was quenched with water and extracted with EtOAc (40 mL). The solvent was evaporated and the residue was used directly in the next step without further purification. LC-MS: m/z 220 (M+H).

Example 44C (1-(3-chlorobenzyl)cyclobutyl)(pyridin-2-yl)methanone

To a solution of 2-bromopyridine (1.1 g, 6.85 mmol) was added n-BuLi (2.7 mL, 6.85 mmol 2.5M in hexane) at −78° C. After stirring for 15 min, a solution of Example 44B (1.0 g, 4.57 mmol) in THF (20 mL) was added. The mixture was stirred at −78° C. for 15 min. followed by slow addition of 9.1 mL of 1 M H$_2$SO$_4$. The mixture was then heated to 50° C. and stirred for 30 min. The aqueous phase was separated and extracted with EtOAc (30 mL).

The combined organic phases were washed with water, brine, dried over Na$_2$SO$_4$, filtered, and concentrated. The residue was used in the next step without further purification. LC-MS: m/z 300 (M+H).

Example 44D

{1-[1-(3-chlorophenyl)ethyl]cyclobutyl}(pyridin-2-yl)methanol

To a solution of Example 44C (0.5 g, 1.67 mmol) in 20 mL of methanol was added NaBH$_4$ (0.076 g, 2 mmol) in small portions at 0° C. The mixture was stirred at 0° C. for 2 h. The mixture was concentrated and the residue was purified by prep TLC (petroleum ether: ethyl acetate=7:1) to afford the title compound (0.35 g, total yield 23.6%). $^1$H NMR (400 MHz, CDCl$_3$): δ=8.58 (d, J=2.0 Hz, 1H), 7.65-7.62 (m, 1H), 7.27-7.12 (m, 6H), 4.78 (s, 1H), 4.16 (brs, 1H), 3.12-3.00 (m, 1H), 2.17-1.80 (m, 4H), 1.36 (d, J=6.0 Hz, 3H), 1.26-1.17 (m, 1H), 0.95-0.80 (m, 1H). LC-MS: m/z 302 (M+H).

Example 45

{1-[1-(2-methylphenyl)ethyl]cyclobutyl}(pyridin-2-yl)methanol

Example 45A 1-(1-bromoethyl)-2-methylbenzene

The title compound was prepared according to the procedure of Example 44A, substituting 1-o-tolylethanol for 1-(3-chlorophenyl)ethanol.

Example 45B 1-(1-o-tolylethyl)cyclobutanecarbonitrile

The title compound was prepared according to the procedure of Example 44B, substituting Example 45A for Example 44A. LC-MS: m/z 200 (M+H).

Example 45C pyridin-2-yl(1-(1-o-tolylethyl)cyclobutyl)methanone

The title compound was prepared according to the procedure of Example 44C, substituting Example 45B for Example 44B. LC-MS: m/z 280 (M+H).

Example 45D

{1-[1-(2-methylphenyl)ethyl]cyclobutyl}(pyridin-2-yl)methanol

The title compound was prepared according to the procedure of Example 44D, substituting Example 45C for Example 44C. $^1$H NMR (400 MHz, CDCl$_3$): δ ppm 8.57 (d, J=4.8 Hz, 1H), 7.65-7.6 (m, 1H), 7.33-7.09 (m, 6H), 4.89 (s, 1H), 4.41 (brs, 1H), 3.21 (q, 1H), 2.06-1.98 (m, 6H), 1.67-1.62 (m, 1H), 1.31 (d, J=6.8 Hz, 3H), 1.25-1.19 (m, 1H), 0.91-0.84 (m, 1H). LC-MS: m/z 282 (M+H).

Example 46

{1-[1-(4-fluorophenyl)ethyl]cyclobutyl}(pyridin-2-yl)methanol

Example 46A 1-(1-bromoethyl)-4-fluorobenzene

The title compound was prepared according to the procedure of Example 44A, substituting 1-(4-fluorophenyl)ethanol for 1-(3-chlorophenyl)ethanol.

Example 46B 1-(1-(4-fluorophenyl)ethyl)cyclobutanecarbonitrile

The title compound was prepared according to the procedure of Example 44B, substituting Example 46A for Example 44A. LC-MS: m/z 204 (M+H).

Example 46C (1-(1-(4-fluorophenyl)ethyl)cyclobutyl)(pyridin-2-yl)methanone

The title compound was prepared according to the procedure of Example 44C, substituting Example 46B for Example 44B. LC-MS: m/z 284 (M+H).

Example 46D

{1-[1-(4-fluorophenyl)ethyl]cyclobutyl}(pyridin-2-yl)methanol

The title compound was prepared according to the procedure of Example 44D, substituting Example 46C for Example 44C. $^1$H NMR (400 MHz, d-MeOH): δ ppm 8.49-8.44 (m, 1H), 7.85-7.81 (m, 1H), 7.68-7.62 (m, 1H), 7.35-7.24 (m, 3H), 7.04-6.98 (m, 2H), 4.77 (s, 1H), 3.33-3.22 (m, 5H), 2.23-1.98 (m, 1H), 1.83-1.76 (m, 1H), 1.38 (d, J=7.2 Hz, 3H), 1.12-1.04 (m, 1H), 0.80-0.70 (m, 1H); LC-MS: m/z 286 (M+H).

Example 47

{1-[1-(3-fluorophenyl)ethyl]cyclobutyl}(pyridin-2-yl)methanol

Example 47A 1-(1-bromoethyl)-3-fluorobenzene

The title compound was prepared according to the procedure of Example 44A, substituting 1-(3-fluorophenyl)ethanol for 1-(3-chlorophenyl)ethanol.

Example 47B 1-(1-(3-fluorophenyl)ethyl)cyclobutanecarbonitrile

The title compound was prepared according to the procedure of Example 44B, substituting Example 47A for Example 44A. LC-MS: m/z 204 (M+H).

Example 47C (1-(1-(3-fluorophenyl)ethyl)cyclobutyl)(pyridin-2-yl)methanone

The title compound was prepared according to the procedure of Example 44C, substituting Example 47B for Example 44B. LC-MS: m/z 284 (M+H).

Example 47D

{1-[1-(3-fluorophenyl)ethyl]cyclobutyl}(pyridin-2-yl)methanol

The title compound was prepared according to the procedure of Example 44D, substituting Example 47C for Example 44C. $^1$H NMR (400 MHz, CDCl$_3$): δ ppm 8.58-8.57 (m, 1H), 7.65-7.61 (m, 1H), 7.27-7.17 (m, 3H), 7.05-6.87 (m, 3H), 4.77 (s, 1H), 4.44 (brs, 1H), 3.14-3.00 (m, 1H), 2.20-1.77 (m, 4H), 1.36 (d, J=7.6 Hz, 3H), 1.26-1.17 (m, 1H), 0.94-0.80 (m, 1H); LC-MS: m/z 286 (M+H).

Example 48

{1-[1-(2-fluorophenyl)ethyl]cyclobutyl}(pyridin-2-yl)methanol

Example 48A 1-(1-bromoethyl)-2-fluorobenzene

The title compound was prepared according to the procedure of Example 44A, substituting 1-(2-fluorophenyl)ethanol for 1-(3-chlorophenyl)ethanol.

Example 48B 1-(1-(2-fluorophenyl)ethyl)cyclobutanecarbonitrile

The title compound was prepared according to the procedure of Example 44B, substituting Example 48A for Example 44A. LC-MS: m/z 204 (M+H).

Example 48C (1-(1-(2-fluorophenyl)ethyl)cyclobutyl)(pyridin-2-yl)methanone

The title compound was prepared according to the procedure of Example 44C, substituting Example 48B for Example 44B. LC-MS: m/z 284 (M+H).

Example 48D

{1-[1-(2-fluorophenyl)ethyl]cyclobutyl}(pyridin-2-yl)methanol

The title compound was prepared according to the procedure of Example 44D, substituting Example 48C for Example 44C. $^1$H NMR (400 MHz, CD$_3$OD): δ ppm 8.28 (d, J=4.4 Hz, 1H), 7.67-7.62 (m, 1H), 7.51-7.46 (m, 1H), 7.30-7.26 (m, 1H), 7.16-6.97 (m, 3H), 6.90-6.85 (m, 1H), 4.74 (s, 1H), 3.43 (q, 1H), 2.23-1.75 (m, 3H), 1.65-1.57 (m, 1H), 1.22 (d, J=7.2 Hz, 3H), 1.12-1.04 (m, 1H), 0.71-0.63 (m, 1H); LC-MS: m/z 286 (M+H).

Example 49

{1-[1-(4-chlorophenyl)ethyl]cyclobutyl}(pyridin-2-yl)methanol

Example 49A 1-(1-bromoethyl)-4-chlorobenzene

The title compound was prepared according to the procedure of Example 44A, substituting 1-(4-chlorophenyl)ethanol for 1-(3-chlorophenyl)ethanol.

Example 49B 1-(1-(4-chlorophenyl)ethyl)cyclobutanecarbonitrile

The title compound was prepared according to the procedure of Example 44B, substituting Example 49A for Example 44A. LC-MS: m/z 220 (M+H).

Example 49C (1-(1-(4-chlorophenyl)ethyl)cyclobutyl)(pyridin-2-yl)methanone

The title compound was prepared according to the procedure of Example 44C, substituting Example 49B for Example 44B. LC-MS: m/z 300 (M+H).

Example 49D

{1-[1-(4-chlorophenyl)ethyl]cyclobutyl}(pyridin-2-yl)methanol

The title compound was prepared according to the procedure of Example 44D, substituting Example 49C for Example 44C. $^1$H NMR (400 MHz, CDCl$_3$): δ ppm 8.58 (d, J=4.8 Hz, 1H), 7.68-7.64 (m, 1H), 7.27-7.16 (m, 6H), 4.78 (s, 1H), 3.11-3.00 (m, 1H), 2.20-1.76 (m, 4H), 1.36 (d, J=6.8 Hz, 3H), 1.26-1.17 (m, 1H), 0.94-0.80 (m, 1H); LC-MS: m/z 302 (M+H).

Example 50

{1-[1-(2-chlorophenyl)ethyl]cyclobutyl}(pyridin-2-yl)methanol

Example 50A 1-(1-bromoethyl)-2-chlorobenzene

The title compound was prepared according to the procedure of Example 44A, substituting 1-(2-chlorophenyl)ethanol for 1-(3-chlorophenyl)ethanol.

Example 50B 1-(1-(2-chlorophenyl)ethyl)cyclobutanecarbonitrile

The title compound was prepared according to the procedure of Example 44B, substituting Example 50A for Example 44A. LC-MS: m/z 220 (M+H).

Example 50C (1-(1-(2-chlorophenyl)ethyl)cyclobutyl)(pyridin-2-yl)methanone

The title compound was prepared according to the procedure of Example 44C, substituting Example 50B for Example 44B. LC-MS: m/z 300 (M+H).

Example 50D

{1-[1-(2-chlorophenyl)ethyl]cyclobutyl}(pyridin-2-yl)methanol

The title compound was prepared according to the procedure of Example 44D, substituting Example 50C for Example 44C. $^1$H NMR (400 MHz, CDCl$_3$): δ ppm 8.56 (d, J=4.8 Hz, 1H), 7.64-7.60 (m, 1H), 7.42-7.33 (m, 2H), 7.27-7.07 (m, 4H), 4.88 (s, 1H), 4.47 (brs, 1H), 3.38 (q, 1H), 2.35-1.85 (m, 4H), 1.41-1.22 (m, 5H); LC-MS: m/z 302 (M+H).

Example 51

[1-(1-phenylethyl)cyclobutyl](pyridin-2-yl)methanol

Example 51A 1-(1-phenylethyl)cyclobutanecarbonitrile
The title compound was prepared according to the procedure of Example 44B, substituting (1-bromoethyl)benzene for Example 44A. LC-MS: m/z 186 (M+H).

Example 51B (1-(1-phenylethyl)cyclobutyl)(pyridin-2-yl)methanone

The title compound was prepared according to the procedure of Example 44C, substituting Example 51A for Example 44B. LC-MS: m/z 266 (M+H).

Example 51C

[1-(1-phenylethyl)cyclobutyl](pyridin-2-yl)methanol

The title compound was prepared according to the procedure of Example 44D, substituting Example 51B for Example 44C. ¹H NMR (400 MHz, CDCl₃): δ ppm 8.57 (d, J=2.8 Hz, 1H), 7.64-7.61 (m, 1H), 7.31-7.15 (m, 7H), 4.80 (s, 1H), 4.38 (brs, 1H), 2.99 (q, 1H), 2.20-1.82 (m, 4H), 1.38 (d, J=5.6 Hz, 3H), 1.21-1.17 (m, 1H), 0.94-0.81 (m, 1H). LC-MS: m/z 268 (M+H).

Example 52

[1-(4-methylbenzyl)cyclobutyl](pyridin-2-yl)methanol

Example 52A (E)-3-p-tolylbut-2-enenitrile

To a solution of diethyl cyanomethylphosphonate (13.2 g, 74.6 mmol) in 50 mL of THF was added sodium hydride (60% content, 2.98 g, 74.6 mmol). The mixture was stirred at room temperature for 2 hours. 1-(4-methylphenyl)ethanone (5 g, 37.3 mmol) was added and the mixture was stirred for 2 hours. After evaporation of THF, the residue was taken up in ethyl acetate (50 mL) and quenched with water (50 mL). The organic phase was washed with water (50 mL), dried over Na₂SO₄ and filtered. The filtrate was concentrated in vacuo, and the residue was used in the next step without further purification. LC-MS: m/z 158 (M+H).

Example 52B 3-p-tolylbutanenitrile

To a solution of Example 52A (4.3 g, 27.4 mmol) in 50 mL of THF, 5% Pd/C (0.4 g) was added, the mixture was hydrogenated at room temperature overnight, then filtered.

The filtrate was concentrated and the residue was purified by chromatography (silica gel, eluted with petroleum ether:ethyl acetate=10:1) to afford the title compound (4 g, yield 67.5%, two steps) as an oil. LC-MS: m/z 160 (M+H).

Example 52C 1-(1-p-tolylethyl)cyclobutanecarbonitrile n-BuLi (2.5 M in hexane, 3.4 mL, 8.5 mmol) was added to a solution of diisopropylamine (0.86 g, 8.5 mmol) in THF (60 mL) at −78° C. After stirring for 15 min., Example 52B (0.5 g, 3.2 mmol) was added and the mixture was stirred at −78° C. for 1 h. Then 1,3-dibromopropane (0.75 g, 3.8 mmol) was added and the mixture was stirred at −78° C. for 2 h. The mixture was concentrated and the residue was taken up in ethyl acetate (60 mL) and water (60 mL). The organic phase was washed with brine (60 mL), dried over Na₂SO₄, filtered, and concentrated in vacuo. The residue was purified by column chromatography (silica gel, eluted with petroleum ether:ethyl acetate=10:1) to afford the title compound (0.3 g, yield 47.6%) as an oil. LC-MS: m/z 200 (M+H).

Example 52D pyridin-2-yl(1-(1-p-tolylethyl)cyclobutyl)methanone

The title compound was prepared according to the procedure of Example 44C, substituting Example 52C for Example 44B. LC-MS: m/z 280 (M+H), Example 52E

[1-(4-methylbenzyl)cyclobutyl](pyridin-2-yl)methanol

The title compound was prepared according to the procedure of Example 44D, substituting Example 52D for Example 44C. ¹H NMR (400 MHz, CDCl₃): δ ppm 8.55 (d, J=5.2 Hz, 1H), 7.62-7.57 (m, 1H), 7.22-7.07 (m, 6H), 4.78 (s, 1H), 4.36 (brs, 1H), 2.95 (q, 1H), 2.32-2.30 (m, 3H), 2.18-1.93 (m, 4H), 1.36-1.31 (m, 3H), 1.29-1.15 (m, 1H), 0.94-0.81 (m, 1H). LC-MS: m/z 282 (M+H), RT (3 min):1.72 min.

Example 53 pyridin-2-yl(1-{1-[4-(trifluoromethyl)phenyl]ethyl}cyclobutyl)methanol

Example 53A (E)-3-(4-(trifluoromethyl)phenyl)but-2-enenitrile

The title compound was prepared according to the procedure of Example 52A, substituting 1-(4-(trifluoromethyl)phenyl)ethanone for 1-(4-methylphenyl)ethanone. LC-MS: m/z 212 (M+H).

Example 53B 3-(4-(trifluoromethyl)phenyl)butanenitrile

The title compound was prepared according to the procedure of Example 52B, substituting Example 53A for Example 52A. LC-MS: m/z 214 (M+H).

Example 53C 1-(1-(4-(trifluoromethyl)phenyl)ethyl)cyclobutanecarbonitrile

The title compound was prepared according to the procedure of Example 52C, substituting Example 53B for Example 52B. LC-MS: m/z 254 (M+H).

Example 53D pyridin-2-yl(1-(1-(4-(trifluoromethyl)phenyl)ethyl)cyclobutyl)methanone The title compound was prepared according to the procedure of Example 44C, substituting Example 53C for Example 44B. LC-MS: m/z 334 (M+H).

Example 53E pyridin-2-yl(1-{1-[4-(trifluoromethyl)phenyl]ethyl}cyclobutyl)methanol The title compound was prepared according to the procedure of Example 44D, substituting Example 53D for Example 44C. ¹H NMR (400 MHz, CDCl₃): δ ppm 8.56 (d, J=4.8 Hz, 1H), 7.64-7.59 (m, 1H), 7.53 (d, J=8.0 Hz, 2H), 7.35 (d, J=8.0 Hz, 2H), 7.23-7.16 (m, 2H), 4.76 (s, 1H), 4.46 (brs, 1H), 3.12 (q, 1H), 2.20-1.74 (m, 4H), 1.38 (d, J=6.8 Hz, 3H), 1.21-1.14 (m, 1H), 0.92-0.84 (m, 1H); LC-MS: m/z 336 (M+H).

Example 54 pyridin-2-yl(1-{1-[3-(trifluoromethyl)phenyl]ethyl}cyclobutyl)methanol

Example 54A (E)-3-(3-(trifluoromethyl)phenyl)but-2-enenitrile

The title compound was prepared according to the procedure of Example 52A, substituting 1-(3-(trifluoromethyl)phenyl)ethanone for 1-(4-methylphenyl)ethanone. LC-MS: m/z 212 (M+H).

Example 54B 3-(3-(trifluoromethyl)phenyl)butanenitrile

The title compound was prepared according to the procedure of Example 52B, substituting Example 54A for Example 52A. LC-MS: m/z 214 (M+H).

Example 54C 1-(1-(3-(trifluoromethyl)phenyl)ethyl)cyclobutanecarbonitrile

The title compound was prepared according to the procedure of Example 52C, substituting Example 54B for Example 52B. LC-MS: m/z 254 (M+H).

Example 54D pyridin-2-yl(1-(1-(3-(trifluoromethyl)phenyl)ethyl)cyclobutyl)methanone The title compound was prepared according to the procedure of Example 44C, substituting Example 54C for Example 44B. LC-MS: m/z 334 (M+H).

Example 54E pyridin-2-yl(1-{1-[3-(trifluoromethyl)phenyl]ethyl}cyclobutyl)methanol The title compound was prepared according to the procedure of Example 44D, substituting Example 54D for Example 44C. $^1$H NMR (400 MHz, CDCl$_3$): δ ppm 8.56 (d, J=4.8 Hz, 1H), 7.69-7.64 (m, 1H), 7.46-7.37 (m, 4H), 7.25-7.19 (m, 2H), 4.77 (s, 1H), 3.12 (q, 1H), 2.21-1.77 (m, 4H), 1.38 (d, J=6.8 Hz, 3H), 1.21-1.11 (m, 1H), 0.92-0.88 (m, 1H); LC-MS: m/z 336 (M+H).

Example 55

[1-(2,3-dihydro-1H-inden-1-yl)cyclobutyl](pyridin-2-yl)methanol

Example 55A (E)-2-(2,3-dihydro-1H-inden-1-ylidene)acetonitrile

The title compound was prepared according to the procedure of Example 52A, substituting 2,3-dihydro-1H-inden-1-one for 1-(4-methylphenyl)ethanone. LC-MS: m/z 156 (M+H).

Example 55B 2-(2,3-dihydro-1H-inden-1-yl)acetonitrile

The title compound was prepared according to the procedure of Example 52B, substituting Example 55A for Example 52A. LC-MS: m/z 158 (M+H).

Example 55C 1-(2,3-dihydro-1H-inden-1-yl)cyclobutanecarbonitrile

The title compound was prepared according to the procedure of Example 52C, substituting Example 55B for Example 52B. LC-MS: m/z 198 (M+H).

Example 55D (1-(2,3-dihydro-1H-inden-1-yl)cyclobutyl)(pyridin-2-yl)methanone The title compound was prepared according to the procedure of Example 44C, substituting Example 55C for Example 44B. LC-MS: m/z 278 (M+H).

Example 55E

[1-(2,3-dihydro-1H-inden-1-yl)cyclobutyl](pyridin-2-yl)methanol

The title compound was prepared according to the procedure of Example 44D, substituting Example 55D for Example 44C. $^1$H NMR (400 MHz, CD$_3$OD): δ ppm 8.57-8.38 (m, 1H), 8.26-8.21 (m, 1H), 7.79-7.69 (m, 2H), 7.08-6.82 (m, 4H), 5.17 (s, 1H), 3.60-3.48 (m, 1H), 2.92-2.58 (m, 2H), 2.35-1.89 (m, 5H), 1.76-1.10 (m, 3H); LC-MS: m/z 280 (M+H).

Example 56 pyridin-2-yl[1-(1,2,3,4-tetrahydronaphthalen-1-yl)cyclobutyl]methanol

Example 56A (E)-2-(3,4-dihydronaphthalen-1(2H)-ylidene)acetonitrile

The title compound was prepared according to the procedure of Example 52A, substituting 3,4-dihydronaphthalen-1(2H)-one for 1-(4-methylphenyl)ethanone. LC-MS: m/z 170 (M+H).

Example 56B 2-(1,2,3,4-tetrahydronaphthalen-1-yl)acetonitrile

The title compound was prepared according to the procedure of Example 52B, substituting Example 56A for Example 52A. LC-MS: m/z 172 (M+H).

Example 56C 1-(1,2,3,4-tetrahydronaphthalen-1-yl)cyclobutanecarbonitrile

The title compound was prepared according to the procedure of Example 52C, substituting Example 56B for Example 52B. LC-MS: m/z 212 (M+H).

Example 56D pyridin-2-yl(1-(1,2,3,4-tetrahydronaphthalen-1-yl)cyclobutyl)methanone The title compound was prepared according to the procedure of Example 44C, substituting Example 56C for Example 44B. LC-MS: m/z 292 (M+H).

Example 56E pyridin-2-yl[1-(1,2,3,4-tetrahydronaphthalen-1-yl)cyclobutyl]methanol The title compound was prepared according to the procedure of Example 44D, substituting Example 56D for Example 44C. $^1$H NMR (400 MHz, CD$_3$OD): δ ppm 8.49-8.46 (m, 1H), 7.82-760 (m, 2H), 7.37-6.96 (m, 5H), 4.97 (s, 1H), 3.21-3.07 (m, 1H), 2.87-2.52 (m, 2H), 2.41-1.05 (m, 10H); LC-MS: m/z 294 (M+H).

Example 57

[1-(3,4-dihydro-2H-chromen-4-yl)cyclobutyl](pyridin-2-yl)methanol

Example 57A (E)-2-(chroman-4-ylidene)acetonitrile

The title compound was prepared according to the procedure of Example 52A, substituting chroman-4-one for 1-(4-methylphenyl)ethanone. LC-MS: m/z 172 (M+H).

Example 57B 2-(chroman-4-yl)acetonitrile

The title compound was prepared according to the procedure of Example 52B, substituting Example 57A for Example 52A. LC-MS: m/z 174 (M+H).

Example 57C 1-(chroman-4-yl)cyclobutanecarbonitrile

The title compound was prepared according to the procedure of Example 52C, substituting Example 57B for Example 52B. LC-MS: m/z 214 (M+H).

Example 57D (1-(chroman-4-yl)cyclobutyl)(pyridin-2-yl)methanone

The title compound was prepared according to the procedure of Example 44C, substituting Example 57C for Example 44B. LC-MS: m/z 294 (M+H).

Example 57

[1-(3,4-dihydro-2H-chromen-4-yl)cyclobutyl](pyridin-2-yl)methanol

The title compound was prepared according to the procedure of Example 44D, substituting Example 57D for Example 44C. $^1$H NMR (400 MHz, CDCl$_3$): δ ppm 8.58 (d, J=4.8 Hz, 1H), 7.67-7.63 (m, 1H), 7.33 (d, J=8.0 Hz, 1H), 7.25-7.22 (m, 1H), 7.13-7.09 (m, 1H), 7.04 (d, J=8.0 Hz, 1H), 6.79-6.84 (m, 2H), 4.77 (s, 1H), 4.41 (brs, 1H), 4.36-4.30 (m, 1H), 4.18-4.13 (m, 1H), 3.11 (t, J=6.0, 1H), 2.43-1.92 (m, 6H), 1.37-1.30 (m, 1H), 0.89-0.81 (m, 1H). LC-MS: m/z 296 (M+H).

Example 58 pyridin-2-yl[1-(2,2,2-trifluoro-1-phenylethyl)cyclobutyl]methanol

Example 58A (Z)-4,4,4-trifluoro-3-phenylbut-2-enenitrile

To a solution of diethyl cyanomethylphosphonate (6.1 g, 34.5 mmol) in 15 mL of THF was added sodium hydride (60% content, 1.4 g, 34.5 mmol). The mixture was stirred at room temperature. for 2 hours. 2,2,2-Trifluoro-1-phenylethanone (3 g, 17.2 mmol) was added and the mixture was stirred for 4 hours. After evaporation of THF, the residue was taken up in ethyl acetate (100 mL) and quenched with water (50 mL). The organic phase was washed with water (100 mL), dried over Na$_2$SO$_4$ and filtered. The filtrate was concentrated in vacuo and the residue was purified by silica gel column chromatography (petrol ether: ethyl acetate=10:1) to afford the title compound (1.5 g, yield 29%) as an oil. LC-MS: m/z 198 (M+H).

Example 58B 4,4,4-trifluoro-3-phenylbutanenitrile

To a mixture of compound Example 58A (2.9 g, 15 mmol) in 60 mL of methanol at 0° C., was added sodium borohydride (1.7 g, 45 mmol). The mixture was stirred at room temperature for 4 h. The solvent was evaporated in vacuo and the residue was purified by silica gel column chromatography (petroleum ether: ethyl acetate=10:1) to afford the title compound (2 g, yield 69%) as an oil. LC-MS: m/z 200 (M+H).

Example 58C 1-(2,2,2-trifluoro-1-phenylethyl)cyclobutanecarbonitrile

The title compound was prepared according to the procedure of Example 52C, substituting Example 58B for Example 52B. LC-MS: m/z 240 (M+H).

Example 58D pyridin-2-yl(1-(2,2,2-trifluoro-1-phenylethyl)cyclobutyl)methanone To a solution of Example 58C (0.4 g, 1.67 mmol) in 12 mL of dichloromethane at −78° C. was added diisobutylaluminum hydride (1 M in toluene, 3.3 mL, 3.3 mmol). The mixture was stirred at −78 for 1 h., then warmed to −40° C. and stirred for 0.5 h. Brine (12 mL) was added and the layers were separated. The aqueous phase extracted with dichloromethane (20 mL). The combined organic phases were dried over $Na_2SO_4$, filtered and concentrated in vacuo. The residue was purified by prep-TLC (petroleum ether: ethyl acetate=10:1) to afford the title compound (0.25 g, yield 61.8%) as an oil. LC-MS: m/z 244 (M+H).

Example 58E pyridin-2-yl[1-(2,2,2-trifluoro-1-phenylethyl)cyclobutyl]methanol

To a solution of 2-bromopyridine (0.36 g, 2.28 mmol) in 15 mL of THF at −78° C. was added n-BuLi (0.9 mL, 2.26 mmol 2.5M in hexane). The mixture was stirred at −78° C. for 15 min., then compound Example 58D (0.25 g, 1.03 mmol) was added and the mixture was stirred for 1 h. at −78° C. After warming to room temperature, 15 mL of water was added to quench the reaction. The mixture was extracted with ethyl acetate (30 mL), washed with brine (30 mL), dried over $Na_2SO_4$, and filtered. The filtrate was concentrated in vacuo and the residue was purified by prep-TLC (petroleum ether: ethyl acetate=1:1) to give the title compound (30 mg, yield 9.3%). $^1$H NMR (400 MHz, $CD_3OD$): δ ppm 8.64 (d, J=5.6 Hz, 1H), 8.38-8.34 (m, 1H), 7.96 (d, J=8.4 Hz, 1H), 7.85 (t, J=6.8, 1H), 7.27-7.32 (m, 5H), 4.59 (s, 1H), 3.92 (q, 1H), 2.66-2.52 (m, 2H), 2.18-2.12 (m, 1H), 1.77-1.72 (m, 1H), 1.54-1.45 (m, 1H), 0.46-0.34 (m, 1H). LC-MS: m/z 322 (M+H).

Example 59

[4-(3,4-dichlorophenyl)tetrahydro-2H-pyran-4-yl](pyridin-2-yl)methanol

Example 59A 4-(3,4-dichlorophenyl)tetrahydro-2H-pyran-4-carbonitrile

NaH (420 mg, 10.5 mmol, 60%, w/w) was added to a solution of 2-(3,4-dichlorophenyl)acetonitrile (930 mg, 5 mmol) in DMSO (20 ml) at room temperature. After stirring for 40 minutes at room temperature (15° C.), 1-chloro-2-(2-chloroethoxy)ethane (786.5 mg, 5.5 mmol) was added. The mixture was stirred for another 1 hour, then poured into water (5.0 mL), and the mixture was extracted with EtOAc-toluene (2:1, 3×30 mL). The combined organic extracts were washed with 2N aq. HCl (30 mL), water (30 mL) and brine (30 mL), dried over $MgSO_4$, filtered, and concentrated to 5 mL. The precipitated solids were collected by filtration and washed with cold diethylether (10 mL) to afford the title compound (450 mg, yield 35%). $^1$H NMR (400 MHz, $CDCl_3$): 7.58 (d, J=2.0 Hz, 1H), 7.52 (d, J=1.6 Hz, 1H), 7.34 (dd, J=2.0 Hz, J=8.8 Hz, 1H), 4.08-4.12 (m, 2H), 3.85-3.92 (m, 2H), 2.2.02-2.13 (m, 4H). LC-MS (M+H): m/z 229.1 (M-CN).

Example 59B (4-(3,4-dichlorophenyl)tetrahydro-2H-pyran-4-yl)(pyridin-2-yl)methanone To a solution of 2-bromopyridine (418 mg, 2.65 mmol) in THF (10 mL) was added n-BuLi (1.65 ml, 2.65 mmol, 1.6 N in hexane) at −78° C. After 15 minutes, Example 59A (450 mg, 1.76 mmol) in THF (2 mL) was added. The mixture was stirred at −78° C. for 15 min and 2 mL of 1 M $H_2SO_4$ was added slowly. Then the mixture was heated at 50° C.-60° C. for 30 minutes. The aqueous phase was separated and extracted with EtOAc. The combined organic phase was washed with water, brine, dried over $Na_2SO_4$, filtered, and concentration gave the title compound, which was used directly for the next reaction (600 mg, 100% yield). LC-MS: m/z 336.1 (M+H).

Example 59C

[4-(3,4-dichlorophenyl)tetrahydro-2H-pyran-4-yl](pyridin-2-yl)methanol

To a solution of compound Example 59B (600 mg, 1.79 mmol) in methanol (10 ml) was added $NaBH_4$ (135 mg, 3.55 mmol) portionwise, and the mixture was stirred overnight at room temperature. After evaporation of most of the solvent and dilution with 10 mL of water, the mixture was extracted with ethyl acetate and the organic phase was dried over $Na_2SO_4$, filtered, and concentrated in vacuo. The residue was purified by prep-TLC (petroleum ether:ethyl acetate=1:1) to give title compound (300 mg, 50% yield). $^1$H NMR (400 MHz, $CDCl_3$): 8.38 (d, J=4.8 Hz, 1H), 7.54 (td, J=2.0 Hz, J=7.6 Hz, 1H), 7.31 (d, J=8.4 Hz, 1H), 7.15-7.18 (m, 1H), 7.03 (d, J=8.4 Hz, 1H), 6.84 (dd, J=2.4 Hz, J=8.8 Hz, 1H), 6.71 (d, J=7.6 Hz, 1H), 4.61 (s, 1H), 4.39 (br, 1H), 3.82-3.89 (m, 2H), 3.28-3.41 (m, 2H), 2.02-2.28 (m, 4H). LC-MS: m/z 338.1 (M+H).

Example 60

(4-phenyltetrahydro-2H-pyran-4-yl)(pyridin-2-yl)methanol

Example 60A 4-phenyltetrahydro-2H-pyran-4-carbonitrile

The title compound was prepared according to the procedure of Example 59A, substituting 2-phenylacetonitrile for 2-(3,4-dichlorophenyl)acetonitrile.

Example 60B (4-phenyltetrahydro-2H-pyran-4-yl)(pyridin-2-yl)methanone

The title compound was prepared according to the procedure of Example 59B, substituting Example 60A for Example 59A.

Example 60C (4-phenyltetrahydro-2H-pyran-4-yl)(pyridin-2-yl)methanol

The title compound was prepared according to the procedure of Example 59C, substituting Example 60B for Example 59B. $^1$H NMR (400 MHz, $CDCl_3$): 8.38 (d, J=4.4 Hz, 1H), 7.22-7.41 (m, 5H), 7.03-7.11 (m, 3H), 6.34 (d, J=7.6 Hz, 1H), 4.64 (d, J=6.4 Hz, 1H), 4.70 (d, J=6.8 Hz, 1H), 3.81-3.86 (m, 2H), 3.30-3.49 (m, 2H), 2.35-2.41 (m, 1H), 1.99-2.18 (m, 3H).

Example 61

[4-(3-fluorophenyl)tetrahydro-2H-pyran-4-yl](pyridin-2-yl)methanol

Example 61A 4-(3-fluorophenyl)tetrahydro-2H-pyran-4-carbonitrile

The title compound was prepared according to the procedure of Example 59A, substituting 2-(3-fluorophenyl)acetonitrile for 2-(3,4-dichlorophenyl)acetonitrile.

Example 61B (4-(3-fluorophenyl)tetrahydro-2H-pyran-4-yl)(pyridin-2-yl)methanone The title compound was prepared according to the procedure of Example 59B, substituting Example 61A for Example 59A.

Example 61C

[4-(3-fluorophenyl)tetrahydro-2H-pyran-4-yl](pyridin-2-yl)methanol

The title compound was prepared according to the procedure of Example 59C, substituting Example 61B for Example 59B. $^1$H NMR (400 MHz, CDCl$_3$): 8.39 (d, J=4.4 Hz, 1H), 7.46 (td, J=1.6 Hz, J=7.6 Hz, 1H), 7.11-7.25 (m, 2H), 6.90-6.95 (m, 1H), 6.82 (d, J=7.6 Hz, 1H), 6.73 (dt, J=2.0 Hz, J=11.6 Hz, 1H), 6.51 (d, J=7.6 Hz, 1H), 4.62 (s, 1H), 4.48 (br, 1H), 3.82-3.88 (m, 2H), 3.29-3.46 (m, 2H), 2.30-2.38 (m, 1H), 2.04-2.18 (m, 3H).

Example 62

[4-(4-fluorophenyl)tetrahydro-2H-pyran-4-yl](pyridin-2-yl)methanol

Example 62A 4-(4-fluorophenyl)tetrahydro-2H-pyran-4-carbonitrile

The title compound was prepared according to the procedure of Example 59A, substituting 2-(4-fluorophenyl)acetonitrile for 2-(3,4-dichlorophenyl)acetonitrile.

Example 62B (4-(4-fluorophenyl)tetrahydro-2H-pyran-4-yl)(pyridin-2-yl)methanone The title compound was prepared according to the procedure of Example 59B, substituting Example 62A for Example 59A.

Example 62C

[4-(4-fluorophenyl)tetrahydro-2H-pyran-4-yl](pyridin-2-yl)methanol

The title compound was prepared according to the procedure of Example 59C, substituting Example 62B for Example 59B. $^1$H NMR (400 MHz, CDCl$_3$): 8.38 (d, J=4.8 Hz, 1H), 7.46 (td, J=1.6 Hz, J=8 Hz, 1H), 7.11-7.14 (m, 1H), 6.91-6.98 (m, 4H), 6.51 (d, J=8 Hz, 1H), 4.62 (s, 1H), 4.45 (s, 1H), 3.81-3.88 (m, 2H), 3.29-3.45 (m, 2H), 2.29-2.37 (m, 1H), 2.05-2.18 (m, 3H).

Example 63

[4-(3,4-difluorophenyl)tetrahydro-2H-pyran-4-yl](pyridin-2-yl)methanol

Example 63A 4-(3,4-difluorophenyl)tetrahydro-2H-pyran-4-carbonitrile

The title compound was prepared according to the procedure of Example 59A, substituting 2-(3,4-difluorophenyl)acetonitrile for 2-(3,4-dichlorophenyl)acetonitrile.

Example 63B (4-(3,4-difluorophenyl)tetrahydro-2H-pyran-4-yl)(pyridin-2-yl)methanone The title compound was prepared according to the procedure of Example 59B, substituting Example 63A for Example 59A.

Example 63C

[4-(3,4-difluorophenyl)tetrahydro-2H-pyran-4-yl](pyridin-2-yl)methanol

The title compound was prepared according to the procedure of Example 59C, substituting Example 63B for Example 59B. $^1$H NMR (400 MHz, CDCl$_3$): 8.37 (d, J=4.4 Hz, 1H), 7.52 (td, J=1.2 Hz, J=7.6 Hz, 1H), 7.13-7.16 (m, 1H), 6.98-7.05 (m, 1H), 6.64-6.83 (m, 3H), 4.60 (s, 1H), 4.42 (br, 1H), 3.82-3.89 (m, 2H), 3.29-3.42 (m, 2H), 2.02-2.31 (m, 4H).

Example 64

[4-(4-chlorophenyl)tetrahydro-2H-pyran-4-yl](pyridin-2-yl)methanol

Example 64A 4-(4-chlorophenyl)tetrahydro-2H-pyran-4-carbonitrile

The title compound was prepared according to the procedure of Example 59A, substituting 2-(4-chlorophenyl)acetonitrile for 2-(3,4-dichlorophenyl)acetonitrile.

Example 64B (4-(4-chlorophenyl)tetrahydro-2H-pyran-4-yl)(pyridin-2-yl)methanone The title compound was prepared according to the procedure of Example 59B, substituting Example 64A for Example 59A.

Example 64C

[4-(4-chlorophenyl)tetrahydro-2H-pyran-4-yl](pyridin-2-yl)methanol

The title compound was prepared according to the procedure of Example 59C, substituting Example 64B for Example 59B. $^1$H NMR (400 MHz, CDCl$_3$): 8.38 (d, J=5.2 Hz, 1H), 7.48 (td, J=2.0 Hz, J=7.6 Hz, 1H), 7.30 (d, J=7.6 Hz, 2H), 7.11-7.14 (m, 1H), 6.96 (d, J=11.6 Hz, 2H), 6.55 (d, J=7.6 Hz, 1H), 4.61 (s, 1H), 4.44 (br, 1H), 3.80-3.87 (m, 2H), 3.27-3.43 (m, 2H), 2.28-2.35 (m, 1H), 2.08-2.17 (m, 3H).

Example 65 pyridin-2-yl {4-[4-(trifluoromethyl)phenyl]tetrahydro-2H-pyran-4-yl}methanol

Example 65A 4-(4-(trifluoromethyl)phenyl)tetrahydro-2H-pyran-4-carbonitrile

The title compound was prepared according to the procedure of Example 59A, substituting 2-(4-(trifluoromethyl)phenyl)acetonitrile for 2-(3,4-dichlorophenyl)acetonitrile.

Example 65B pyridin-2-yl(4-(4-(trifluoromethyl)phenyl)tetrahydro-2H-pyran-4-yl)methanone The title compound was prepared according to the procedure of Example 59B, substituting Example 65A for Example 59A.

Example 65C pyridin-2-yl {4-[4-(trifluoromethyl)phenyl]tetrahydro-2H-pyran-4-yl}methanol The title compound was prepared according to the procedure of Example 59C, substituting Example 65B for Example 59B. $^1$H NMR (400 MHz, CDCl$_3$): 8.34 (d, J=4.4 Hz, 1H), 7.46-7.50 (m, 3H), 7.12-7.14 (m, 3H), 6.60 (d, J=7.6 Hz, 1H), 4.65 (s, 1H), 4.45 (br, 1H), 3.83-3.89 (m, 2H), 3.27-3.14 (m, 2H), 2.13-2.34 (m, 4H).

Example 66 pyridin-2-yl {4-[3-(trifluoromethoxy)phenyl]tetrahydro-2H-pyran-4-yl}methanol

Example 66A 4-(3-(trifluoromethoxy)phenyl)tetrahydro-2H-pyran-4-carbonitrile The title compound was prepared according to the procedure of Example 59A, substituting 2-(3-(trifluoromethoxy)phenyl)acetonitrile for 2-(3,4-dichlorophenyl)acetonitrile.

Example 66B pyridin-2-yl(4-(3-(trifluoromethoxy)phenyl)tetrahydro-2H-pyran-4-yl)methanone The title compound was prepared according to the procedure of Example 59B, substituting Example 66A for Example 59A.

Example 66C pyridin-2-yl {4-[3-(trifluoromethoxy)phenyl]tetrahydro-2H-pyran-4-yl}methanol The title compound was prepared according to the procedure of Example 59C, substituting Example 66B for Example 59B. $^1$H NMR (400 MHz, CDCl$_3$): 8.35 (d, J=4.4 Hz, 1H), 7.46 (td, J=2.4 Hz, J=8.0 Hz, 1H), 7.31 (t, J=8.0 Hz, 1H), 7.108-7.14 (m, 3H), 6.72 (s, 1H), 6.53 (d, J=7.6 Hz, 1H), 4.63 (s, 1H), 4.48 (br, 1H), 3.83-3.90 (m, 2H), 3.29-3.43 (m, 2H), 2.30-2.38 (m, 1H), 2.09-2.22 (m, 3H).

Example 67 pyridin-2-yl {4-[4-(trifluoromethoxy)phenyl]tetrahydro-2H-pyran-4-yl}methanol

Example 67A 4-(4-(trifluoromethoxy)phenyl)tetrahydro-2H-pyran-4-carbonitrile The title compound was prepared according to the procedure of Example 59A, substituting 2-(4-(trifluoromethoxy)phenyl)acetonitrile for 2-(3,4-dichlorophenyl)acetonitrile.

Example 67B pyridin-2-yl(4-(4-(trifluoromethoxy)phenyl)tetrahydro-2H-pyran-4-yl)methanone The title compound was prepared according to the procedure of Example 59B, substituting Example 67A for Example 59A.

Example 67C pyridin-2-yl {4-[4-(trifluoromethoxy)phenyl]tetrahydro-2H-pyran-4-yl}methanol The title compound was prepared according to the procedure of Example 59C, substituting Example 67B for Example 59B. $^1$H NMR (400 MHz, CDCl$_3$): 8.34 (d, J=4.4 Hz, 1H), 7.45 (td, J=1.2 Hz, J=7.6 Hz, 1H), 7.01-7.13 (m, 5H), 6.54 (s, 1H), 6.53 (d, J=7.6 Hz, 1H), 4.62 (s, 1H), 4.41 (br, 1H), 3.83-3.88 (m, 2H), 3.31-3.45 (m, 2H), 2.28-2.34 (m, 1H), 2.10-2.17 (m, 3H).

Example 68

2-(1-phenylcyclobutyl)-1-(pyridin-2-yl)ethanol

Example 68A ethyl 2-cyano-2-cyclobutylideneacetate

HMDS (69.6 g, 0.43 mol) was added dropwise to 350 mL of acetic acid at ambient temp over 5 minutes. Cyclopentanone (20.3 g, 0.29 mol) and ethyl cyanoacetate (65.0 g, 0.57 mol) were added in single portions to the resulting solution. The mixture was stirred at 70° C. overnight after which it was cooled to ambient temperature and the reacting mixture was poured into 600 mL of water, and extracted with ethyl acetate (500 mL×3). The combined organic layers were dried over $Na_2SO_4$, filtered, and concentrated to afford the crude product, which was purified by flash chromatography (petroleum ether: ethyl acetate=10:1) to give the title compound as a yellow solid (37.0 g, 0.22 mol, 77.2%). LC-MS: m/e=166.2 $(M+H^+)$.

Example 68B ethyl 2-cyano-2-(1-phenylcyclobutyl)acetate

To a solution of Example 68A (3.0 g, 18.2 mmol) in ether (70 mL) was added dropwise phenyl magnesium bromide (9.0 mL, 3.0 M solution in diethyl ether, 27.4 mmol). The mixture was heated to 60° C. and stirred at this temp for 1 hour after addition was completed. The reaction mixture was cooled to ambient temperature. The resulting dark yellow solution was poured onto crushed ice and the pH was adjusted to about 5-6 with the addition of 20% $H_2SO_4$. The mixture was extracted with ethyl acetate/diethyl ether (1:1) (50 mL×2). The combined organic layers were washed with water and brine sequentially, dried over $Na_2SO_4$, filtered, and concentrated. The crude product was purified by reserve-phase C18 column chromatography (eluted with $H_2O$/MeOH=1:4) to afford the desired compound (3.7 g, 15.2 mmol, 83.6%). LC-MS: m/e=261.1 $(M^++18)$. $^1H$ NMR (400 MHz, $CDCl_3$), δ (ppm): 7.36-7.23 (m, 5H), 4.00 (q, J=6.8, Hz, $J_2$=14.4 Hz, 2H), 3.91 (s, 1H), 2.80-2.73 (m, 1H), 2.65-2.55 (m, 3H), 2.21-2.07 (m, 1H), 1.99-1.88 (m, 1H), 1.05 (t, J=7.2 Hz, 3H).

Example 68C 2-(1-phenylcyclobutyl)acetic acid

Example 68B (3.4 g, 14.0 mmol) was dissolved in a 15% w/w solution of KOH (104.6 g) in ethylene glycol and the mixture was heated to 200° C. (used blast shield) slowly. The reaction was monitored by LC/MS until the disappearance of the starting material. The reaction mixture was cooled to ambient temperature, diluted with water (200 mL), and the pH was adjusted to about 3 with concentrated HCl. The aqueous layer was extracted with dichloromethane (150 mL×3). The combined organic layers were dried over $Na_2SO_4$, filtered, and concentrated. The crude product was used in the next step without further purification (2.0 g, 10.5 mmol, 75.2%).

Example 68D

N-methoxy-N-methyl-2-(1-phenylcyclobutyl)acetamide

A suspension of Example 68C (2.0 g, 10.5 mmol), N,O-dimethylhydroxylamine hydrochloride (1.5 g, 15.8 mmol), HATU (4.8 g, 12.6 mmol) and triethylamine (2.1 g, 21.0 mmol) in 100 mL dichloromethane was stirred at room temperature overnight. The resulting mixture was diluted with water (100 mL) and the aqueous layer was extracted with dichloromethane (50 mL×3). The combined organic layer was dried over $Na_2SO_4$, filtered, and concentrated to afford yellow oil. The crude product was purified by reserve-phase C18 column chromatography ($H_2O$/$CH_3OH$=1:4) to afford desired compound (2.2 g, 9.4 mmol, 89.5%) of title compound. LC-MS: m/e=234.1 $(M+H^+)$.

Example 68E 2-(1-phenylcyclobutyl)-1-(pyridin-2-yl)ethanone

To a solution of 2-bromopyridine (1.0 g, 4.3 mmol) in dry tetrahydrofuran (30 mL) 1.6 M n-butyl lithium in hexanes (4.8 mL) was added dropwise at −78° C. The mixture was kept at this temperature for 1 hour, followed by addition of a solution of Example 68D in tetrahydrofuran. At the end of addition, the mixture was allowed to reach ambient temperature and stirred at 60° C. for 2 hours. The mixture was then cooled to 0° C., and diluted with ether (50 mL) and saturated aqueous $NH_4Cl$ (60 mL). The organic phase was separated, dried over $Na_2SO_4$, filtered, and concentrated. The crude product was used in the next step without further purification (1.5 g, 5.97 mmol).

LC-MS: m/e=252.4 $(M+H^+)$.

Example 68F 2-(1-phenylcyclobutyl)-1-(pyridin-2-yl)ethanol

To a solution of Example 68E (1.5 g) in 27 mL of dichloromethane:methanol (9:1) was added $NaBH_4$ (0.1 g, 2.6 mmol). The reaction was monitored by LC/MS, dichloromethane was added to the solution upon completion of the reaction. The mixture was washed with water, dried over $Na_2SO_4$, and filtered. The crude product was purified by preparative-HPLC (eluted with petroleum ether/EtOAc=5:1) to afford title compound (0.4 g, 1.6 mmol, 37.2%). LC-Ms: ESI-MS $(M+H^+)$: m/e=254.2. $^1H$ NMR (400 MHz, $CDCl_3$), δ (ppm): 10.82 (br, 2H), 8.59 (d, J=5.2 Hz, 1H), 8.06 (td, J=2.0 Hz, $J_2$=7.8 Hz, 1H), 7.60 (t, J=6.4 Hz, 1H), 7.29-7.24 (m, 3H), 7.19-7.11 (m, 3H), 4.75 (q, J=4.8 Hz, $J_2$=8.0 Hz 1H), 2.67 (q, $J_1$=7.3 Hz, $J_2$=14.2 Hz 1H), 2.54-2.50 (m, 2H), 2.39-2.08 (m, 4H), 1.89-1.82 (m, 1H).

Example 69

2-[1-(4-chlorophenyl)cyclobutyl]-1-(pyridin-2-yl)ethanol

Example 69A ethyl 2-(1-(4-chlorophenyl)cyclobutyl)-2-cyanoacetate

The title compound was prepared according to the procedure of Example 68B, substituting 4-chlorophenylmagnesium bromide for phenylmagnesium bromide. LC-MS: m/e=300.1 $(M^++23)$.

Example 69B 2-(1-(4-chlorophenyl)cyclobutyl)acetic acid

The title compound was prepared according to the procedure of Example 68C, substituting Example 69A for Example 68B.

Example 69C 2-(1-(4-chlorophenyl)cyclobutyl)-N-methoxy-N-methylacetamide

The title compound was prepared according to the procedure of Example 68D, substituting Example 69B for Example 68C. LC-MS: m/e=268.1 (M+H$^+$).

Example 69D 2-(1-(4-chlorophenyl)cyclobutyl)-1-(pyridin-2-yl)ethanone

The title compound was prepared according to the procedure of Example 68E, substituting Example 69C for Example 68D. LC-MS: m/e=286.2 (M+H$^+$).

Example 69E

2-[1-(4-chlorophenyl)cyclobutyl]-1-(pyridin-2-yl)ethanol

The title compound was prepared according to the procedure of Example 68F, substituting Example 69D for Example 68E. LC-Ms: ESI-MS (M+H$^+$): m/e=288.2. $^1$H NMR (400 MHz, CDCl$_3$), δ (ppm): 8.60 (d, J=5.6 Hz, 1H), 8.18-8.06 (m, 3H), 7.68 (t, J=6.4 Hz, 1H), 7.41 (d, J=8.0 Hz, 1H), 7.22 (dd, J=2.0 Hz, J$_2$=6.8 Hz, 4H), 4.74 (q, J$_1$=4.0 Hz, J$_2$=8.8 Hz, 1H), 2.61 (q, J$_1$=8.6 Hz, J$_2$=14.2 Hz, 1H), 2.54-2.43 (m, 2H), 2.37-2.30 (m, 1H), 2.22-2.03 (m, 3H), 1.89-1.80 (m, 1H).

Example 70

2-[1-(4-fluorophenyl)cyclobutyl]-1-(pyridin-2-yl)ethanol

Example 70A ethyl 2-cyano-2-(1-(4-fluorophenyl)cyclobutyl)acetate

The title compound was prepared according to the procedure of Example 68B, substituting 4-fluorophenylmagnesium bromide for phenylmagnesium bromide. LC-MS: m/e=279.2 (M$^+$+18).

Example 70B 2-(1-(4-fluorophenyl)cyclobutyl)acetic acid

The title compound was prepared according to the procedure of Example 68C, substituting Example 70A for Example 68B.

Example 70C 2-(1-(4-fluorophenyl)cyclobutyl)-N-methoxy-N-methylacetamide

The title compound was prepared according to the procedure of Example 68D, substituting Example 70B for Example 68C. LC-MS: m/e=252.2 (M+H$^+$).

Example 70D 2-(1-(4-fluorophenyl)cyclobutyl)-1-(pyridin-2-yl)ethanone

The title compound was prepared according to the procedure of Example 68E, substituting Example 70C for Example 68D. LC-MS: m/e=270.2 (M+H$^+$);

Example 70E

2-[1-(4-fluorophenyl)cyclobutyl]-1-(pyridin-2-yl)ethanol

The title compound was prepared according to the procedure of Example 68F, substituting Example 70D for Example 68E. LC-Ms: ESI-MS (M+H$^+$): m/e=272.2. $^1$H NMR (400 MHz, CDCl$_3$), δ (ppm): 8.61 (d, J=5.6 Hz, 1H), 8.15 (td, J=1.2, Hz, J$_2$=7.8 Hz, 1H), 7.67-7.59 (m, 4H), 7.41 (d, J=8.0 Hz, 1H), 7.15 (td, J$_1$=2.4, Hz, J$_2$=6.0 Hz, 2H), 6.94 (t, J=8.8 Hz, 2H), 4.72 (q, J$_1$=4.0 Hz, J$_2$=8.8 Hz, 1H), 2.60 (q, J=8.4 Hz, J$_2$=14.0 Hz, 1H), 2.55-2.43 (m, 2H), 2.36-2.29 (m, 1H), 2.20-2.05 (m, 3H), 1.88-1.80 (m, 1H).

Example 71

2-[1-(3-fluorophenyl)cyclobutyl]-1-(pyridin-2-yl)ethanol

Example 71A ethyl 2-cyano-2-(1-(3-fluorophenyl)cyclobutyl)acetate

The title compound was prepared according to the procedure of Example 68B, substituting 3-fluorophenylmagnesium bromide for phenylmagnesium bromide. LC-MS: m/e=262.3 (M+H$^+$).

Example 71B 2-(1-(3-fluorophenyl)cyclobutyl)acetic acid

The title compound was prepared according to the procedure of Example 68C, substituting Example 71A for Example 68B.

Example 71C 2-(1-(3-fluorophenyl)cyclobutyl)-N-methoxy-N-methylacetamide

The title compound was prepared according to the procedure of Example 68D, substituting Example 71B for Example 68C. LC-MS: m/e=252.2 (M+H$^+$).

Example 71D 2-(1-(3-fluorophenyl)cyclobutyl)-1-(pyridin-2-yl)ethanone

The title compound was prepared according to the procedure of Example 68E, substituting Example 71C for Example 68D. LC-MS: m/e=270.1 (M+H⁺).

Example 71E

2-[1-(3-fluorophenyl)cyclobutyl]-1-(pyridin-2-yl)ethanol

The title compound was prepared according to the procedure of Example 68F, substituting Example 71D for Example 68E. LC-Ms: ESI-MS (M+H⁺): m/e=272.1. $^1$H NMR (400 MHz, CDCl$_3$), δ (ppm): 10.94 (br, 2H), 8.62 (d, J=5.6 Hz, 1H), 8.15 (td, J$_1$=1.1, Hz, J$_2$=8.0 Hz, 1H), 7.65 (t, J=6.4 Hz, 1H), 7.4 (d, J=8.0 Hz, 1H), 7.27-7.22 (m, 1H), 7.00 (d, J=7.6 Hz, 1H), 6.88-6.82 (m, 2H), 4.74 (q, J$_1$=4.3 Hz, J$_2$=8.4 Hz, 1H), 2.66 (q, J$_1$=7.6 Hz, J$_2$=14.4 Hz, 1H) 1H), 2.56-2.47 (m, 2H), 2.37-2.31 (m, 1H), 2.23-2.07 (m, 3H), 1.90-1.81 (m, 1H).

Example 72

2-[1-(3-chlorophenyl)cyclobutyl]-1-(pyridin-2-yl)ethanol

Example 72A ethyl 2-(1-(3-chlorophenyl)cyclobutyl)-2-cyanoacetate

The title compound was prepared according to the procedure of Example 68B, substituting 3-chlorophenylmagnesium bromide for phenylmagnesium bromide. LC-MS: m/e=278.1 (M+H⁺).

Example 72B 2-(1-(3-chlorophenyl)cyclobutyl)acetic acid

The title compound was prepared according to the procedure of Example 68C, substituting Example 72A for Example 68B.

Example 72C 2-(1-(3-chlorophenyl)cyclobutyl)-N-methoxy-N-methylacetamide

The title compound was prepared according to the procedure of Example 68D, substituting Example 72B for Example 68C. LC-MS: m/e=268.1 (M+H⁺).

Example 72D 2-(1-(3-chlorophenyl)cyclobutyl)-1-(pyridin-2-yl)ethanone

The title compound was prepared according to the procedure of Example 68E, substituting Example 72C for Example 68D. LC-MS: m/e=286.2 (M+H⁺).

Example 72E

2-[1-(3-chlorophenyl)cyclobutyl]-1-(pyridin-2-yl)ethanol

The title compound was prepared according to the procedure of Example 68F, substituting Example 72D for Example 68E. LC-Ms: ESI-MS (M+H⁺): 288.2. $^1$H NMR (400 MHz, CDCl$_3$), δ (ppm): 11.05 (br, 2H), 8.60 (d, J=5.6 Hz, 1H), 8.13 (t, J=7.2 Hz, 1H), 7.63 (t, J=6.6 Hz, 1H), 7.38 (d, J=8.0 Hz, 1H), 7.21 (t, J=8.0 Hz, 1H), 7.12-7.10 (m, 3H), 4.73 (q, J=4.8 Hz, J$_2$=8.4 Hz, 1H), 2.68 (q, J$_1$=8.4 Hz, J$_2$=14.0 Hz, 1H), 2.58-2.45 (m, 2H), 2.36-2.29 (m, 1H), 2.25-2.06 (m, 3H), 1.90-1.81 (m, 1H).

Example 73

2-[1-(3,4-dichlorophenyl)cyclobutyl]-1-(pyridin-2-yl)ethanol

Example 73A ethyl 2-cyano-2-(1-(3,4-dichlorophenyl)cyclobutyl)acetate

The title compound was prepared according to the procedure of Example 68B, substituting 3,4-dichlorophenylmagnesium bromide for phenylmagnesium bromide. LC-MS: m/e=334.1 (M⁺+23).

Example 73B 2-(1-(3,4-dichlorophenyl)cyclobutyl)acetic acid

The title compound was prepared according to the procedure of Example 68C, substituting Example 73A for Example 68B.

Example 73C 2-(1-(3,4-dichlorophenyl)cyclobutyl)-N-methoxy-N-methylacetamide The title compound was prepared according to the procedure of Example 68D, substituting Example 73B for Example 68C. LC-MS: m/e=302.0 (M+H⁺).

Example 73D 2-(1-(3,4-dichlorophenyl)cyclobutyl)-1-(pyridin-2-yl)ethanone

The title compound was prepared according to the procedure of Example 68E, substituting Example 73C for Example 68D. LC-MS: m/e=320.2 (M+H⁺).

Example 73E

2-[1-(3,4-dichlorophenyl)cyclobutyl]-1-(pyridin-2-yl)ethanol

The title compound was prepared according to the procedure of Example 68F, substituting Example 73D for Example 68E. LC-Ms: ESI-MS (M+H⁺): m/e=322.1. $^1$H NMR (400 MHz, CDCl$_3$), δ (ppm): 8.48 (d, J=4.4 Hz, 1H), 7.58 (td, J=1.7 Hz, J$_2$=7.7 Hz, 1H), 7.38-7.34 (m, 2H), 7.15-7.12 (m, 2H), 6.99 (d, J=7.6 Hz, 1H), 4.35 (d, J=8.4 Hz, 1H), 3.90 (br, 1H), 2.64-2.57 (m, 1H), 2.46-2.39 (m, 1H), 2.35-2.26 (m, 2H), 2.17-2.03 (m, 3H), 1.86-1.77 (m, 1H).

Example 74

1-(pyridin-2-yl)-2-{1-[3-(trifluoromethyl)phenyl] cyclobutyl}ethanol

Example 74A ethyl 2-cyano-2-(1-(3-(trifluoromethyl)phenyl)cyclobutyl)acetate The title compound was prepared according to the procedure of Example 68B, substituting 3-trifluoromethylphenylmagnesium bromide for phenylmagnesium bromide.

Example 74B 2-(1-(3-(trifluoromethyl)phenyl)cyclobutyl)acetic acid

The title compound was prepared according to the procedure of Example 68C, substituting Example 74A for Example 68B.

Example 74C

N-methoxy-N-methyl-2-(1-(3-(trifluoromethyl)phenyl)cyclobutyl)acetamide

The title compound was prepared according to the procedure of Example 68D, substituting Example 74B for Example 68C. LC-MS: m/e=302.1 (M+H$^+$).

Example 74D 1-(pyridin-2-yl)-2-(1-(3-(trifluoromethyl)phenyl) cyclobutyl)ethanone The title compound was prepared according to the procedure of Example 68E, substituting Example 74C for Example 68D. LC-MS: m/e=320.4 (M+H$^+$).

Example 74E 1-(pyridin-2-yl)-2-{1-[3-(trifluoromethyl)phenyl] cyclobutyl}ethanol The title compound was prepared according to the procedure of Example 68F, substituting Example 74D for Example 68E. LC-Ms: ESI-MS (M+H$^+$) m/e=322.1. $^1$H NMR (400 MHz, CDCl$_3$), δ (ppm): 8.48 (d, J=4.8 Hz, 1H), 7.58-7.41 (m, 5H), 7.13 (q, J=5.4 Hz, J$_2$=7.0 Hz, 1H), 6.94 (d, J=8.0 Hz, 1H), 4.34 (dd, J$_1$=3.0 Hz, J$_2$=9.4 Hz, 1H), 3.79 (br, 1H), 2.68-2.62 (m, 1H), 2.53-2.46 (m, 1H), 2.41-2.31 (m, 2H), 2.22-2.05 (m, 3H), 1.88-1.79 (m, 1H).

Example 75

1-(pyridin-2-yl)-2-{1-[4-(trifluoromethyl)phenyl] cyclobutyl}ethanol

Example 75A ethyl 2-cyano-2-(1-(4-(trifluoromethyl)phenyl)cyclobutyl)acetate The title compound was prepared according to the procedure of Example 68B, substituting 4-trifluoromethylphenylmagnesium bromide for phenylmagnesium bromide. LC-MS: m/e=312.1 (M+H$^+$).

Example 75B 2-(1-(4-(trifluoromethyl)phenyl)cyclobutyl)acetic acid

The title compound was prepared according to the procedure of Example 68C, substituting Example 75A for Example 68B.

Example 75C

N-methoxy-N-methyl-2-(1-(4-(trifluoromethyl)phenyl)cyclobutyl)acetamide

The title compound was prepared according to the procedure of Example 68D, substituting Example 75B for Example 68C. LC-MS: m/e=302.4 (M+H$^+$).

Example 75D 1-(pyridin-2-yl)-2-(1-(4-(trifluoromethyl)phenyl) cyclobutyl)ethanone The title compound was prepared according to the procedure of Example 68E, substituting Example 75C for Example 68D. LC-MS: m/e=320.4 (M+H$^+$).

Example 75E 1-(pyridin-2-yl)-2-{1-[4-(trifluoromethyl)phenyl] cyclobutyl}ethanol The title compound was prepared according to the procedure of Example 68F, substituting Example 75D for Example 68E. LC-Ms: ESI-MS (M+H$^+$): m/e=322.2. $^1$H NMR (400 MHz, CDCl$_3$), δ (ppm): 8.49 (d, J=4.4 Hz, 1H), 7.59-7.55 (m, 3H), 7.40 (d, J=8.4 Hz, 2H), 7.14 (q, J=5.2 Hz, J$_2$=6.8 Hz, 1H), 6.95 (d, J=7.6 Hz, 1H), 4.34 (dd, J$_1$=3.0 Hz, J$_2$=11.2 Hz, 1H), 2.69-2.62 (m, 1H), 2.51 (q, J=8.8 Hz, J$_2$=20.0 Hz, 1H), 2.42-2.31 (m, 2H), 2.22-2.04 (m, 3H), 1.88-1.78 (m, 1H).

Example 76

1-(pyridin-2-yl)-2-{1-[4-(trifluoromethoxy)phenyl] cyclobutyl}ethanol

Example 76A ethyl 2-cyano-2-(1-(4-(trifluoromethoxy)phenyl) cyclobutyl)acetate The title compound was prepared according to the procedure of Example 68B, substituting 4-trifluoromethoxyphenylmagnesium bromide for phenylmagnesium bromide. LC-MS: m/e=345.2 ($M^+$+18).

Example 76B 2-(1-(4-(trifluoromethoxy)phenyl)cyclobutyl)acetic acid

The title compound was prepared according to the procedure of Example 68C, substituting Example 76A for Example 68B.

Example 76C

N-methoxy-N-methyl-2-(1-(4-(trifluoromethoxy) phenyl)cyclobutyl)acetamide

The title compound was prepared according to the procedure of Example 68D, substituting Example 76B for Example 68C. LC-MS: m/e=318.3 (M+$H^+$).

Example 76D 1-(pyridin-2-yl)-2-(1-(4-(trifluoromethoxy)phenyl) cyclobutyl)ethanone The title compound was prepared according to the procedure of Example 68E, substituting Example 76C for Example 68D. LC-MS: m/e=336.2 (M+$H^+$).

Example 76E 1-(pyridin-2-yl)-2-{1-[4-(trifluoromethoxy)phenyl] cyclobutyl}ethanol The title compound was prepared according to the procedure of Example 68F, substituting Example 76D for Example 68E. LC-Ms: ESI-MS (M+$H^+$): m/e=338.2. $^1$H NMR (400 MHz, $CDCl_3$), δ (ppm): 10.83 (br, 2H), 8.58 (d, J=5.2 Hz, 1H), 8.13 (t, J=7.8 Hz, 1H), 7.64 (d, J=6.6 Hz, 1H), 7.40 (d, J=8.0 Hz, 1H), 7.14 (dd, $J_1$=8.6 Hz, $J_2$=47.4 Hz, 4H), 4.76 (q, J=4.0 Hz, $J_2$=7.8 Hz, 1H), 2.64 (q, J=7.5 Hz, $J_2$=14.2 Hz, 1H), 2.51-2.44 (m, 2H), 2.37-2.30 (m, 1H), 2.25-2.04 (m, 3H), 1.89-1.80 (m, 1H).

Example 77

1-(pyridin-2-yl)-2-{1-[3-(trifluoromethoxy)phenyl] cyclobutyl}ethanol

Example 77A ethyl 2-cyano-2-(1-(3-(trifluoromethoxy)phenyl) cyclobutyl)acetate The title compound was prepared according to the procedure of Example 68B, substituting 3-trifluoromethoxyphenylmagnesium bromide for phenylmagnesium bromide. LC-MS: m/e=345.0 ($M^+$+18).

Example 77B 2-(1-(3-(trifluoromethoxy)phenyl)cyclobutyl)acetic acid

The title compound was prepared according to the procedure of Example 68C, substituting Example 77A for Example 68B.

Example 77C

N-methoxy-N-methyl-2-(1-(3-(trifluoromethoxy) phenyl)cyclobutyl)acetamide

The title compound was prepared according to the procedure of Example 68D, substituting Example 77B for Example 68C. LC-MS: m/e=318.0 (M+$H^+$).

Example 77D 1-(pyridin-2-yl)-2-(1-(3-(trifluoromethoxy)phenyl) cyclobutyl)ethanone The title compound was prepared according to the procedure of Example 68E, substituting Example 77C for Example 68D. LC-MS: m/e=336.2 (M+$H^+$).

Example 77E 1-(pyridin-2-yl)-2-{1-[3-(trifluoromethoxy)phenyl] cyclobutyl}ethanol The title compound was prepared according to the procedure of Example 68F, substituting Example 77D for Example 68E. LC-Ms: ESI-MS (M+$H^+$): m/e=338.1. $^1$H NMR (400 MHz, $CDCl_3$), δ (ppm): 8.50 (d, J=4.8 Hz, 1H), 7.59 (td, $J_1$=1.9 Hz, $J_2$=7.6 Hz, 1H), 7.35 (t, J=8.0 Hz, 1H), 7.26-7.23 (m, 1H), 7.17-7.12 (m, 2H), 7.05 (dd, J=1.0 Hz, $J_2$=8.2 Hz, 1H), 6.94 (d, J=7.6 Hz, 1H), 4.36 (dd, $J_1$=3.0 Hz, $J_2$=9.4 Hz, 1H), 3.77 (br, 1H), 2.66-2.59 (m, 1H), 2.52-2.45 (m, 1H), 2.39-2.30 (m, 2H), 2.18-2.06 (m, 3H), 1.88-1.79 (m, 1H).

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

The invention claimed is:
1. A compound according to formula (I):

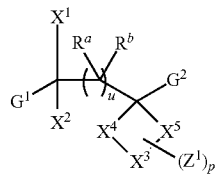

or a pharmaceutically acceptable salt thereof, wherein
$R^a$ and $R^b$ are absent;
u is 0;
$X^3$ is O;
$X^4$ is $(CH_2)_m$ and $X^5$ is $(CH_2)_n$;
m and n are each 2;
each $Z^1$ group is an optional substituent on any substitutable carbon atom of the ring containing $X^3$, $X^4$, and $X^5$, and is independently alkyl, O(alkyl), oxo, halogen, haloalkyl, or OH; two $Z^1$ groups that are resided on the same carbon atom, together with the carbon atom to which they are attached optionally form a 4-6 membered monocyclic heterocycle ring containing one or two oxygen atoms;
p is 0;
—$X^1$ is —OH and $X^2$ is hydrogen;
$G^1$ is unsubstituted pyrimidinyl or pyridinyl;
$G^2$ is $G^{2d}$ wherein
$G^{2d}$ is aryl, optionally substituted with 1, 2, 3, 4, or 5 substituents independently selected from the group consisting of $G^d$, alkyl, alkenyl, alkynyl, halogen, haloalkyl, —CN, —OC(O)$R^f$, —OC(O)N($R^f$)$_2$, —S(O)$_2R^e$, —S(O)$_2$N($R^f$)$_2$, —C(O)$R^f$, —C(O)O$R^f$, —C(O)N($R^f$)$_2$, —N($R^f$)$_2$, —N($R^f$)C(O)$R^f$, —N($R^f$)S(O)$_2R^e$, —N($R^f$)C(O)O($R^e$), —N($R^f$)C(O)N($R^f$)$_2$, —(CR$^{1a}$R$^{1b}$)$_q$—OR$^f$, —(CR$^{1a}$R$^{1b}$)$_q$—OC(O)R$^f$, —(CR$^{1a}$R$^{1b}$)$_q$—OC(O)N($R^f$)$_2$, —(CR$^{1a}$R$^{1b}$)$_q$—S(O)$_2R^e$, —(CR$^{1a}$R$^{1b}$)$_q$—S(O)$_2$N($R^f$)$_2$, —(CR$^{1a}$R$^{1b}$)$_q$—C(O)$R^f$, —(CR$^{1a}$R$^{1b}$)$_q$—C(O)OR$^f$, —(CR$^{1a}$R$^{1b}$)$_q$—C(O)N($R^f$)$_2$, —(CR$^{1a}$R$^{1b}$)$_q$—N($R^f$)$_2$, —(CR$^{1a}$R$^{1b}$)$_q$—N($R^f$)C(O)$R^f$, —(CR$^{1a}$R$^{1b}$)$_q$—N($R^f$)S(O)$_2R^e$, —(CR$^{1a}$R$^{1b}$)$_q$—N($R^f$)C(O)O(Re), —(CR$^{1a}$R$^{1b}$)$_q$—N($R^f$)C(O)N($R^f$)$_2$, and —(CR$^{1a}$R$^{1b}$)$_q$—CN;
$R^{1a}$ and $R^{1b}$, are the same or different, and at each occurrence are each independently hydrogen, alkyl, or haloalkyl;
each occurrence of $R^f$ is independently hydrogen, alkyl, haloalkyl, $G^d$, or —(CR$^{1a}$R$^{1b}$)$_q$-$G^d$;
each occurrence of $R^e$ is independently alkyl, haloalkyl, $G^d$, or —(CR$^{1a}$R$^{1b}$)$_q$-$G^d$;
q, at each occurrence, is independently 1, 2, or 3;
each occurrence of $G^d$ is independently aryl, heteroaryl, cycloalkyl, heterocycle, or cycloalkenyl; and is each optionally substituted with 1, 2, 3, 4, or 5 substituents independently selected from the group consisting of alkyl, alkenyl, alkynyl, halogen, haloalkyl, —CN, —OC(O)$R^j$, —OC(O)N($R^j$)$_2$, —S(O)$_2R^k$, —S(O)$_2$N($R^j$)$_2$, —C(O)$R^j$, —C(O)O$R^j$, —C(O)N($R^j$)$_2$, —N($R^j$)$_2$, —N($R^j$)C(O)$R^j$, —N($R^j$)S(O)$_2R^k$, —N($R^j$)C(O)O($R^k$), —N($R^j$)C(O)N($R^j$)$_2$, —(CR$^{1a}$R$^{1b}$)$_q$—OR$^j$, —(CR$^{1a}$R$^{1b}$)$_q$—OC(O)$R^j$, —(CR$^{1a}$R$^{1b}$)$_q$—OC(O)N($R^j$)$_2$, —(CR$^{1a}$R$^{1b}$)$_q$—S(O)$_2R^k$, —(CR$^{1a}$R$^{1b}$)$_q$—S(O)$_2$N($R^j$)$_2$, —(CR$^{1a}$R$^{1b}$)$_q$—C(O)$R^j$, —(CR$^{1a}$R$^{1b}$)$_q$—C(O)OR$^j$, —(CR$^{1a}$R$^{1b}$)$_q$—C(O)N($R^j$)$_2$, —(CR$^{1a}$R$^{1b}$)$_q$—N($R^j$)$_2$, —(CR$^{1a}$R$^{1b}$)$_q$—N($R^j$)C(O)$R^j$, —(CR$^{1a}$R$^{1b}$)$_q$—N($R^j$)S(O)$_2R^k$, —(CR$^{1a}$R$^{1b}$)$_q$—N($R^j$)C(O)O($R^k$), —(CR$^{1a}$R$^{1b}$)$_q$—N($R^j$)C(O)N($R^j$)$_2$, and —(CR$^{1a}$R$^{1b}$)$_q$—CN;
each occurrence of $R^j$ is independently hydrogen, alkyl, or haloalkyl; and
each occurrence of $R^k$ is independently alkyl or haloalkyl.

2. A compound, or a pharmaceutically acceptable salt thereof, wherein the compound is selected from the group consisting of:
[4-(3,4-dichlorophenyl)tetrahydro-2H-pyran-4-yl](pyridin-2-yl)methanol;
(4-phenyltetrahydro-2H-pyran-4-yl)(pyridin-2-yl)methanol;
[4-(3-fluorophenyl)tetrahydro-2H-pyran-4-yl](pyridin-2-yl)methanol;
[4-(4-fluorophenyl)tetrahydro-2H-pyran-4-yl](pyridin-2-yl)methanol;
[4-(3,4-difluorophenyl)tetrahydro-2H-pyran-4-yl](pyridin-2-yl)methanol;
[4-(4-chlorophenyl)tetrahydro-2H-pyran-4-yl](pyridin-2-yl)methanol;
pyridin-2-yl{4-[4-(trifluoromethyl)phenyl]tetrahydro-2H-pyran-4-yl}methanol;
pyridin-2-yl{4-[3-(trifluoromethoxy)phenyl]tetrahydro-2H-pyran-4-yl}methanol; and
pyridin-2-yl{4-[4-(trifluoromethoxy)phenyl]tetrahydro-2H-pyran-4-yl}methanol.

3. A pharmaceutical composition comprising a therapeutically effective amount of a compound of formula (I) according to claim 1, or a pharmaceutically acceptable salt thereof, in combination with a pharmaceutically acceptable carrier.

4. The compound or salt according to claim 1, wherein $G^1$ is unsubstituted pyridinyl.

5. The compound or salt according to claim 1, wherein $G^1$ is unsubstituted pyridin-2-yl.

6. The compound or salt according to claim 1, wherein $G^{2d}$ is optionally substituted phenyl.

7. The compound or salt according to claim 1, wherein $G^{2d}$ is phenyl, optionally substituted with alkyl, halogen, haloalkyl, or —OR$^f$; and $R^f$ is alkyl or haloalkyl.

8. The compound or salt according to claim 1, wherein $G^1$ is unsubstituted pyridinyl; and $G^{2d}$ is optionally substituted phenyl.

9. The compound or salt according to claim 1, wherein $G^1$ is unsubstituted pyridinyl; $G^{2d}$ is phenyl, optionally substituted with alkyl, halogen, haloalkyl, or —OR$^f$; and $R^f$ is alkyl or haloalkyl.

10. The compound or salt according to claim 1, wherein $G^1$ is unsubstituted pyridin-2-yl; and $G^{2d}$ is optionally substituted phenyl.

11. The compound or salt according to claim 1, wherein $G^1$ is unsubstituted pyridin-2-yl; $G^{2d}$ is phenyl, optionally substituted with alkyl, halogen, haloalkyl, or —OR$^f$; and $R^f$ is alkyl or haloalkyl.

* * * * *